(12) United States Patent
Heinecke et al.

(10) Patent No.: US 8,420,337 B2
(45) Date of Patent: Apr. 16, 2013

(54) LIPOPROTEIN-ASSOCIATED MARKERS FOR CARDIOVASCULAR DISEASE

(75) Inventors: Jay W. Heinecke, Seattle, WA (US); Tomas Vaisar, Bellevue, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 13/104,757

(22) Filed: May 10, 2011

(65) Prior Publication Data

US 2011/0212477 A1    Sep. 1, 2011

Related U.S. Application Data

(62) Division of application No. 11/263,553, filed on Oct. 31, 2005, now Pat. No. 7,972,802.

(51) Int. Cl.
*G01N 31/00* (2006.01)
*G01N 33/53* (2006.01)

(52) U.S. Cl.
USPC ............ 435/7.21; 435/7.1; 436/501; 436/518

(58) Field of Classification Search .................. None
See application file for complete search history.

(56) References Cited

U.S. PATENT DOCUMENTS

| | | | |
|---|---|---|---|
| 4,677,057 A | 6/1987 | Curtiss | |
| 6,107,045 A | 8/2000 | Koren | |
| 6,225,047 B1 | 5/2001 | Hutchens | |
| 6,521,226 B1 | 2/2003 | Radtke | |
| 6,677,114 B1 | 1/2004 | Schneider | |
| 6,869,568 B2 | 3/2005 | Fogelman | |
| 7,098,036 B2 | 8/2006 | Koren | |
| 7,223,552 B2 | 5/2007 | Hazen | |
| 7,238,475 B2 | 7/2007 | Rubin | |
| 2002/0164598 A1 | 11/2002 | Muhlestein | |
| 2004/0053321 A1 | 3/2004 | Koren | |
| 2004/0053367 A1 | 3/2004 | Griffin | |
| 2004/0096917 A1 | 5/2004 | Ivey | |
| 2004/0158879 A1 | 8/2004 | Ruvkun | |
| 2004/0197823 A1 | 10/2004 | Najib | |
| 2004/0198656 A1 | 10/2004 | Najib | |
| 2005/0003341 A1 | 1/2005 | Polansky | |
| 2005/0079562 A1 | 4/2005 | Thompson | |
| 2005/0142569 A1 | 6/2005 | Guild | |
| 2005/0181451 A1 | 8/2005 | Bates | |
| 2005/0192755 A1 | 9/2005 | Nagalla | |

FOREIGN PATENT DOCUMENTS

| | | |
|---|---|---|
| EP | 0 767 914 B1 | 4/1997 |
| EP | 1 186 299 A1 | 3/2002 |
| WO | 86/05493 A1 | 9/1986 |
| WO | 87/02059 A1 | 4/1987 |
| WO | 88/03175 A1 | 5/1988 |
| WO | 96/00903 A1 | 1/1996 |
| WO | 00/49043 A2 | 8/2000 |
| WO | 02/23191 A1 | 3/2002 |
| WO | 02/063005 A2 | 8/2002 |
| WO | 03/023407 A1 | 3/2003 |
| WO | 03/025150 A2 | 3/2003 |
| WO | 03/083081 A2 | 10/2003 |
| WO | 2004/043238 A2 | 5/2004 |
| WO | 2004/044165 A2 | 5/2004 |
| WO | 2005/011474 A2 | 2/2005 |

OTHER PUBLICATIONS

Allan, C.M., and J.M. Taylor, "Expression of a Novel Human Apolipoprotein (apoC-IV) Causes Hypertriglyceridemia in Transgenic Mice," Journal of Lipid Research 37(7):1510-1518, Jul. 1996.
Ansell, B.J., et al., "Inflammatory/Antiinflammatory Properties of High-Density Lipoprotein Distinguish Patients From Control Subjects Better Than High-Density Lipoprotein Cholesterol Levels and Are Favorably Affected by Simvastatin Treatment," Circulation 108(22):2751-2756, Dec. 2003.
Artl, A., et al., "Role of Serum Amyloid A During Metabolism of Acute-Phase HDL by Macrophages," Arteriosclerosis, Thrombosis, and Vascular Biology 20(3):763-772, Mar. 2000.
Asztalos, B.F., and E.J. Schaefer, "High-Density Lipoprotein Subpopulations in Pathologic Conditions," American Journal of Cardiology 91(7A):12E-17E, Apr. 2003.
Ayub, A., et al., "Serum Paraoxonase After Myocardial Infarction," Arteriosclerosis, Thrombosis, and Vascular Biology 19(2):330-335, Feb. 1999.
Barter, P.J., et al., "Antiinflammatory Properties of HDL," Circulation Research 95(8):764-772, Oct. 2004.
Bergmeier, C., et al., "Distribution Spectrum of Paraoxonase Activity in HDL Fractions," Clinical Chemistry 50(12):2309-2315, Dec. 2004.
Bergt, C., et al., "The Myeloperoxidase Product Hypochlorous Acid Oxides HDL in the Human Artery Wall and Impairs ABCA1-Dependent Cholesterol Transport," Proceedings of the National Academy of Sciences of the United States of America (PNAS) 101(35):13032-13037, Aug. 2004.
Brinkmann, V., et al., "Neutrophil Extracellular Traps Kill Bacteria," Science 303(5663):1532-1535, Mar. 2004, 9 pages of supplemental online materials.
Bu, X., et al., "Linkage Analysis of the Genetic Determinants of High Density Lipoprotein Concentrations and Composition: Evidence for Involvement of the Apolipoprotein A-II and Cholesteryl Ester Transfer Protein Loci," Human Genetics 93(6):639-648, Jun. 1994.
Buring, J.E., "Decreased HDL2 and HDL3 Cholesterol, Apo A-I and Apo A-II, and Increased Risk of Myocardial Infarction," Circulation 85(1):22-29, Jan. 1992.
Chait, A., et al., "Thematic Review Series: The Immune System and Atherogenesis. Lipoprotein-Associated Inflammatory Proteins: Markers or Mediators of Cardiovascular Disease?" Journal of Lipid Research, 46(3):389-403, Mar. 2005.

(Continued)

*Primary Examiner* — Lisa Cook
(74) *Attorney, Agent, or Firm* — Christensen O'Connor Johnson Kindness PLLC

(57) ABSTRACT

The invention provides methods of screening a mammalian subject to determine if the subject is at risk to develop, or is suffering from, cardiovascular disease. The methods comprise detecting an amount of at least one biomarker in a biological sample, or HDL subfraction thereof, from the subject, and comparing the detected amount of the biomarker to a predetermined value, where a difference between the detected amount and the predetermined value is indicative of the presence or risk of cardiovascular disease in the subject. In some embodiments, the biomarker comprises at least one of ApoC-IV, Paraoxonase 1, C3, C4, ApoA-IV, ApoE, ApoL1, C4B1, Histone H2A, ApoC-II, ApoM, Vitronectin, Haptoglobin-related protein, and Clusterin, or combinations thereof.

6 Claims, 6 Drawing Sheets

OTHER PUBLICATIONS

Daugherty, A., et al., "Hypercholesterolemia Stimulates Angiotensin Peptide Synthesis and Contributes to Atherosclerosis Through the AT 1A Receptor," Circulation 110(25):3849-3857, Dec. 2004.

Emlen, W., et al., "Regulation of Nuclear Antigen Expression on the Cell Surface of Human Monocytes," Journal of Immunology 148(10):3042-3048, May 1992.

Ezeh, B., et al., "Plasma Distribution of apoA-IV in Patients With Coronary Artery Disease and Healthy Controls," Journal of Lipid Research 44(8):1523-1529, Aug. 2003.

Frank, M.M., "Annihilating Host Defense," Nature Medicine 7(12):1285-1286, Dec. 2001.

Getz, G.S., "Thematic Review Series: The Immune System and Atherogenesis. Immune Function in Atherogenesis," Journal of Lipid Research 46(1):1-10, Jan. 2005.

Ghazalpour, A., et al., "Thematic Review Series: The Pathogenesis of Atherosclerosis. Toward a Biological Network for Atherosclerosis," Journal of Lipid Research 45(10):1793-1805, Oct. 2004, 4 pages of supplemental online materials.

Gordon, D.J., and B.M. Rifkind, "High-Density Lipoprotein—The Clinical Implications of Recent Studies," New England Journal of Medicine 321(19):1311-1316, Nov. 1989.

Gygi, S.P., et al., "Quantitative Analysis of Complex Protein Mixtures Using Isotope-Coded Affinity Tags," Nature Biotechnology 17(10):994-999, Oct. 1999.

Halkes, C.J.M., et al., "Postprandial Increase of Complement Component 3 in Normolipidemic Patients With Coronary Artery Disease: Effects of Expanded-Dose Simvastatin," Arteriosclerosis, Thrombosis, and Vascular Biology 21(9):1526-1530, Sep. 2001.

Hamilton, J.A., "Fatty Acid Interactions With Proteins: What X-Ray Crystal and NMR Solution Structures Tell Us," Progress in Lipid Research 43(3):177-199, May 2004.

Hasler-Rapacz, J., et al., "Elevated Concentrations of Plasma Lipids and Apolipoproteins B, C-III, and E Are Associated With the Progression of Coronary Artery Disease in Familial Hypercholesterolemic Swine," Arteriosclerosis, Thrombosis, and Vascular Biology 15(5):583-592, May 1995.

Heinecke, J.W., and A.J. Lusis, "Paraoxonase-Gene Polymorphisms Associated With Coronary Heart Disease: Support for the Oxidative Damage Hypothesis?" American Journal of Human Genetics 62(1):20-24, Jan. 1998.

Jarvik, G.P., et al., "Paraoxonase Activity, but Not Haplotype Utilizing the Linkage Disequilibrium Structure, Predicts Vascular Disease," Arteriosclerosis, Thrombosis, and Vascular Biology 23(8):1465-1471, Aug. 2003.

Karlsson, H., et al., "Lipoproteomics II: Mapping of Proteins in High-Density Lipoprotein Using Two-Dimensional Gel Electrophoresis and Mass Spectometry," Proteomics 5(5):1431-1445, Apr. 2005.

Khovidhunkit, W., et al., "Apolipoproteins A-IV and A-V Are Acute-Phase Proteins in Mouse HDL," Atherosclerosis 176(1)37-44, Sep. 2004.

Klos, K.L., et al., "Genome-Wide Linkage Analysis Reveals Evidence of Multiple Regions That Influence Variation in Plasma Lipid and Apolipoprotein Levels Associated With Risk of Coronary Heart Disease," Arteriosclerosis Thrombosis and Vascular Biology 21(6):971-978, Jun. 2001.

Kotite, L., et al., "Human apoC-IV: Isolation, Characterization, and Immunochemical Quantification in Plasma and Plasma Lipoproteins," Journal of Lipid Research 44(7):1387-1394, Jul. 2003.

Lachmann, P.J., et al., "Three Rat Monoclonal Antibodies to Human C3," Immunology 41(3):503-515, Nov. 1980.

Laine, P., et al., "Evidence for Complement Activation in Ruptured Coronary Plaques in Acute Myocardial Infarction," The American Journal of Cardiology 90(4):404-408, Aug. 2002.

Link, A.J., et al., "Direct Analysis of Protein Complexes Using Mass Spectrometry," Nature Biotechnology 17(7):676-682, Jul. 1999.

Linton, M.F., et al., "Prevention of Atherosclerosis in Apolipoprotein E-Deficient Mice by Bone Marrow Transplantation," Science 267(5200):1034-1037, Feb. 1995.

Mackness, M., et al., "Paraoxonase 1 Activity, Concentration and Genotype in Cardiovascular Disease," Current Opinion in Lipidology 15(4):399-404, Aug. 2004.

Mak, P.A., et al., "Regulated Expression of the Apolipoprotein E/C-I/C-IV/C-II Gene Cluster in Murine and Human Macrophages. A Critical Role for Nuclear Liver X Receptors $\alpha$ and $\beta$," Journal of Biological Chemistry 277(35):31900-31908, Aug. 2002.

Manzato, E., et al., "Levels and Physicochemical Properties of Lipoprotein Subclasses in Moderate Hypertriglyceridemia," Clinica Chimica Acta 219(1-2):57-65, Oct. 1993.

Marathe, G.K., et al., "Platelet-Activating Factor Acetylhydrolase, and Not Paraoxonase-1, Is the Oxidized Phospholipid Hydrolase of High Density Lipoprotein Particles," Journal of Biological Chemistry 278(6):3937-3947, Feb. 2003.

McPhaden, A.R., and K. Whaley, "Complement Biosynthesis by Mononuclear Phagocytes," Immunologic Research 12(3):213-232, Sep. 1993.

Mendez, A.J., et al., "Protein Kinase C as a Mediator of High Density Lipoprotein Receptor-Dependent Efflux of Intracellular Cholesterol," Journal of Biological Chemistry 266(16):10104-10111, Jun. 1991.

Muscari, A., et al., "Relationship Between Serum C3 Levels and Traditional Risk Factors for Myocardial Infarction," Acta Cardiologica 53(6):345-354, Dec. 1998.

Navab, M., et al., "Thematic Review Series: The Pathogenesis of Atherosclerosis. The Oxidation Hypothesis of Atherogenesis: The Role of Oxidized Phospholipids and HDL," Journal of Lipid Research 45(6):993-1007, Jun. 2004.

Nissen, S.E., et al., "Effect of Recombinant ApoA-I Milano on Coronary Atherosclerosis in Patients With Acute Coronary Syndromes: A Randomized Controlled Trial," Journal of the American Medical Association (JAMA) 290(17):2292-2300, Nov. 2003.

Oksjoki, R., et al., "Role of Complement Activation in Atherosclerosis," Current Opinion in Lipidology 14(5):477-482, Oct. 2003.

Olsen, J.V., and M. Mann, "Improved Peptide Identification in Proteomics by Two Consecutive Stages of Mass Spectrometric Fragmentation," Proceedings of the National Academy of Sciences (PNAS) 101(37):13417-13422, Sep. 2004.

Onat, A., et al., "Cross-Sectional Study of Complement C3 as a Coronary Risk Factor Among Men and Women," Clinical Science (London) 108(2):129-135, Feb. 2005.

Oram, J.F., "HDL Apolipoproteins and ABCA1: Partners in the Removal of Excess Cellular Cholesterol," Arteriosclerosis, Thrombosis, and Vascular Biology 23(5):720-727, May 2003.

Parthasarathy, S., et al., "High-Density Lipoprotein Inhibits the Oxidative Modification of Low-Density Lipoprotein," Biochimica et Biophysica Acta 1044(2):275-283, May 1990.

Qian, W.-J., et al., "Comparative Proteome Analyses of Human Plasma Following in Vivo Lipopolysaccharide Administration Using Multidimensional Separations Coupled With Tandem Mass Spectrometry," Proteomics 5(2):572-584, Feb. 2005.

Resing, K.A., "Proteomics for Cell Protein Expression Profiling," Journal of Investigative Dermatology 121(1):xi-xii, Jul. 2003.

Rocke, D.M., "Design and Analysis of Experiments With High Throughput Biological Assay Data," Seminars in Cell & Developmental Biology 15(6):703-713, Dec. 2004.

Rozek, L.S., et al., "The Correlation of Paraoxonase (PON1) Enzyme Activities With Plasma Lipid and Lipoprotein Levels Differs for Subjects With and Without Vascular Disease," Journal of Lipid Research 46(9):1888-1895, Sep. 2005.

Sacks, F.M., et al., "VLDL, Apolipoproteins B, CIII, and E, and Risk of Recurrent Coronary Events in the Cholesterol and Recurrent Events (CARE) Trial," Circulation 102(16):1886-1892, Oct. 2000.

Sackstein, R., and H.R. Colten, "Molecular Regulation of MHC Class III (C4 and Factor B) Gene Expression in Mouse Peritoneal Macrophages," Journal of Immunology 133(3)1618-1626, Sep. 1984.

Sampietro, T., et al., "Up Regulation of C3, C4, and Soluble Intercellular Adhesion Molecule-1 Co-Expresses With High Sensitivity C Reactive Protein in Familial Hypoalphalipoproteinaemia: Further Evidence of Inflammatory Activation," Heart 90(12):1438-1442, Dec. 2004.

Seifert, P.S., and G.K. Hansson, "Complement Receptors and Regulatory Proteins in Human Atherosclerotic Lesions," Arteriosclerosis, Thrombosis, and Vascular Biology 9(6):802-811, Nov.-Dec. 1989.

Shih, D.M., et al., "Combined Serum Paraoxonase Knockout/Apolipoprotein E Knockout Mice Exhibit Increased Lipoprotein Oxidation and Atherosclerosis," Journal of Biological Chemistry 275(23):17527-17535, Jun. 2000.

Shih, D.M., et al., "Mice Lacking Serum Paraoxonase Are Susceptible to Organophosphate Toxicity and Atherosclerosis," Nature 394(6690):284-287, Jul. 1998.

Stanley, B.A., et al., "Heart Disease, Clinical Proteomics and Mass Spectrometry," Disease Markers 20(3):167-178, Oct. 2004.

Stemmann, O., et al., "Dual Inhibition of Sister Chromatid Separation at Metaphase," Cell 107(6):715-726, Dec. 2001.

Tall, A.R., et al., "Regulation and Mechanisms of Macrophage Cholesterol Efflux," Journal of Clinical Investigation 110(7):899-904, Oct. 2002.

Vergès, B.L., et al., "Macrovascular Disease Is Associated With Increased Plasma Apolipoprotein A-IV Levels in NIDDM," Diabetes 46(1):125-132, Jan. 1997.

Washburn, M.P., et al., "Reproducibility of Quantitative Proteomic Analyses of Complex Biological Mixtures by Multidimensional Protein Identification Technology," Analytical Chemistry 75(19):5054-5061, Oct. 2003.

Wolfrum, C., et al., "Apolipoprotein M Is Required for preβ-HDL Formation and Cholesterol Efflux to HDL and Protects Against Atherosclerosis," Nature Medicine 11(4):418-422, Apr. 2005, 8 pages of supplemental online materials.

Yasojima, K., et al., "Complement Components, but Not Complement Inhibitors, Are Upregulated in Atherosclerotic Plaques," Arteriosclerosis, Thrombosis, and Vascular Biology 21(7):1214-1219, Jul. 2001.

Yasojima, K., et al., "Generation of C-Reactive Protein and Complement Components in Atherosclerotic Plaques," American Journal of Pathology 158(3):1039-1051, Mar. 2001.

Ylä-Herttuala, S., et al., "Rabbit and Human Atherosclerotic Lesions Contain IgG That Recognizes Epitopes of Oxidized LDL," Arteriosclerosis, Thrombosis, and Vascular Biology 14(1):32-40, Jan. 1994.

Yu, C.Y., and C.C. Whitacre, "Sex, MHC and Complement C4 in Autoimmune Diseases," TRENDS in Immunology 25(12):694-699, Dec. 2004.

SEQUENCE LISTING

<160> NUMBER OF SEQ ID NOS: 175

<210> SEQ ID NO 1
<211> LENGTH: 127
<212> TYPE: PRT
<213> ORGANISM: Homo Sapiens

<400> SEQUENCE: 1

```
Met Ser Leu Leu Arg Asn Arg Leu Gln Ala Leu Pro Ala Leu Cys Leu
1               5                   10                  15

Cys Val Leu Val Leu Ala Cys Ile Gly Ala Cys Gln Pro Glu Ala Gln
                20                  25                  30

Glu Gly Thr Leu Ser Pro Pro Lys Leu Lys Met Ser Arg Trp Ser
            35                  40                  45

Leu Val Arg Gly Arg Met Lys Glu Leu Leu Glu Thr Val Val Asn Arg
50                  55                  60

Thr Arg Asp Gly Trp Gln Trp Phe Trp Ser Pro Ser Thr Phe Arg Gly
65                  70                  75                  80

Phe Met Gln Thr Tyr Tyr Asp Asp His Leu Arg Asp Leu Gly Pro Leu
                85                  90                  95

Thr Lys Ala Trp Phe Leu Glu Ser Lys Asp Ser Leu Leu Lys Lys Thr
                100                 105                 110

His Ser Leu Cys Pro Arg Leu Val Cys Gly Asp Lys Asp Gln Gly
            115                 120                 125
```

<210> SEQ ID NO 2
<211> LENGTH: 354
<212> TYPE: PRT
<213> ORGANISM: Homo Sapiens

<400> SEQUENCE: 2

```
Ala Lys Leu Ile Ala Leu Thr Leu Leu Gly Met Gly Leu Ala Leu Phe
1               5                   10                  15

Arg Asn His Gln Ser Ser Tyr Gln Thr Arg Leu Asn Ala Leu Arg Glu
                20                  25                  30

Val Gln Pro Val Glu Leu Pro Asn Cys Asn Leu Val Lys Gly Ile Glu
            35                  40                  45

Thr Gly Ser Glu Asp Met Glu Ile Leu Pro Asn Gly Leu Ala Phe Ile
50                  55                  60

Ser Ser Gly Leu Lys Tyr Pro Gly Ile Lys Ser Phe Asn Pro Asn Ser
65                  70                  75                  80

Pro Gly Lys Ile Leu Leu Met Asp Leu Asn Glu Glu Asp Pro Thr Val
                85                  90                  95

Leu Glu Leu Gly Ile Thr Gly Ser Lys Phe Asp Val Ser Ser Phe Asn
                100                 105                 110

Pro His Gly Ile Ser Thr Phe Thr Asp Glu Asp Asn Ala Met Tyr Leu
            115                 120                 125

Leu Val Val Asn His Pro Asp Ala Lys Ser Thr Val Glu Leu Phe Lys
130                 135                 140

Phe Gln Glu Glu Glu Lys Ser Leu Leu His Leu Lys Thr Ile Arg His
145                 150                 155                 160

Lys Leu Leu Pro Asn Leu Asn Asp Ile Val Ala Val Gly Pro Glu His
                165                 170                 175

Phe Tyr Gly Thr Asn Asp His Tyr Phe Leu Asp Pro Tyr Leu Gln Ser
                180                 185                 190

Trp Glu Met Tyr Leu Gly Leu Ala Trp Ser Tyr Val Val Tyr Tyr Ser
            195                 200                 205

Pro Ser Glu Val Arg Val Val Ala Glu Gly Phe Asp Phe Ala Asn Gly
210                 215                 220

Ile Asn Ile Ser Pro Asp Gly Lys Tyr Val Tyr Ile Ala Glu Leu Leu
225                 230                 235                 240

Ala His Lys Ile His Val Tyr Glu Lys His Ala Asn Trp Thr Leu Thr
                245                 250                 255
```

```
Pro Leu Lys Ser Leu Asp Phe Asn Thr Leu Val Asp Asn Ile Ser Val
            260                 265                 270

Asp Pro Glu Thr Gly Asp Leu Trp Val Gly Cys His Pro Asn Gly Met
            275                 280                 285

Lys Ile Phe Phe Tyr Asp Ser Glu Asn Pro Pro Ala Ser Glu Val Leu
            290                 295                 300

Arg Ile Gln Asn Ile Leu Thr Glu Glu Pro Lys Val Thr Gln Val Tyr
305                 310                 315                 320

Ala Glu Asn Gly Thr Val Leu Gln Gly Ser Thr Val Ala Ser Val Tyr
                325                 330                 335

Lys Gly Lys Leu Leu Ile Gly Thr Val Phe His Lys Ala Leu Tyr Cys
                340                 345                 350

Glu Leu

<210> SEQ ID NO 3
<211> LENGTH: 1663
<212> TYPE: PRT
<213> ORGANISM: Homo Sapiens

<400> SEQUENCE: 3

Met Gly Pro Thr Ser Gly Pro Ser Leu Leu Leu Leu Leu Thr His Leu
1               5                   10                  15

Leu Pro Leu Ala Leu Gly Ser Pro Met Tyr Ser Ile Ile Thr Pro Asn
                20                  25                  30

Ile Leu Arg Leu Glu Ser Glu Glu Thr Met Val Leu Glu Ala His Asp
            35                  40                  45

Ala Gln Gly Asp Val Pro Val Thr Val Thr Val His Asp Phe Pro Gly
50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95

Lys Ser Glu Lys Gly Arg Asn Lys Phe Val Thr Val Gln Ala Thr Phe
            100                 105                 110

Gly Thr Gln Val Val Glu Lys Val Val Leu Val Ser Leu Gln Ser Gly
        115                 120                 125

Tyr Leu Phe Ile Gln Thr Asp Lys Thr Ile Tyr Thr Pro Gly Ser Thr
    130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
        195                 200                 205

Tyr Tyr Glu Asn Ser Pro Gln Gln Val Phe Ser Thr Glu Phe Glu Val
    210                 215                 220

Lys Glu Tyr Val Leu Pro Ser Phe Glu Val Ile Val Glu Pro Thr Glu
225                 230                 235                 240

Lys Phe Tyr Tyr Ile Tyr Asn Glu Lys Gly Leu Glu Val Thr Ile Thr
                245                 250                 255

Ala Arg Phe Leu Tyr Gly Lys Lys Val Glu Gly Thr Ala Phe Val Ile
            260                 265                 270

Phe Gly Ile Gln Asp Gly Glu Gln Arg Ile Ser Leu Pro Glu Ser Leu
```

```
                275                 280                 285
Lys Arg Ile Pro Ile Glu Asp Gly Ser Gly Glu Val Val Leu Ser Arg
    290                 295                 300
Lys Val Leu Leu Asp Gly Val Gln Asn Leu Arg Ala Glu Asp Leu Val
305                 310                 315                 320
Gly Lys Ser Leu Tyr Val Ser Ala Thr Val Ile Leu His Ser Gly Ser
                325                 330                 335
Asp Met Val Gln Ala Glu Arg Ser Gly Ile Pro Ile Val Thr Ser Pro
                340                 345                 350
Tyr Gln Ile His Phe Thr Lys Thr Pro Lys Tyr Phe Lys Pro Gly Met
                355                 360                 365
Pro Phe Asp Leu Met Val Phe Val Thr Asn Pro Asp Gly Ser Pro Ala
            370                 375                 380
Tyr Arg Val Pro Val Ala Val Gln Gly Glu Asp Thr Val Gln Ser Leu
385                 390                 395                 400
Thr Gln Gly Asp Gly Val Ala Lys Leu Ser Ile Asn Thr His Pro Ser
                405                 410                 415
Gln Lys Pro Leu Ser Ile Thr Val Arg Thr Lys Lys Gln Glu Leu Ser
            420                 425                 430
Glu Ala Glu Gln Ala Thr Arg Thr Met Gln Ala Leu Pro Tyr Ser Thr
        435                 440                 445
Val Gly Asn Ser Asn Asn Tyr Leu His Leu Ser Val Leu Arg Thr Glu
    450                 455                 460
Leu Arg Pro Gly Glu Thr Leu Asn Val Asn Phe Leu Leu Arg Met Asp
465                 470                 475                 480
Arg Ala His Glu Ala Lys Ile Arg Tyr Tyr Thr Tyr Leu Ile Met Asn
                485                 490                 495
Lys Gly Arg Leu Leu Lys Ala Gly Arg Gln Val Arg Glu Pro Gly Gln
                500                 505                 510
Asp Leu Val Val Leu Pro Leu Ser Ile Thr Thr Asp Phe Ile Pro Ser
            515                 520                 525
Phe Arg Leu Val Ala Tyr Tyr Thr Leu Ile Gly Ala Ser Gly Gln Arg
        530                 535                 540
Glu Val Val Ala Asp Ser Val Trp Val Asp Val Lys Asp Ser Cys Val
545                 550                 555                 560
Gly Ser Leu Val Val Lys Ser Gly Gln Ser Glu Asp Arg Gln Pro Val
                565                 570                 575
Pro Gly Gln Gln Met Thr Leu Lys Ile Glu Gly Asp His Gly Ala Arg
                580                 585                 590
Val Val Leu Val Ala Val Asp Lys Gly Val Phe Val Leu Asn Lys Lys
                595                 600                 605
Asn Lys Leu Thr Gln Ser Lys Ile Trp Asp Val Val Glu Lys Ala Asp
        610                 615                 620
Ile Gly Cys Thr Pro Gly Ser Gly Lys Asp Tyr Ala Gly Val Phe Ser
625                 630                 635                 640
Asp Ala Gly Leu Thr Phe Thr Ser Ser Ser Gly Gln Gln Thr Ala Gln
                645                 650                 655
Arg Ala Glu Leu Gln Cys Pro Gln Pro Ala Ala Arg Arg Arg Arg Ser
                660                 665                 670
Val Gln Leu Thr Glu Lys Arg Met Asp Lys Val Gly Lys Tyr Pro Lys
            675                 680                 685
Glu Leu Arg Lys Cys Cys Glu Asp Gly Met Arg Glu Asn Pro Met Arg
        690                 695                 700
```

-continued

```
Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
            725                 730                 735

Gln His Ala Arg Ala Ser His Leu Gly Leu Ala Arg Ser Asn Leu Asp
            740                 745                 750

Glu Asp Ile Ile Ala Glu Asn Ile Val Ser Arg Ser Glu Phe Pro
            755                 760                 765

Glu Ser Trp Leu Trp Asn Val Glu Asp Leu Lys Glu Pro Pro Lys Asn
        770                 775                 780

Gly Ile Ser Thr Lys Leu Met Asn Ile Phe Leu Lys Asp Ser Ile Thr
785                 790                 795                 800

Thr Trp Glu Ile Leu Ala Val Ser Met Ser Asp Lys Lys Gly Ile Cys
                805                 810                 815

Val Ala Asp Pro Phe Glu Val Thr Val Met Gln Asp Phe Phe Ile Asp
            820                 825                 830

Leu Arg Leu Pro Tyr Ser Val Arg Asn Glu Gln Val Glu Ile Arg
            835                 840                 845

Ala Val Leu Tyr Asn Tyr Arg Gln Asn Gln Glu Leu Lys Val Arg Val
850                 855                 860

Glu Leu Leu His Asn Pro Ala Phe Cys Ser Leu Ala Thr Thr Lys Arg
865                 870                 875                 880

Arg His Gln Gln Thr Val Thr Ile Pro Pro Lys Ser Ser Leu Ser Val
                885                 890                 895

Pro Tyr Val Ile Val Pro Leu Lys Thr Gly Leu Gln Glu Val Glu Val
            900                 905                 910

Lys Ala Ala Val Tyr His His Phe Ile Ser Asp Gly Val Arg Lys Ser
            915                 920                 925

Leu Lys Val Val Pro Glu Gly Ile Arg Met Asn Lys Thr Val Ala Val
        930                 935                 940

Arg Thr Leu Asp Pro Glu Arg Leu Gly Arg Glu Gly Val Gln Lys Glu
945                 950                 955                 960

Asp Ile Pro Pro Ala Asp Leu Ser Asp Gln Val Pro Asp Thr Glu Ser
                965                 970                 975

Glu Thr Arg Ile Leu Leu Gln Gly Thr Pro Val Ala Gln Met Thr Glu
            980                 985                 990

Asp Ala Val Asp Ala Glu Arg Leu  Lys His Leu Ile Val  Thr Pro Ser
        995                 1000                1005

Gly Cys  Gly Glu Gln Asn Met  Ile Gly Met Thr Pro  Thr Val Ile
    1010                1015                1020

Ala Val His Tyr Leu Asp Glu  Thr Glu Gln Trp Glu  Lys Phe Gly
    1025                1030                1035

Leu Glu Lys Arg Gln Gly Ala  Leu Glu Leu Ile Lys  Lys Gly Tyr
    1040                1045                1050

Thr Gln Gln Leu Ala Phe Arg  Gln Pro Ser Ser Ala  Phe Ala Ala
    1055                1060                1065

Phe Val Lys Arg Ala Pro Ser  Thr Trp Leu Thr Ala  Tyr Val Val
    1070                1075                1080

Lys Val Phe Ser Leu Ala Val  Asn Leu Ile Ala Ile  Asp Ser Gln
    1085                1090                1095

Val Leu Cys Gly Ala Val Lys  Trp Leu Ile Leu Glu  Lys Gln Lys
    1100                1105                1110

Pro Asp Gly Val Phe Gln Glu  Asp Ala Pro Val Ile  His Gln Glu
    1115                1120                1125
```

```
Met Ile Gly Gly Leu Arg Asn  Asn Asn Glu Lys Asp  Met Ala Leu
    1130            1135                1140

Thr Ala Phe Val Leu Ile Ser  Leu Gln Glu Ala Lys  Asp Ile Cys
    1145            1150                1155

Glu Glu Gln Val Asn Ser Leu  Pro Gly Ser Ile Thr  Lys Ala Gly
    1160            1165                1170

Asp Phe Leu Glu Ala Asn Tyr  Met Asn Leu Gln Arg  Ser Tyr Thr
    1175            1180                1185

Val Ala Ile Ala Gly Tyr Ala  Leu Ala Gln Met Gly  Arg Leu Lys
    1190            1195                1200

Gly Pro Leu Leu Asn Lys Phe  Leu Thr Thr Ala Lys  Asp Lys Asn
    1205            1210                1215

Arg Trp Glu Asp Pro Gly Lys  Gln Leu Tyr Asn Val  Glu Ala Thr
    1220            1225                1230

Ser Tyr Ala Leu Leu Ala Leu  Leu Gln Leu Lys Asp  Phe Asp Phe
    1235            1240                1245

Val Pro Pro Val Val Arg Trp  Leu Asn Glu Gln Arg  Tyr Tyr Gly
    1250            1255                1260

Gly Gly Tyr Gly Ser Thr Gln  Ala Thr Phe Met Val  Phe Gln Ala
    1265            1270                1275

Leu Ala Gln Tyr Gln Lys Asp  Ala Pro Asp His Gln  Glu Leu Asn
    1280            1285                1290

Leu Asp Val Ser Leu Gln Leu  Pro Ser Arg Ser Ser  Lys Ile Thr
    1295            1300                1305

His Arg Ile His Trp Glu Ser  Ala Ser Leu Leu Arg  Ser Glu Glu
    1310            1315                1320

Thr Lys Glu Asn Glu Gly Phe  Thr Val Thr Ala Glu  Gly Lys Gly
    1325            1330                1335

Gln Gly Thr Leu Ser Val Val  Thr Met Tyr His Ala  Lys Ala Lys
    1340            1345                1350

Asp Gln Leu Thr Cys Asn Lys  Phe Asp Leu Lys Val  Thr Ile Lys
    1355            1360                1365

Pro Ala Pro Glu Thr Glu Lys  Arg Pro Gln Asp Ala  Lys Asn Thr
    1370            1375                1380

Met Ile Leu Glu Ile Cys Thr  Arg Tyr Arg Gly Asp  Gln Asp Ala
    1385            1390                1395

Thr Met Ser Ile Leu Asp Ile  Ser Met Met Thr Gly  Phe Ala Pro
    1400            1405                1410

Asp Thr Asp Asp Leu Lys Gln  Leu Ala Asn Gly Val  Asp Arg Tyr
    1415            1420                1425

Ile Ser Lys Tyr Glu Leu Asp  Lys Ala Phe Ser Asp  Arg Asn Thr
    1430            1435                1440

Leu Ile Ile Tyr Leu Asp Lys  Val Ser His Ser Glu  Asp Asp Cys
    1445            1450                1455

Leu Ala Phe Lys Val His Gln  Tyr Phe Asn Val Glu  Leu Ile Gln
    1460            1465                1470

Pro Gly Ala Val Lys Val Tyr  Ala Tyr Tyr Asn Leu  Glu Glu Ser
    1475            1480                1485

Cys Thr Arg Phe Tyr His Pro  Glu Lys Glu Asp Gly  Lys Leu Asn
    1490            1495                1500

Lys Leu Cys Arg Asp Glu Leu  Cys Arg Cys Ala Glu  Glu Asn Cys
    1505            1510                1515

Phe Ile Gln Lys Ser Asp Asp  Lys Val Thr Leu Glu  Glu Arg Leu
```

-continued

```
             1520              1525              1530

Asp Lys Ala Cys Glu Pro Gly Val Asp Tyr Val Tyr Lys Thr Arg
    1535              1540              1545

Leu Val Lys Val Gln Leu Ser Asn Asp Phe Asp Glu Tyr Ile Met
    1550              1555              1560

Ala Ile Glu Gln Thr Ile Lys Ser Gly Ser Asp Glu Val Gln Val
    1565              1570              1575

Gly Gln Gln Arg Thr Phe Ile Ser Pro Ile Lys Cys Arg Glu Ala
    1580              1585              1590

Leu Lys Leu Glu Glu Lys Lys His Tyr Leu Met Trp Gly Leu Ser
    1595              1600              1605

Ser Asp Phe Trp Gly Glu Lys Pro Asn Leu Ser Tyr Ile Ile Gly
    1610              1615              1620

Lys Asp Thr Trp Val Glu His Trp Pro Glu Glu Asp Glu Cys Gln
    1625              1630              1635

Asp Glu Glu Asn Gln Lys Gln Cys Gln Asp Leu Gly Ala Phe Thr
    1640              1645              1650

Glu Ser Met Val Val Phe Gly Cys Pro Asn
    1655              1660

<210> SEQ ID NO 4
<211> LENGTH: 396
<212> TYPE: PRT
<213> ORGANISM: Homo Sapiens

<400> SEQUENCE: 4

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
        35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Thr Pro Tyr
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
```

```
                225                 230                 235                 240
Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Gln Gln Gln
    370                 375                 380

Gln Glu Gln Val Gln Met Leu Ala Pro Leu Glu Ser
385                 390                 395

<210> SEQ ID NO 5
<211> LENGTH: 317
<212> TYPE: PRT
<213> ORGANISM: Homo Sapiens

<400> SEQUENCE: 5

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
```

```
                    210                 215                 220

Ala Gln Ala Trp Gly Glu Arg Leu Arg Ala Arg Met Glu Met Gly
225                 230                 235                 240

Ser Arg Thr Arg Asp Arg Leu Asp Glu Val Lys Glu Gln Val Ala Glu
                    245                 250                 255

Val Arg Ala Lys Leu Glu Glu Gln Ala Gln Gln Ile Arg Leu Gln Ala
                260                 265                 270

Glu Ala Phe Gln Ala Arg Leu Lys Ser Trp Phe Glu Pro Leu Val Glu
                275                 280                 285

Asp Met Gln Arg Gln Trp Ala Gly Leu Val Glu Lys Val Gln Ala Ala
290                 295                 300

Val Gly Thr Ser Ala Ala Pro Val Pro Ser Asp Asn His
305                 310                 315

<210> SEQ ID NO 6
<211> LENGTH: 398
<212> TYPE: PRT
<213> ORGANISM: Homo Sapiens

<400> SEQUENCE: 6

Met Glu Gly Ala Ala Leu Leu Arg Val Ser Val Leu Cys Ile Trp Met
1               5                   10                  15

Ser Ala Leu Phe Leu Gly Val Gly Val Arg Ala Glu Glu Ala Gly Ala
                20                  25                  30

Arg Val Gln Gln Asn Val Pro Ser Gly Thr Asp Thr Gly Asp Pro Gln
            35                  40                  45

Ser Lys Pro Leu Gly Asp Trp Ala Ala Gly Thr Met Asp Pro Glu Ser
50                  55                  60

Ser Ile Phe Ile Glu Asp Ala Ile Lys Tyr Phe Lys Glu Lys Val Ser
65                  70                  75                  80

Thr Gln Asn Leu Leu Leu Leu Thr Asp Asn Glu Ala Trp Asn Gly
                85                  90                  95

Phe Val Ala Ala Ala Glu Leu Pro Arg Asn Glu Ala Asp Glu Leu Arg
            100                 105                 110

Lys Ala Leu Asp Asn Leu Ala Arg Gln Met Ile Met Lys Asp Lys Asn
        115                 120                 125

Trp His Asp Lys Gly Gln Gln Tyr Arg Asn Trp Phe Leu Lys Glu Phe
    130                 135                 140

Pro Arg Leu Lys Ser Lys Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
        195                 200                 205

Glu Pro Gly Met Glu Leu Gly Ile Thr Ala Ala Leu Thr Gly Ile Thr
    210                 215                 220

Ser Ser Thr Ile Asp Tyr Gly Lys Lys Trp Trp Thr Gln Ala Gln Ala
225                 230                 235                 240

His Asp Leu Val Ile Lys Ser Leu Asp Lys Lys Glu Val Lys Glu
                245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
```

```
                275                 280                 285
Ala Arg Ala Asn Leu Gln Ser Val Pro His Ala Ser Arg Pro
290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Ser Phe Phe Leu Val Leu Asp Val Val Tyr Leu
            340                 345                 350

Val Tyr Glu Ser Lys His Leu His Glu Gly Ala Lys Ser Glu Thr Ala
        355                 360                 365

Glu Glu Leu Lys Lys Val Ala Gln Glu Leu Glu Lys Leu Asn Ile
370                 375                 380

Leu Asn Asn Asn Tyr Lys Ile Leu Gln Ala Asp Gln Glu Leu
385                 390                 395

<210> SEQ ID NO 7
<211> LENGTH: 1744
<212> TYPE: PRT
<213> ORGANISM: Homo Sapiens

<400> SEQUENCE: 7

Met Arg Leu Leu Trp Gly Leu Ile Trp Ala Ser Ser Phe Phe Thr Leu
1               5                   10                  15

Ser Leu Gln Lys Pro Arg Leu Leu Phe Ser Pro Ser Val Val His
            20                  25                  30

Leu Gly Val Pro Leu Ser Val Gly Val Gln Leu Gln Asp Val Pro Arg
        35                  40                  45

Gly Gln Val Val Lys Gly Ser Val Phe Leu Arg Asn Pro Ser Arg Asn
    50                  55                  60

Asn Val Pro Cys Ser Pro Lys Val Asp Phe Thr Leu Ser Ser Glu Arg
65                  70                  75                  80

Asp Phe Ala Leu Leu Ser Leu Gln Val Pro Leu Lys Asp Ala Lys Ser
                85                  90                  95

Cys Gly Leu His Gln Leu Leu Arg Gly Pro Glu Val Gln Leu Val Ala
            100                 105                 110

His Ser Pro Trp Leu Lys Asp Ser Leu Ser Arg Thr Thr Asn Ile Gln
        115                 120                 125

Gly Ile Asn Leu Leu Phe Ser Ser Arg Arg Gly His Leu Phe Leu Gln
    130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
            180                 185                 190

Met Pro Ser Ser Ile Phe Gln Asp Asp Phe Val Ile Pro Asp Ile Ser
        195                 200                 205

Glu Pro Gly Thr Trp Lys Ile Ser Ala Arg Phe Ser Asp Gly Leu Glu
    210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
```

```
                    260                 265                 270
Gly Lys Pro Val Gln Gly Val Ala Tyr Val Arg Phe Gly Leu Leu Asp
            275                 280                 285
Glu Asp Gly Lys Lys Thr Phe Phe Arg Gly Leu Glu Ser Gln Thr Lys
            290                 295                 300
Leu Val Asn Gly Gln Ser His Ile Ser Leu Ser Lys Ala Glu Phe Gln
305                 310                 315                 320
Asp Ala Leu Glu Lys Leu Asn Met Gly Ile Thr Asp Leu Gln Gly Leu
                325                 330                 335
Arg Leu Tyr Val Ala Ala Ile Ile Glu Ser Pro Gly Gly Glu Met
                340                 345                 350
Glu Glu Ala Glu Leu Thr Ser Trp Tyr Phe Val Ser Ser Pro Phe Ser
                355                 360                 365
Leu Asp Leu Ser Lys Thr Lys Arg His Leu Val Pro Gly Ala Pro Phe
                370                 375                 380
Leu Leu Gln Ala Leu Val Arg Glu Met Ser Gly Ser Pro Ala Ser Gly
385                 390                 395                 400
Ile Pro Val Lys Val Ser Ala Thr Val Ser Ser Pro Gly Ser Val Pro
                405                 410                 415
Glu Val Gln Asp Ile Gln Gln Asn Thr Asp Gly Ser Gly Gln Val Ser
                420                 425                 430
Ile Pro Ile Ile Ile Pro Gln Thr Ile Ser Glu Leu Gln Leu Ser Val
                435                 440                 445
Ser Ala Gly Ser Pro His Pro Ala Ile Ala Arg Leu Thr Val Ala Ala
                450                 455                 460
Pro Pro Ser Gly Gly Pro Gly Phe Leu Ser Ile Glu Arg Pro Asp Ser
465                 470                 475                 480
Arg Pro Pro Arg Val Gly Asp Thr Leu Asn Leu Asn Leu Arg Ala Val
                    485                 490                 495
Gly Ser Gly Ala Thr Phe Ser His Tyr Tyr Tyr Met Ile Leu Ser Arg
                    500                 505                 510
Gly Gln Ile Val Phe Met Asn Arg Glu Pro Lys Arg Thr Leu Thr Ser
                515                 520                 525
Val Ser Val Phe Val Asp His His Leu Ala Pro Ser Phe Tyr Phe Val
                530                 535                 540
Ala Phe Tyr Tyr His Gly Asp His Pro Val Ala Asn Ser Leu Arg Val
545                 550                 555                 560
Asp Val Gln Ala Gly Ala Cys Glu Gly Lys Leu Glu Leu Ser Val Asp
                    565                 570                 575
Gly Ala Lys Gln Tyr Arg Asn Gly Glu Ser Val Lys Leu His Leu Glu
                580                 585                 590
Thr Asp Ser Leu Ala Leu Val Ala Leu Gly Ala Leu Asp Thr Ala Leu
                595                 600                 605
Tyr Ala Ala Gly Ser Lys Ser His Lys Pro Leu Asn Met Gly Lys Val
                610                 615                 620
Phe Glu Ala Met Asn Ser Tyr Asp Leu Gly Cys Gly Pro Gly Gly Gly
625                 630                 635                 640
Asp Ser Ala Leu Gln Val Phe Gln Ala Ala Gly Leu Ala Phe Ser Asp
                    645                 650                 655
Gly Asp Gln Trp Thr Leu Ser Arg Lys Arg Leu Ser Cys Pro Lys Glu
                660                 665                 670
Lys Thr Thr Arg Lys Lys Arg Asn Val Asn Phe Gln Lys Ala Ile Asn
                675                 680                 685
```

-continued

Glu Lys Leu Gly Gln Tyr Ala Ser Pro Thr Ala Lys Arg Cys Cys Gln
690                 695                 700

Asp Gly Val Thr Arg Leu Pro Met Met Arg Ser Cys Glu Gln Arg Ala
705                 710                 715                 720

Ala Arg Val Gln Gln Pro Asp Cys Arg Glu Pro Phe Leu Ser Cys Cys
            725                 730                 735

Gln Phe Ala Glu Ser Leu Arg Lys Lys Ser Arg Asp Lys Gly Gln Ala
            740                 745                 750

Gly Leu Gln Arg Ala Leu Glu Ile Leu Gln Glu Asp Leu Ile Asp
            755                 760                 765

Glu Asp Asp Ile Pro Val Arg Ser Phe Pro Glu Asn Trp Leu Trp
770                 775                 780

Arg Val Glu Thr Val Asp Arg Phe Gln Ile Leu Thr Leu Trp Leu Pro
785                 790                 795                 800

Asp Ser Leu Thr Thr Trp Glu Ile His Gly Leu Ser Leu Ser Lys Thr
                805                 810                 815

Lys Gly Leu Cys Val Ala Thr Pro Val Gln Leu Arg Val Phe Arg Glu
            820                 825                 830

Phe His Leu His Leu Arg Leu Pro Met Ser Val Arg Arg Phe Glu Gln
            835                 840                 845

Leu Glu Leu Arg Pro Val Leu Tyr Asn Tyr Leu Asp Lys Asn Leu Thr
850                 855                 860

Val Ser Val His Val Ser Pro Val Glu Gly Leu Cys Leu Ala Gly Gly
865                 870                 875                 880

Gly Gly Leu Ala Gln Gln Val Leu Val Pro Ala Gly Ser Ala Arg Pro
            885                 890                 895

Val Ala Phe Ser Val Val Pro Thr Ala Ala Thr Ala Val Ser Leu Lys
            900                 905                 910

Val Val Ala Arg Gly Ser Phe Glu Phe Pro Val Gly Asp Ala Val Ser
            915                 920                 925

Lys Val Leu Gln Ile Glu Lys Glu Gly Ala Ile His Arg Glu Glu Leu
            930                 935                 940

Val Tyr Glu Leu Asn Pro Leu Asp His Arg Gly Arg Thr Leu Glu Ile
945                 950                 955                 960

Pro Gly Asn Ser Asp Pro Asn Met Ile Pro Asp Gly Asp Phe Asn Ser
                965                 970                 975

Tyr Val Arg Val Thr Ala Ser Asp Pro Leu Asp Thr Leu Gly Ser Glu
                980                 985                 990

Gly Ala Leu Ser Pro Gly Gly Val Ala Ser Leu Leu Arg Leu Pro Arg
            995                 1000                1005

Gly Cys Gly Glu Gln Thr Met Ile Tyr Leu Ala Pro Thr Leu Ala
    1010                1015                1020

Ala Ser Arg Tyr Leu Asp Lys Thr Glu Gln Trp Ser Thr Leu Pro
    1025                1030                1035

Pro Glu Thr Lys Asp His Ala Val Asp Leu Ile Gln Lys Gly Tyr
    1040                1045                1050

Met Arg Ile Gln Gln Phe Arg Lys Ala Asp Gly Ser Tyr Ala Ala
    1055                1060                1065

Trp Leu Ser Arg Gly Ser Ser Thr Trp Leu Thr Ala Phe Val Leu
    1070                1075                1080

Lys Val Leu Ser Leu Ala Gln Glu Gln Val Gly Gly Ser Pro Glu
    1085                1090                1095

Lys Leu Gln Glu Thr Ser Asn Trp Leu Leu Ser Gln Gln Gln Ala
    1100                1105                1110

```
Asp Gly Ser Phe Gln Asp Leu Ser Pro Val Ile His Arg Ser Met
    1115                1120                1125

Gln Gly Gly Leu Val Gly Asn Asp Glu Thr Val Ala Leu Thr Ala
    1130                1135                1140

Phe Val Thr Ile Ala Leu His His Gly Leu Ala Val Phe Gln Asp
    1145                1150                1155

Glu Gly Ala Glu Pro Leu Lys Gln Arg Val Glu Ala Ser Ile Ser
    1160                1165                1170

Lys Ala Ser Ser Phe Leu Gly Glu Lys Ala Ser Ala Gly Leu Leu
    1175                1180                1185

Gly Ala His Ala Ala Ala Ile Thr Ala Tyr Ala Leu Thr Leu Thr
    1190                1195                1200

Lys Ala Pro Ala Asp Leu Arg Gly Val Ala His Asn Asn Leu Met
    1205                1210                1215

Ala Met Ala Gln Glu Thr Gly Asp Asn Leu Tyr Trp Gly Ser Val
    1220                1225                1230

Thr Gly Ser Gln Ser Asn Ala Val Ser Pro Thr Pro Ala Pro Arg
    1235                1240                1245

Asn Pro Ser Asp Pro Met Pro Gln Ala Pro Ala Leu Trp Ile Glu
    1250                1255                1260

Thr Thr Ala Tyr Ala Leu Leu His Leu Leu Leu His Glu Gly Lys
    1265                1270                1275

Ala Glu Met Ala Asp Gln Ala Ala Ala Trp Leu Thr Arg Gln Gly
    1280                1285                1290

Ser Phe Gln Gly Gly Phe Arg Ser Thr Gln Asp Thr Val Ile Ala
    1295                1300                1305

Leu Asp Ala Leu Ser Ala Tyr Trp Ile Ala Ser His Thr Thr Glu
    1310                1315                1320

Glu Arg Gly Leu Asn Val Thr Leu Ser Ser Thr Gly Arg Asn Gly
    1325                1330                1335

Phe Lys Ser His Ala Leu Gln Leu Asn Asn Arg Gln Ile Arg Gly
    1340                1345                1350

Leu Glu Glu Glu Leu Gln Phe Ser Leu Gly Ser Lys Ile Asn Val
    1355                1360                1365

Lys Val Gly Gly Asn Ser Lys Gly Thr Leu Lys Val Leu Arg Thr
    1370                1375                1380

Tyr Asn Val Leu Asp Met Lys Asn Thr Thr Cys Gln Asp Leu Gln
    1385                1390                1395

Ile Glu Val Thr Val Lys Gly His Val Glu Tyr Thr Met Glu Ala
    1400                1405                1410

Asn Glu Asp Tyr Glu Asp Tyr Glu Tyr Asp Glu Leu Pro Ala Lys
    1415                1420                1425

Asp Asp Pro Asp Ala Pro Leu Gln Pro Val Thr Pro Leu Gln Leu
    1430                1435                1440

Phe Glu Gly Arg Arg Asn Arg Arg Arg Glu Ala Pro Lys Val
    1445                1450                1455

Val Glu Glu Gln Glu Ser Arg Val His Tyr Thr Val Cys Ile Trp
    1460                1465                1470

Arg Asn Gly Lys Val Gly Leu Ser Gly Met Ala Ile Ala Asp Val
    1475                1480                1485

Thr Leu Leu Ser Gly Phe His Ala Leu Arg Ala Asp Leu Glu Lys
    1490                1495                1500

Leu Thr Ser Leu Ser Asp Arg Tyr Val Ser His Phe Glu Thr Glu
```

```
                    1505                1510                1515

Gly Pro His Val Leu Leu Tyr Phe Asp Ser Val Pro Thr Ser Arg
        1520                1525                1530

Glu Cys Val Gly Phe Glu Ala Val Gln Glu Val Pro Val Gly Leu
    1535                1540                1545

Val Gln Pro Ala Ser Ala Thr Leu Tyr Asp Tyr Tyr Asn Pro Glu
1550                1555                1560

Arg Arg Cys Ser Val Phe Tyr Gly Ala Pro Ser Lys Ser Arg Leu
1565                1570                1575

Leu Ala Thr Leu Cys Ser Ala Glu Val Cys Gln Cys Ala Glu Gly
    1580                1585                1590

Lys Cys Pro Arg Gln Arg Ala Leu Glu Arg Gly Leu Gln Asp
    1595                1600                1605

Glu Asp Gly Tyr Arg Met Lys Phe Ala Cys Tyr Tyr Pro Arg Val
    1610                1615                1620

Glu Tyr Gly Phe Gln Val Lys Val Leu Arg Glu Asp Ser Arg Ala
    1625                1630                1635

Ala Phe Arg Leu Phe Glu Thr Lys Ile Thr Gln Val Leu His Phe
    1640                1645                1650

Thr Lys Asp Val Lys Ala Ala Ala Asn Gln Met Arg Asn Phe Leu
    1655                1660                1665

Val Arg Ala Ser Cys Arg Leu Arg Leu Glu Pro Gly Lys Glu Tyr
    1670                1675                1680

Leu Ile Met Gly Leu Asp Gly Ala Thr Tyr Asp Leu Glu Gly His
    1685                1690                1695

Pro Gln Tyr Leu Leu Asp Ser Asn Ser Trp Ile Glu Glu Met Pro
    1700                1705                1710

Ser Glu Arg Leu Cys Arg Ser Thr Arg Gln Arg Ala Ala Cys Ala
    1715                1720                1725

Gln Leu Asn Asp Phe Leu Gln Glu Tyr Gly Thr Gln Gly Cys Gln
    1730                1735                1740

Val

<210> SEQ ID NO 8
<211> LENGTH: 127
<212> TYPE: PRT
<213> ORGANISM: Homo Sapiens

<400> SEQUENCE: 8

Ser Gly Arg Gly Lys Gln Gly Gly Lys Ala Arg Ala Lys Ala Lys Thr
1               5                   10                  15

Arg Ser Ser Arg Ala Gly Leu Gln Phe Pro Val Gly Arg Val His Arg
                20                  25                  30

Leu Leu Arg Lys Gly Asn Tyr Ala Glu Arg Val Gly Ala Gly Ala Pro
            35                  40                  45

Val Tyr Leu Ala Ala Val Leu Glu Tyr Leu Thr Ala Glu Ile Leu Glu
    50                  55                  60

Leu Ala Gly Asn Ala Ala Arg Asp Asn Lys Lys Thr Arg Ile Ile Pro
65                  70                  75                  80

Arg His Leu Gln Leu Ala Ile Arg Asn Asp Glu Glu Leu Asn Lys Leu
                85                  90                  95

Leu Gly Lys Val Thr Ile Ala Gln Gly Gly Val Leu Pro Asn Ile Gln
            100                 105                 110

Ala Val Leu Leu Pro Lys Lys Thr Glu Ser His His Lys Thr Lys
        115                 120                 125
```

<210> SEQ ID NO 9
<211> LENGTH: 101
<212> TYPE: PRT
<213> ORGANISM: Homo Sapiens

<400> SEQUENCE: 9

```
Met Gly Thr Arg Leu Leu Pro Ala Leu Phe Leu Val Leu Leu Val Leu
1               5                   10                  15

Gly Phe Glu Val Gln Gly Thr Gln Gln Pro Gln Gln Asp Glu Met Pro
            20                  25                  30

Ser Pro Thr Phe Leu Thr Gln Val Lys Glu Ser Leu Ser Ser Tyr Trp
        35                  40                  45

Glu Ser Ala Lys Thr Ala Ala Gln Asn Leu Tyr Glu Lys Thr Tyr Leu
    50                  55                  60

Pro Ala Val Asp Glu Lys Leu Arg Asp Leu Tyr Ser Lys Ser Thr Ala
65                  70                  75                  80

Ala Met Ser Thr Tyr Thr Gly Ile Phe Thr Asp Gln Val Leu Ser Val
                85                  90                  95

Leu Lys Gly Glu Glu
            100
```

<210> SEQ ID NO 10
<211> LENGTH: 188
<212> TYPE: PRT
<213> ORGANISM: Homo Sapiens

<400> SEQUENCE: 10

```
Met Phe His Gln Ile Trp Ala Ala Leu Leu Tyr Phe Tyr Gly Ile Ile
1               5                   10                  15

Leu Asn Ser Ile Tyr Gln Cys Pro Glu His Ser Gln Leu Thr Thr Leu
            20                  25                  30

Gly Val Asp Gly Lys Glu Phe Pro Glu Val His Leu Gly Gln Trp Tyr
        35                  40                  45

Phe Ile Ala Gly Ala Ala Pro Thr Lys Glu Glu Leu Ala Thr Phe Asp
    50                  55                  60

Pro Val Asp Asn Ile Val Phe Asn Met Ala Ala Gly Ser Ala Pro Met
65                  70                  75                  80

Gln Leu His Leu Arg Ala Thr Ile Arg Met Lys Asp Gly Leu Cys Val
                85                  90                  95

Pro Arg Lys Trp Ile Tyr His Leu Thr Glu Gly Ser Thr Asp Leu Arg
            100                 105                 110

Thr Glu Gly Arg Pro Asp Met Lys Thr Glu Leu Phe Ser Ser Ser Cys
        115                 120                 125

Pro Gly Gly Ile Met Leu Asn Glu Thr Gly Gln Gly Tyr Gln Arg Phe
    130                 135                 140

Leu Leu Tyr Asn Arg Ser Pro His Pro Glu Lys Cys Val Glu Glu
145                 150                 155                 160

Phe Lys Ser Leu Thr Ser Cys Leu Asp Ser Lys Ala Phe Leu Leu Thr
                165                 170                 175

Pro Arg Asn Gln Glu Ala Cys Glu Leu Ser Asn Asn
            180                 185
```

<210> SEQ ID NO 11
<211> LENGTH: 353
<212> TYPE: PRT
<213> ORGANISM: Homo Sapiens

<400> SEQUENCE: 11

```
Arg Leu Gly Arg Glu Gly Val Gln Lys Glu Asp Ile Pro Pro Ala Asp
1               5                   10                  15

Leu Ser Asp Gln Val Pro Asp Thr Glu Ser Glu Thr Arg Ile Leu Leu
            20                  25                  30

Gln Gly Thr Pro Val Ala Gln Met Thr Glu Asp Ala Val Asp Ala Glu
        35                  40                  45

Arg Leu Lys His Leu Ile Val Thr Pro Ser Gly Cys Gly Glu Gln Asn
    50                  55                  60

Met Ile Gly Met Thr Pro Thr Val Ile Ala Val His Tyr Leu Asp Glu
65                  70                  75                  80

Thr Glu Gln Trp Glu Lys Phe Gly Leu Glu Lys Arg Gln Gly Ala Leu
                85                  90                  95

Glu Leu Ile Lys Lys Gly Tyr Thr Gln Gln Leu Ala Phe Arg Gln Pro
            100                 105                 110

Ser Ser Ala Phe Ala Ala Phe Val Lys Arg Ala Pro Ser Thr Trp Leu
        115                 120                 125

Thr Ala Tyr Val Val Lys Val Phe Ser Leu Ala Val Asn Leu Ile Ala
    130                 135                 140

Ile Asp Ser Gln Val Leu Cys Gly Ala Val Lys Trp Leu Ile Leu Glu
145                 150                 155                 160

Lys Gln Lys Pro Asp Gly Val Phe Gln Glu Asp Ala Pro Val Ile His
                165                 170                 175

Gln Glu Met Ile Gly Gly Leu Arg Asn Asn Asn Glu Lys Asp Met Ala
            180                 185                 190

Leu Thr Ala Phe Val Leu Ile Ser Leu Gln Glu Ala Lys Asp Ile Cys
        195                 200                 205

Glu Glu Gln Val Asn Ser Leu Pro Gly Ser Ile Thr Lys Ala Gly Asp
    210                 215                 220

Phe Leu Glu Ala Asn Tyr Met Asn Leu Gln Arg Ser Tyr Thr Val Ala
225                 230                 235                 240

Ile Ala Gly Tyr Ala Leu Ala Gln Met Gly Arg Leu Lys Gly Pro Leu
                245                 250                 255

Leu Asn Lys Phe Leu Thr Thr Ala Lys Asp Lys Asn Arg Trp Glu Asp
            260                 265                 270

Pro Gly Lys Gln Leu Tyr Asn Val Glu Ala Thr Ser Tyr Ala Leu Leu
        275                 280                 285

Ala Leu Leu Gln Leu Lys Asp Phe Asp Phe Val Pro Pro Val Val Arg
    290                 295                 300

Trp Leu Asn Glu Gln Arg Tyr Tyr Gly Gly Gly Tyr Gly Ser Thr Gln
305                 310                 315                 320

Ala Thr Phe Met Val Phe Gln Ala Leu Ala Gln Tyr Gln Lys Asp Ala
                325                 330                 335

Pro Asp His Gln Glu Leu Asn Leu Asp Val Ser Leu Gln Leu Pro Ser
            340                 345                 350

Arg
```

<210> SEQ ID NO 12
<211> LENGTH: 478
<212> TYPE: PRT
<213> ORGANISM: Homo Sapiens

<400> SEQUENCE: 12

```
Met Ala Pro Leu Arg Pro Leu Leu Ile Leu Ala Leu Leu Ala Trp Val
1               5                   10                  15
```

```
Ala Leu Ala Asp Gln Glu Ser Cys Lys Gly Arg Cys Thr Glu Gly Phe
                20                  25                  30

Asn Val Asp Lys Lys Cys Gln Cys Asp Glu Leu Cys Ser Tyr Tyr Gln
            35                  40                  45

Ser Cys Cys Thr Asp Tyr Thr Ala Glu Cys Lys Pro Gln Val Thr Arg
50                  55                  60

Gly Asp Val Phe Thr Met Pro Glu Asp Glu Tyr Thr Val Tyr Asp Asp
65                  70                  75                  80

Gly Glu Glu Lys Asn Asn Ala Thr Val His Glu Gln Val Gly Gly Pro
                85                  90                  95

Ser Leu Thr Ser Asp Leu Gln Ala Gln Ser Lys Gly Asn Pro Glu Gln
            100                 105                 110

Thr Pro Val Leu Lys Pro Glu Glu Ala Pro Ala Pro Glu Val Gly
            115                 120                 125

Ala Ser Lys Pro Glu Gly Ile Asp Ser Arg Pro Glu Thr Leu His Pro
        130                 135                 140

Gly Arg Pro Gln Pro Pro Ala Glu Glu Glu Leu Cys Ser Gly Lys Pro
145                 150                 155                 160

Phe Asp Ala Phe Thr Asp Leu Lys Asn Gly Ser Leu Phe Ala Phe Arg
                165                 170                 175

Gly Gln Tyr Cys Tyr Glu Leu Asp Glu Lys Ala Val Arg Pro Gly Tyr
            180                 185                 190

Pro Lys Leu Ile Arg Asp Val Trp Gly Ile Glu Gly Pro Ile Asp Ala
        195                 200                 205

Ala Phe Thr Arg Ile Asn Cys Gln Gly Lys Thr Tyr Leu Phe Lys Gly
        210                 215                 220

Ser Gln Tyr Trp Arg Phe Glu Asp Gly Val Leu Asp Pro Asp Tyr Pro
225                 230                 235                 240

Arg Asn Ile Ser Asp Gly Phe Asp Gly Ile Pro Asp Asn Val Asp Ala
                245                 250                 255

Ala Leu Ala Leu Pro Ala His Ser Tyr Ser Gly Arg Glu Arg Val Tyr
            260                 265                 270

Phe Phe Lys Gly Lys Gln Tyr Trp Glu Tyr Gln Phe Gln His Gln Pro
        275                 280                 285

Ser Gln Glu Glu Cys Glu Gly Ser Ser Leu Ser Ala Val Phe Glu His
290                 295                 300

Phe Ala Met Met Gln Arg Asp Ser Trp Glu Asp Ile Phe Glu Leu Leu
305                 310                 315                 320

Phe Trp Gly Arg Thr Ser Ala Gly Thr Arg Gln Pro Gln Phe Ile Ser
                325                 330                 335

Arg Asp Trp His Gly Val Pro Gly Gln Val Asp Ala Ala Met Ala Gly
            340                 345                 350

Arg Ile Tyr Ile Ser Gly Met Ala Pro Arg Pro Ser Leu Ala Lys Lys
        355                 360                 365

Gln Arg Phe Arg His Arg Asn Arg Lys Gly Tyr Arg Ser Gln Arg Gly
        370                 375                 380

His Ser Arg Gly Arg Asn Gln Asn Ser Arg Arg Pro Ser Arg Ala Thr
385                 390                 395                 400

Trp Leu Ser Leu Phe Ser Ser Glu Glu Ser Asn Leu Gly Ala Asn Asn
                405                 410                 415

Tyr Asp Asp Tyr Arg Met Asp Trp Leu Val Pro Ala Thr Cys Glu Pro
            420                 425                 430

Ile Gln Ser Val Phe Phe Phe Ser Gly Asp Lys Tyr Tyr Arg Val Asn
```

```
                435                 440                 445
Leu Arg Thr Arg Arg Val Asp Thr Val Asp Pro Pro Tyr Pro Arg Ser
450                 455                 460

Ile Ala Gln Tyr Trp Leu Gly Cys Pro Ala Pro Gly His Leu
465                 470                 475

<210> SEQ ID NO 13
<211> LENGTH: 348
<212> TYPE: PRT
<213> ORGANISM: Homo Sapiens

<400> SEQUENCE: 13

Met Ser Asp Leu Gly Ala Val Ile Ser Leu Leu Trp Gly Arg Gln
1               5                   10                  15

Leu Phe Ala Leu Tyr Ser Gly Asn Asp Val Thr Asp Ile Ser Asp
                20                  25                  30

Arg Phe Pro Lys Pro Pro Glu Ile Ala Asn Gly Tyr Val Glu His Leu
                35                  40                  45

Phe Arg Tyr Gln Cys Lys Asn Tyr Tyr Arg Leu Arg Thr Glu Gly Asp
50                  55                  60

Gly Val Tyr Thr Leu Asn Asp Lys Lys Gln Trp Ile Asn Lys Ala Val
65                  70                  75                  80

Gly Asp Lys Leu Pro Glu Cys Glu Ala Val Cys Gly Lys Pro Lys Asn
                85                  90                  95

Pro Ala Asn Pro Val Gln Arg Ile Leu Gly Gly His Leu Asp Ala Lys
                100                 105                 110

Gly Ser Phe Pro Trp Gln Ala Lys Met Val Ser His His Asn Leu Thr
                115                 120                 125

Thr Gly Ala Thr Leu Ile Asn Glu Gln Trp Leu Leu Thr Thr Ala Lys
                130                 135                 140

Asn Leu Phe Leu Asn His Ser Glu Asn Ala Thr Ala Lys Asp Ile Ala
145                 150                 155                 160

Pro Thr Leu Thr Leu Tyr Val Gly Lys Lys Gln Leu Val Glu Ile Glu
                165                 170                 175

Lys Val Val Leu His Pro Asn Tyr His Gln Val Asp Ile Gly Leu Ile
                180                 185                 190

Lys Leu Lys Gln Lys Val Leu Val Asn Glu Arg Val Met Pro Ile Cys
                195                 200                 205

Leu Pro Ser Lys Asn Tyr Ala Glu Val Gly Arg Val Gly Tyr Val Ser
210                 215                 220

Gly Trp Gly Gln Ser Asp Asn Phe Lys Leu Thr Asp His Leu Lys Tyr
225                 230                 235                 240

Val Met Leu Pro Val Ala Asp Gln Tyr Asp Cys Ile Thr His Tyr Glu
                245                 250                 255

Gly Ser Thr Cys Pro Lys Trp Lys Ala Pro Lys Ser Pro Val Gly Val
                260                 265                 270

Gln Pro Ile Leu Asn Glu His Thr Phe Cys Val Gly Met Ser Lys Tyr
                275                 280                 285

Gln Glu Asp Thr Cys Tyr Gly Asp Ala Gly Ser Ala Phe Ala Val His
                290                 295                 300

Asp Leu Glu Glu Asp Thr Trp Tyr Ala Ala Gly Ile Leu Ser Phe Asp
305                 310                 315                 320

Lys Ser Cys Ala Val Ala Glu Tyr Gly Val Tyr Val Lys Val Thr Ser
                325                 330                 335

Ile Gln Asp Trp Val Gln Lys Thr Ile Ala Glu Asn
```

<210> SEQ ID NO 14
<211> LENGTH: 449
<212> TYPE: PRT
<213> ORGANISM: Homo Sapiens

<400> SEQUENCE: 14

Met Met Lys Thr Leu Leu Phe Val Gly Leu Leu Thr Trp Glu
1               5                   10                  15

Ser Gly Gln Val Leu Gly Asp Gln Thr Val Ser Asp Asn Glu Leu Gln
                20                  25                  30

Glu Met Ser Asn Gln Gly Ser Lys Tyr Val Asn Lys Glu Ile Gln Asn
            35                  40                  45

Ala Val Asn Gly Val Lys Gln Ile Lys Thr Leu Ile Glu Lys Thr Asn
        50                  55                  60

Glu Glu Arg Lys Thr Leu Leu Ser Asn Leu Glu Glu Ala Lys Lys Lys
65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
        115                 120                 125

Cys Arg Ser Gly Ser Gly Leu Val Gly Arg Gln Leu Glu Glu Phe Leu
130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
        195                 200                 205

Phe Ser Leu Pro His Arg Arg Pro His Phe Phe Pro Lys Ser Arg
210                 215                 220

Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
            260                 265                 270

Glu Phe Ile Arg Glu Gly Asp Asp Arg Thr Val Cys Arg Glu Ile
        275                 280                 285

Arg His Asn Ser Thr Gly Cys Leu Arg Met Lys Asp Gln Cys Asp Lys
290                 295                 300

Cys Arg Glu Ile Leu Ser Val Asp Cys Ser Thr Asn Asn Pro Ser Gln
305                 310                 315                 320

Ala Lys Leu Arg Arg Glu Leu Asp Glu Ser Leu Gln Val Ala Glu Arg
                325                 330                 335

Leu Thr Arg Lys Tyr Asn Glu Leu Leu Lys Ser Tyr Gln Trp Lys Met
            340                 345                 350

Leu Asn Thr Ser Ser Leu Leu Glu Gln Leu Asn Glu Gln Phe Asn Trp
        355                 360                 365

Val Ser Arg Leu Ala Asn Leu Thr Gln Gly Glu Asp Gln Tyr Tyr Leu

```
              370                 375                 380
Arg Val Thr Thr Val Ala Ser His Thr Ser Asp Ser Asp Val Pro Ser
385                 390                 395                 400

Gly Val Thr Glu Val Val Lys Leu Phe Asp Ser Asp Pro Ile Thr
                405                 410                 415

Val Thr Val Pro Val Glu Val Ser Arg Lys Asn Pro Lys Phe Met Glu
                420                 425                 430

Thr Val Ala Glu Lys Ala Leu Gln Glu Tyr Arg Lys Lys His Arg Glu
                435                 440                 445

Glu

<210> SEQ ID NO 15
<211> LENGTH: 1744
<212> TYPE: PRT
<213> ORGANISM: Homo Sapiens

<400> SEQUENCE: 15

Met Arg Leu Leu Trp Gly Leu Ile Trp Ala Ser Ser Phe Phe Thr Leu
1               5                   10                  15

Ser Leu Gln Lys Pro Arg Leu Leu Leu Phe Ser Pro Ser Val Val His
                20                  25                  30

Leu Gly Val Pro Leu Ser Val Gly Val Gln Leu Gln Asp Val Pro Arg
                35                  40                  45

Gly Gln Val Val Lys Gly Ser Val Phe Leu Arg Asn Pro Ser Arg Asn
            50                  55                  60

Asn Val Pro Cys Ser Pro Lys Val Asp Phe Thr Leu Ser Ser Glu Arg
65              70                  75                  80

Asp Phe Ala Leu Leu Ser Leu Gln Val Pro Leu Lys Asp Ala Lys Ser
                85                  90                  95

Cys Gly Leu His Gln Leu Leu Arg Gly Pro Glu Val Gln Leu Val Ala
                100                 105                 110

His Ser Pro Trp Leu Lys Asp Ser Leu Ser Arg Thr Thr Asn Ile Gln
                115                 120                 125

Gly Ile Asn Leu Leu Phe Ser Ser Arg Arg Gly His Leu Phe Leu Gln
            130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
                180                 185                 190

Met Pro Ser Ser Ile Phe Gln Asp Asp Phe Val Ile Pro Asp Ile Ser
                195                 200                 205

Glu Pro Gly Thr Trp Lys Ile Ser Ala Arg Phe Ser Asp Gly Leu Glu
            210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
                260                 265                 270

Gly Lys Pro Val Gln Gly Val Ala Tyr Val Arg Phe Gly Leu Leu Asp
            275                 280                 285

Glu Asp Gly Lys Lys Thr Phe Phe Arg Gly Leu Glu Ser Gln Thr Lys
290                 295                 300
```

-continued

```
Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
                325                 330                 335

Arg Leu Tyr Val Ala Ala Ile Ile Glu Ser Pro Gly Gly Glu Met
            340                 345                 350

Glu Glu Ala Glu Leu Thr Ser Trp Tyr Phe Val Ser Ser Pro Phe Ser
                355                 360                 365

Leu Asp Leu Ser Lys Thr Lys Arg His Leu Val Pro Gly Ala Pro Phe
        370                 375                 380

Leu Leu Gln Ala Leu Val Arg Glu Met Ser Gly Ser Pro Ala Ser Gly
385                 390                 395                 400

Ile Pro Val Lys Val Ser Ala Thr Val Ser Ser Pro Gly Ser Val Pro
                405                 410                 415

Glu Val Gln Asp Ile Gln Gln Asn Thr Asp Gly Ser Gly Gln Val Ser
                420                 425                 430

Ile Pro Ile Ile Ile Pro Gln Thr Ile Ser Glu Leu Gln Leu Ser Val
            435                 440                 445

Ser Ala Gly Ser Pro His Pro Ala Ile Ala Arg Leu Thr Val Ala Ala
450                 455                 460

Pro Pro Ser Gly Gly Pro Gly Phe Leu Ser Ile Glu Arg Pro Asp Ser
465                 470                 475                 480

Arg Pro Pro Arg Val Gly Asp Thr Leu Asn Leu Asn Leu Arg Ala Val
                485                 490                 495

Gly Ser Gly Ala Thr Phe Ser His Tyr Tyr Tyr Met Ile Leu Ser Arg
                500                 505                 510

Gly Gln Ile Val Phe Met Asn Arg Glu Pro Lys Arg Thr Leu Thr Ser
            515                 520                 525

Val Ser Val Phe Val Asp His His Leu Ala Pro Ser Phe Tyr Phe Val
530                 535                 540

Ala Phe Tyr Tyr His Gly Asp His Pro Val Ala Asn Ser Leu Arg Val
545                 550                 555                 560

Asp Val Gln Ala Gly Ala Cys Glu Gly Lys Leu Glu Leu Ser Val Asp
                565                 570                 575

Gly Ala Lys Gln Tyr Arg Asn Gly Glu Ser Val Lys Leu His Leu Glu
                580                 585                 590

Thr Asp Ser Leu Ala Leu Val Ala Leu Gly Ala Leu Asp Thr Ala Leu
            595                 600                 605

Tyr Ala Ala Gly Ser Lys Ser His Lys Pro Leu Asn Met Gly Lys Val
610                 615                 620

Phe Glu Ala Met Asn Ser Tyr Asp Leu Gly Cys Gly Pro Gly Gly Gly
625                 630                 635                 640

Asp Ser Ala Leu Gln Val Phe Gln Ala Ala Gly Leu Ala Phe Ser Asp
                645                 650                 655

Gly Asp Gln Trp Thr Leu Ser Arg Lys Arg Leu Ser Cys Pro Lys Glu
            660                 665                 670

Lys Thr Thr Arg Lys Lys Arg Asn Val Asn Phe Gln Lys Ala Ile Asn
        675                 680                 685

Glu Lys Leu Gly Gln Tyr Ala Ser Pro Thr Ala Lys Arg Cys Cys Gln
            690                 695                 700

Asp Gly Val Thr Arg Leu Pro Met Met Arg Ser Cys Glu Gln Arg Ala
705                 710                 715                 720

Ala Arg Val Gln Gln Pro Asp Cys Arg Glu Pro Phe Leu Ser Cys Cys
```

```
                725                 730                 735
Gln Phe Ala Glu Ser Leu Arg Lys Lys Ser Arg Asp Lys Gly Gln Ala
            740                 745                 750

Gly Leu Gln Arg Ala Leu Glu Ile Leu Gln Glu Glu Asp Leu Ile Asp
            755                 760                 765

Glu Asp Asp Ile Pro Val Arg Ser Phe Phe Pro Glu Asn Trp Leu Trp
770                 775                 780

Arg Val Glu Thr Val Asp Arg Phe Gln Ile Leu Thr Leu Trp Leu Pro
785                 790                 795                 800

Asp Ser Leu Thr Thr Trp Glu Ile His Gly Leu Ser Leu Ser Lys Thr
                805                 810                 815

Lys Gly Leu Cys Val Ala Thr Pro Val Gln Leu Arg Val Phe Arg Glu
            820                 825                 830

Phe His Leu His Leu Arg Leu Pro Met Ser Val Arg Arg Phe Glu Gln
            835                 840                 845

Leu Glu Leu Arg Pro Val Leu Tyr Asn Tyr Leu Asp Lys Asn Leu Thr
            850                 855                 860

Val Ser Val His Val Ser Pro Val Glu Gly Leu Cys Leu Ala Gly Gly
865                 870                 875                 880

Gly Gly Leu Ala Gln Gln Val Leu Val Pro Ala Gly Ser Ala Arg Pro
                885                 890                 895

Val Ala Phe Ser Val Val Pro Thr Ala Ala Ala Val Ser Leu Lys
            900                 905                 910

Val Val Ala Arg Gly Ser Phe Glu Phe Pro Val Gly Asp Ala Val Ser
            915                 920                 925

Lys Val Leu Gln Ile Glu Lys Glu Gly Ala Ile His Arg Glu Glu Leu
930                 935                 940

Val Tyr Glu Leu Asn Pro Leu Asp His Arg Gly Arg Thr Leu Glu Ile
945                 950                 955                 960

Pro Gly Asn Ser Asp Pro Asn Met Ile Pro Asp Gly Asp Phe Asn Ser
                965                 970                 975

Tyr Val Arg Val Thr Ala Ser Asp Pro Leu Asp Thr Leu Gly Ser Glu
            980                 985                 990

Gly Ala Leu Ser Pro Gly Gly Val Ala Ser Leu Leu Arg Leu Pro Arg
            995                1000                1005

Gly Cys Gly Glu Gln Thr Met Ile Tyr Leu Ala Pro Thr Leu Ala
        1010                1015                1020

Ala Ser Arg Tyr Leu Asp Lys Thr Glu Gln Trp Ser Thr Leu Pro
        1025                1030                1035

Pro Glu Thr Lys Asp His Ala Val Asp Leu Ile Gln Lys Gly Tyr
        1040                1045                1050

Met Arg Ile Gln Gln Phe Arg Lys Ala Asp Gly Ser Tyr Ala Ala
        1055                1060                1065

Trp Leu Ser Arg Asp Ser Ser Thr Trp Leu Thr Ala Phe Val Leu
        1070                1075                1080

Lys Val Leu Ser Leu Ala Gln Glu Gln Val Gly Gly Ser Pro Glu
        1085                1090                1095

Lys Leu Gln Glu Thr Ser Asn Trp Leu Leu Ser Gln Gln Gln Ala
        1100                1105                1110

Asp Gly Ser Phe Gln Asp Pro Cys Pro Val Leu Asp Arg Ser Met
        1115                1120                1125

Gln Gly Gly Leu Val Gly Asn Asp Glu Thr Val Ala Leu Thr Ala
        1130                1135                1140
```

-continued

Phe Val Thr Ile Ala Leu His His Gly Leu Ala Val Phe Gln Asp
1145                1150                1155

Glu Gly Ala Glu Pro Leu Lys Gln Arg Val Glu Ala Ser Ile Ser
1160                1165                1170

Lys Ala Asn Ser Phe Leu Gly Glu Lys Ala Ser Ala Gly Leu Leu
1175                1180                1185

Gly Ala His Ala Ala Ala Ile Thr Ala Tyr Ala Leu Ser Leu Thr
1190                1195                1200

Lys Ala Pro Val Asp Leu Leu Gly Val Ala His Asn Asn Leu Met
1205                1210                1215

Ala Met Ala Gln Glu Thr Gly Asp Asn Leu Tyr Trp Gly Ser Val
1220                1225                1230

Thr Gly Ser Gln Ser Asn Ala Val Ser Pro Thr Pro Ala Pro Arg
1235                1240                1245

Asn Pro Ser Asp Pro Met Pro Gln Ala Pro Ala Leu Trp Ile Glu
1250                1255                1260

Thr Thr Ala Tyr Ala Leu Leu His Leu Leu Leu His Glu Gly Lys
1265                1270                1275

Ala Glu Met Ala Asp Gln Ala Ser Ala Trp Leu Thr Arg Gln Gly
1280                1285                1290

Ser Phe Gln Gly Gly Phe Arg Ser Thr Gln Asp Thr Val Ile Ala
1295                1300                1305

Leu Asp Ala Leu Ser Ala Tyr Trp Ile Ala Ser His Thr Thr Glu
1310                1315                1320

Glu Arg Gly Leu Asn Val Thr Leu Ser Ser Thr Gly Arg Asn Gly
1325                1330                1335

Phe Lys Ser His Ala Leu Gln Leu Asn Asn Arg Gln Ile Arg Gly
1340                1345                1350

Leu Glu Glu Glu Leu Gln Phe Ser Leu Gly Ser Lys Ile Asn Val
1355                1360                1365

Lys Val Gly Gly Asn Ser Lys Gly Thr Leu Lys Val Leu Arg Thr
1370                1375                1380

Tyr Asn Val Leu Asp Met Lys Asn Thr Thr Cys Gln Asp Leu Gln
1385                1390                1395

Ile Glu Val Thr Val Lys Gly His Val Glu Tyr Thr Met Glu Ala
1400                1405                1410

Asn Glu Asp Tyr Glu Asp Tyr Glu Tyr Asp Glu Leu Pro Ala Lys
1415                1420                1425

Asp Asp Pro Asp Ala Pro Leu Gln Pro Val Thr Pro Leu Gln Leu
1430                1435                1440

Phe Glu Gly Arg Arg Asn Arg Arg Arg Glu Ala Pro Lys Val
1445                1450                1455

Val Glu Glu Gln Glu Ser Arg Val His Tyr Thr Val Cys Ile Trp
1460                1465                1470

Arg Asn Gly Lys Val Gly Leu Ser Gly Met Ala Ile Ala Asp Val
1475                1480                1485

Thr Leu Leu Ser Gly Phe His Ala Leu Arg Ala Asp Leu Glu Lys
1490                1495                1500

Leu Thr Ser Leu Ser Asp Arg Tyr Val Ser His Phe Glu Thr Glu
1505                1510                1515

Gly Pro His Val Leu Leu Tyr Phe Asp Ser Val Pro Thr Ser Arg
1520                1525                1530

Glu Cys Val Gly Phe Glu Ala Val Gln Glu Val Pro Val Gly Leu
1535                1540                1545

```
Val Gln Pro Ala Ser Ala Thr Leu Tyr Asp Tyr Tyr Asn Pro Glu
    1550                1555                1560

Arg Arg Cys Ser Val Phe Tyr Gly Ala Pro Ser Lys Ser Arg Leu
    1565                1570                1575

Leu Ala Thr Leu Cys Ser Ala Glu Val Cys Gln Cys Ala Glu Gly
    1580                1585                1590

Lys Cys Pro Arg Gln Arg Arg Ala Leu Glu Arg Gly Leu Gln Asp
    1595                1600                1605

Glu Asp Gly Tyr Arg Met Lys Phe Ala Cys Tyr Tyr Pro Arg Val
    1610                1615                1620

Glu Tyr Gly Phe Gln Val Lys Val Leu Arg Glu Asp Ser Arg Ala
    1625                1630                1635

Ala Phe Arg Leu Phe Glu Thr Lys Ile Thr Gln Val Leu His Phe
    1640                1645                1650

Thr Lys Asp Val Lys Ala Ala Asn Gln Met Arg Asn Phe Leu
    1655                1660                1665

Val Arg Ala Ser Cys Arg Leu Arg Leu Glu Pro Gly Lys Glu Tyr
    1670                1675                1680

Leu Ile Met Gly Leu Asp Gly Ala Thr Tyr Asp Leu Glu Gly His
    1685                1690                1695

Pro Gln Tyr Leu Leu Asp Ser Asn Ser Trp Ile Glu Glu Met Pro
    1700                1705                1710

Ser Glu Arg Leu Cys Arg Ser Thr Arg Gln Arg Ala Ala Cys Ala
    1715                1720                1725

Gln Leu Asn Asp Phe Leu Gln Glu Tyr Gly Thr Gln Gly Cys Gln
    1730                1735                1740

Val

<210> SEQ ID NO 16
<211> LENGTH: 12
<212> TYPE: PRT
<213> ORGANISM: Homo Sapiens

<400> SEQUENCE: 16

Gly Phe Met Gln Thr Tyr Tyr Asp Asp His Leu Arg
1               5                   10

<210> SEQ ID NO 17
<211> LENGTH: 13
<212> TYPE: PRT
<213> ORGANISM: Homo Sapiens

<400> SEQUENCE: 17

Asp Gly Trp Gln Trp Phe Trp Ser Pro Ser Thr Phe Arg
1               5                   10

<210> SEQ ID NO 18
<211> LENGTH: 13
<212> TYPE: PRT
<213> ORGANISM: Homo Sapiens

<400> SEQUENCE: 18

Thr His Ser Leu Cys Pro Arg Leu Val Cys Gly Asp Lys
1               5                   10

<210> SEQ ID NO 19
<211> LENGTH: 9
<212> TYPE: PRT
<213> ORGANISM: Homo Sapiens
```

-continued

<400> SEQUENCE: 19

Glu Leu Leu Glu Thr Val Val Asn Arg
1               5

<210> SEQ ID NO 20
<211> LENGTH: 7
<212> TYPE: PRT
<213> ORGANISM: Homo Sapiens

<400> SEQUENCE: 20

Ala Trp Phe Leu Glu Ser Lys
1               5

<210> SEQ ID NO 21
<211> LENGTH: 7
<212> TYPE: PRT
<213> ORGANISM: Homo Sapiens

<400> SEQUENCE: 21

Asp Leu Gly Pro Leu Thr Lys
1               5

<210> SEQ ID NO 22
<211> LENGTH: 6
<212> TYPE: PRT
<213> ORGANISM: Homo Sapiens

<400> SEQUENCE: 22

Asp Ser Leu Leu Lys Lys
1               5

<210> SEQ ID NO 23
<211> LENGTH: 11
<212> TYPE: PRT
<213> ORGANISM: Homo Sapiens

<400> SEQUENCE: 23

Tyr Val Tyr Ile Ala Glu Leu Leu Ala His Lys
1               5                   10

<210> SEQ ID NO 24
<211> LENGTH: 17
<212> TYPE: PRT
<213> ORGANISM: Homo Sapiens

<400> SEQUENCE: 24

Tyr Val Tyr Ile Ala Glu Leu Leu Ala His Lys Ile His Val Tyr Glu
1               5                   10                  15

Lys

<210> SEQ ID NO 25
<211> LENGTH: 19
<212> TYPE: PRT
<213> ORGANISM: Homo Sapiens

<400> SEQUENCE: 25

Val Val Ala Glu Gly Phe Asp Phe Ala Asn Gly Ile Asn Ile Ser Pro
1               5                   10                  15

Asp Gly Lys

<210> SEQ ID NO 26
<211> LENGTH: 17
<212> TYPE: PRT

-continued

<213> ORGANISM: Homo Sapiens

<400> SEQUENCE: 26

Ala Lys Leu Ile Ala Leu Thr Leu Leu Gly Met Gly Leu Ala Leu Phe
1               5                   10                  15
Arg

<210> SEQ ID NO 27
<211> LENGTH: 14
<212> TYPE: PRT
<213> ORGANISM: Homo Sapiens

<400> SEQUENCE: 27

Asn His Gln Ser Ser Tyr Gln Thr Arg Leu Asn Ala Leu Arg
1               5                   10

<210> SEQ ID NO 28
<211> LENGTH: 13
<212> TYPE: PRT
<213> ORGANISM: Homo Sapiens

<400> SEQUENCE: 28

Ser Thr Val Glu Leu Phe Lys Phe Gln Glu Glu Glu Lys
1               5                   10

<210> SEQ ID NO 29
<211> LENGTH: 14
<212> TYPE: PRT
<213> ORGANISM: Homo Sapiens

<400> SEQUENCE: 29

Glu Val Gln Pro Val Glu Leu Pro Asn Cys Asn Leu Val Lys
1               5                   10

<210> SEQ ID NO 30
<211> LENGTH: 11
<212> TYPE: PRT
<213> ORGANISM: Homo Sapiens

<400> SEQUENCE: 30

Gly Lys Leu Leu Ile Gly Thr Val Phe His Lys
1               5                   10

<210> SEQ ID NO 31
<211> LENGTH: 10
<212> TYPE: PRT
<213> ORGANISM: Homo Sapiens

<400> SEQUENCE: 31

His Ala Asn Trp Thr Leu Thr Pro Leu Lys
1               5                   10

<210> SEQ ID NO 32
<211> LENGTH: 6
<212> TYPE: PRT
<213> ORGANISM: Homo Sapiens

<400> SEQUENCE: 32

Ala Leu Tyr Cys Glu Leu
1               5

<210> SEQ ID NO 33
<211> LENGTH: 6
<212> TYPE: PRT
<213> ORGANISM: Homo Sapiens

<400> SEQUENCE: 33

Ser Leu Leu His Leu Lys
1               5

<210> SEQ ID NO 34
<211> LENGTH: 20
<212> TYPE: PRT
<213> ORGANISM: Homo Sapiens

<400> SEQUENCE: 34

Ile Leu Leu Gln Gly Thr Pro Val Ala Gln Met Thr Glu Asp Ala Val
1               5                   10                  15

Asp Ala Glu Arg
            20

<210> SEQ ID NO 35
<211> LENGTH: 14
<212> TYPE: PRT
<213> ORGANISM: Homo Sapiens

<400> SEQUENCE: 35

Ala Gly Asp Phe Leu Glu Ala Asn Tyr Met Asn Leu Gln Arg
1               5                   10

<210> SEQ ID NO 36
<211> LENGTH: 10
<212> TYPE: PRT
<213> ORGANISM: Homo Sapiens

<400> SEQUENCE: 36

Asp Phe Asp Phe Val Pro Pro Val Val Arg
1               5                   10

<210> SEQ ID NO 37
<211> LENGTH: 19
<212> TYPE: PRT
<213> ORGANISM: Homo Sapiens

<400> SEQUENCE: 37

Gln Leu Tyr Asn Val Glu Ala Thr Ser Tyr Ala Leu Leu Ala Leu Leu
1               5                   10                  15

Gln Leu Lys

<210> SEQ ID NO 38
<211> LENGTH: 19
<212> TYPE: PRT
<213> ORGANISM: Homo Sapiens

<400> SEQUENCE: 38

Asp Ala Pro Asp His Gln Glu Leu Asn Leu Asp Val Ser Leu Gln Leu
1               5                   10                  15

Pro Ser Arg

<210> SEQ ID NO 39
<211> LENGTH: 18
<212> TYPE: PRT
<213> ORGANISM: Homo Sapiens

<400> SEQUENCE: 39

Ser Tyr Thr Val Ala Ile Ala Gly Tyr Ala Leu Ala Gln Met Gly Arg
1               5                   10                  15

Leu Lys

<210> SEQ ID NO 40
<211> LENGTH: 16
<212> TYPE: PRT
<213> ORGANISM: Homo Sapiens

<400> SEQUENCE: 40

Asp Met Ala Leu Thr Ala Phe Val Leu Ile Ser Leu Gln Glu Ala Lys
1               5                   10                  15

<210> SEQ ID NO 41
<211> LENGTH: 16
<212> TYPE: PRT
<213> ORGANISM: Homo Sapiens

<400> SEQUENCE: 41

Asp Ile Cys Glu Glu Gln Val Asn Ser Leu Pro Gly Ser Ile Thr Lys
1               5                   10                  15

<210> SEQ ID NO 42
<211> LENGTH: 12
<212> TYPE: PRT
<213> ORGANISM: Homo Sapiens

<400> SEQUENCE: 42

Ala Pro Ser Thr Trp Leu Thr Ala Tyr Val Val Lys
1               5                   10

<210> SEQ ID NO 43
<211> LENGTH: 12
<212> TYPE: PRT
<213> ORGANISM: Homo Sapiens

<400> SEQUENCE: 43

Gln Pro Ser Ser Ala Phe Ala Ala Phe Val Lys Arg
1               5                   10

<210> SEQ ID NO 44
<211> LENGTH: 12
<212> TYPE: PRT
<213> ORGANISM: Homo Sapiens

<400> SEQUENCE: 44

Gly Pro Leu Leu Asn Lys Phe Leu Thr Thr Ala Lys
1               5                   10

<210> SEQ ID NO 45
<211> LENGTH: 9
<212> TYPE: PRT
<213> ORGANISM: Homo Sapiens

<400> SEQUENCE: 45

Gly Tyr Thr Gln Gln Leu Ala Phe Arg
1               5

<210> SEQ ID NO 46
<211> LENGTH: 9
<212> TYPE: PRT
<213> ORGANISM: Homo Sapiens

<400> SEQUENCE: 46

Gln Gly Ala Leu Glu Leu Ile Lys Lys
1               5

<210> SEQ ID NO 47

```
<211> LENGTH: 6
<212> TYPE: PRT
<213> ORGANISM: Homo Sapiens

<400> SEQUENCE: 47

Trp Leu Asn Glu Gln Arg
1               5

<210> SEQ ID NO 48
<211> LENGTH: 6
<212> TYPE: PRT
<213> ORGANISM: Homo Sapiens

<400> SEQUENCE: 48

Trp Leu Ile Leu Glu Lys
1               5

<210> SEQ ID NO 49
<211> LENGTH: 6
<212> TYPE: PRT
<213> ORGANISM: Homo Sapiens

<400> SEQUENCE: 49

Trp Glu Asp Pro Gly Lys
1               5

<210> SEQ ID NO 50
<211> LENGTH: 19
<212> TYPE: PRT
<213> ORGANISM: Homo Sapiens

<400> SEQUENCE: 50

Ser Leu Ala Glu Leu Gly Gly His Leu Asp Gln Gln Val Glu Phe
1               5                   10                  15

Arg Arg Arg

<210> SEQ ID NO 51
<211> LENGTH: 19
<212> TYPE: PRT
<213> ORGANISM: Homo Sapiens

<400> SEQUENCE: 51

Ala Arg Leu Leu Pro His Ala Asn Glu Val Ser Gln Lys Ile Gly Asp
1               5                   10                  15

Asn Leu Arg

<210> SEQ ID NO 52
<211> LENGTH: 19
<212> TYPE: PRT
<213> ORGANISM: Homo Sapiens

<400> SEQUENCE: 52

Gln Lys Leu Gly Pro His Ala Gly Asp Val Glu Gly His Leu Ser Phe
1               5                   10                  15

Leu Glu Lys

<210> SEQ ID NO 53
<211> LENGTH: 18
<212> TYPE: PRT
<213> ORGANISM: Homo Sapiens

<400> SEQUENCE: 53

Glu Asn Ala Asp Ser Leu Gln Ala Ser Leu Arg Pro His Ala Asp Glu
1               5                   10                  15
```

Leu Lys

<210> SEQ ID NO 54
<211> LENGTH: 14
<212> TYPE: PRT
<213> ORGANISM: Homo Sapiens

<400> SEQUENCE: 54

Glu Leu Gln Gln Arg Leu Glu Pro Tyr Ala Asp Gln Leu Arg
1               5                   10

<210> SEQ ID NO 55
<211> LENGTH: 12
<212> TYPE: PRT
<213> ORGANISM: Homo Sapiens

<400> SEQUENCE: 55

Val Lys Ile Asp Gln Thr Val Glu Glu Leu Arg Arg
1               5                   10

<210> SEQ ID NO 56
<211> LENGTH: 12
<212> TYPE: PRT
<213> ORGANISM: Homo Sapiens

<400> SEQUENCE: 56

Thr Gln Val Asn Thr Gln Ala Glu Gln Leu Arg Arg
1               5                   10

<210> SEQ ID NO 57
<211> LENGTH: 15
<212> TYPE: PRT
<213> ORGANISM: Homo Sapiens

<400> SEQUENCE: 57

Ala Val Val Leu Thr Leu Ala Leu Val Ala Val Ala Gly Ala Arg
1               5                   10                  15

<210> SEQ ID NO 58
<211> LENGTH: 11
<212> TYPE: PRT
<213> ORGANISM: Homo Sapiens

<400> SEQUENCE: 58

Gly Arg Leu Thr Pro Tyr Ala Asp Glu Phe Lys
1               5                   10

<210> SEQ ID NO 59
<211> LENGTH: 11
<212> TYPE: PRT
<213> ORGANISM: Homo Sapiens

<400> SEQUENCE: 59

Ala Lys Ile Asp Gln Asn Val Glu Glu Leu Lys
1               5                   10

<210> SEQ ID NO 60
<211> LENGTH: 11
<212> TYPE: PRT
<213> ORGANISM: Homo Sapiens

<400> SEQUENCE: 60

Gln Arg Leu Ala Pro Leu Ala Glu Asp Val Arg
1               5                   10

```
<210> SEQ ID NO 61
<211> LENGTH: 10
<212> TYPE: PRT
<213> ORGANISM: Homo Sapiens

<400> SEQUENCE: 61

Ala Leu Val Gln Gln Met Glu Gln Leu Arg
1               5                   10

<210> SEQ ID NO 62
<211> LENGTH: 11
<212> TYPE: PRT
<213> ORGANISM: Homo Sapiens

<400> SEQUENCE: 62

Ala Arg Ile Ser Ala Ser Ala Glu Glu Leu Arg
1               5                   10

<210> SEQ ID NO 63
<211> LENGTH: 10
<212> TYPE: PRT
<213> ORGANISM: Homo Sapiens

<400> SEQUENCE: 63

Val Glu Pro Tyr Gly Glu Asn Phe Asn Lys
1               5                   10

<210> SEQ ID NO 64
<211> LENGTH: 9
<212> TYPE: PRT
<213> ORGANISM: Homo Sapiens

<400> SEQUENCE: 64

Val Asn Ser Phe Phe Ser Thr Phe Lys
1               5

<210> SEQ ID NO 65
<211> LENGTH: 8
<212> TYPE: PRT
<213> ORGANISM: Homo Sapiens

<400> SEQUENCE: 65

Gln Leu Thr Pro Tyr Ala Gln Arg
1               5

<210> SEQ ID NO 66
<211> LENGTH: 8
<212> TYPE: PRT
<213> ORGANISM: Homo Sapiens

<400> SEQUENCE: 66

Glu Ala Val Glu His Leu Gln Lys
1               5

<210> SEQ ID NO 67
<211> LENGTH: 8
<212> TYPE: PRT
<213> ORGANISM: Homo Sapiens

<400> SEQUENCE: 67

Gly Asn Thr Glu Gly Leu Gln Lys
1               5

<210> SEQ ID NO 68
<211> LENGTH: 16
```

```
<212> TYPE: PRT
<213> ORGANISM: Homo Sapiens

<400> SEQUENCE: 68

Val Arg Leu Ala Ser His Leu Arg Lys Leu Arg Lys Arg Leu Leu Arg
1               5                   10                  15

<210> SEQ ID NO 69
<211> LENGTH: 17
<212> TYPE: PRT
<213> ORGANISM: Homo Sapiens

<400> SEQUENCE: 69

Asp Ala Asp Asp Leu Gln Lys Arg Leu Ala Val Tyr Gln Ala Gly Ala
1               5                   10                  15

Arg

<210> SEQ ID NO 70
<211> LENGTH: 17
<212> TYPE: PRT
<213> ORGANISM: Homo Sapiens

<400> SEQUENCE: 70

Val Leu Trp Ala Ala Leu Leu Val Thr Phe Leu Ala Gly Cys Gln Ala
1               5                   10                  15

Lys

<210> SEQ ID NO 71
<211> LENGTH: 15
<212> TYPE: PRT
<213> ORGANISM: Homo Sapiens

<400> SEQUENCE: 71

Ser Glu Leu Glu Glu Gln Leu Thr Pro Val Ala Glu Glu Thr Arg
1               5                   10                  15

<210> SEQ ID NO 72
<211> LENGTH: 13
<212> TYPE: PRT
<213> ORGANISM: Homo Sapiens

<400> SEQUENCE: 72

Trp Glu Leu Ala Leu Gly Arg Phe Trp Asp Tyr Leu Arg
1               5                   10

<210> SEQ ID NO 73
<211> LENGTH: 15
<212> TYPE: PRT
<213> ORGANISM: Homo Sapiens

<400> SEQUENCE: 73

Gly Glu Val Gln Ala Met Leu Gly Gln Ser Thr Glu Glu Leu Arg
1               5                   10                  15

<210> SEQ ID NO 74
<211> LENGTH: 14
<212> TYPE: PRT
<213> ORGANISM: Homo Sapiens

<400> SEQUENCE: 74

Val Glu Gln Ala Val Glu Thr Glu Pro Glu Pro Glu Leu Arg
1               5                   10

<210> SEQ ID NO 75
```

```
<211> LENGTH: 17
<212> TYPE: PRT
<213> ORGANISM: Homo Sapiens

<400> SEQUENCE: 75

Val Gln Ala Ala Val Gly Thr Ser Ala Ala Pro Val Pro Ser Asp Asn
1               5                   10                  15

His

<210> SEQ ID NO 76
<211> LENGTH: 12
<212> TYPE: PRT
<213> ORGANISM: Homo Sapiens

<400> SEQUENCE: 76

Ser Trp Phe Glu Pro Leu Val Glu Asp Met Gln Arg
1               5                   10

<210> SEQ ID NO 77
<211> LENGTH: 15
<212> TYPE: PRT
<213> ORGANISM: Homo Sapiens

<400> SEQUENCE: 77

Ala Ala Thr Val Gly Ser Leu Ala Gly Gln Pro Leu Gln Glu Arg
1               5                   10                  15

<210> SEQ ID NO 78
<211> LENGTH: 11
<212> TYPE: PRT
<213> ORGANISM: Homo Sapiens

<400> SEQUENCE: 78

Glu Arg Leu Gly Pro Leu Val Glu Gln Gly Arg
1               5                   10

<210> SEQ ID NO 79
<211> LENGTH: 10
<212> TYPE: PRT
<213> ORGANISM: Homo Sapiens

<400> SEQUENCE: 79

Gln Gln Thr Glu Trp Gln Ser Gly Gln Arg
1               5                   10

<210> SEQ ID NO 80
<211> LENGTH: 9
<212> TYPE: PRT
<213> ORGANISM: Homo Sapiens

<400> SEQUENCE: 80

Ala Gln Ala Trp Gly Glu Arg Leu Arg
1               5

<210> SEQ ID NO 81
<211> LENGTH: 8
<212> TYPE: PRT
<213> ORGANISM: Homo Sapiens

<400> SEQUENCE: 81

Ala Leu Met Asp Glu Thr Met Lys
1               5

<210> SEQ ID NO 82
<211> LENGTH: 8
```

```
<212> TYPE: PRT
<213> ORGANISM: Homo Sapiens

<400> SEQUENCE: 82

Gln Trp Ala Gly Leu Val Glu Lys
1               5

<210> SEQ ID NO 83
<211> LENGTH: 18
<212> TYPE: PRT
<213> ORGANISM: Homo Sapiens

<400> SEQUENCE: 83

Val Ser Val Leu Cys Ile Trp Met Ser Ala Leu Phe Leu Gly Val Gly
1               5                   10                  15

Val Arg

<210> SEQ ID NO 84
<211> LENGTH: 15
<212> TYPE: PRT
<213> ORGANISM: Homo Sapiens

<400> SEQUENCE: 84

Val Thr Glu Pro Ile Ser Ala Glu Ser Gly Glu Gln Val Glu Arg
1               5                   10                  15

<210> SEQ ID NO 85
<211> LENGTH: 13
<212> TYPE: PRT
<213> ORGANISM: Homo Sapiens

<400> SEQUENCE: 85

Trp Trp Thr Gln Ala Gln Ala His Asp Leu Val Ile Lys
1               5                   10

<210> SEQ ID NO 86
<211> LENGTH: 15
<212> TYPE: PRT
<213> ORGANISM: Homo Sapiens

<400> SEQUENCE: 86

Ala Asn Leu Gln Ser Val Pro His Ala Ser Ala Ser Arg Pro Arg
1               5                   10                  15

<210> SEQ ID NO 87
<211> LENGTH: 11
<212> TYPE: PRT
<213> ORGANISM: Homo Sapiens

<400> SEQUENCE: 87

Ser Lys Leu Glu Asp Asn Ile Arg Arg Leu Arg
1               5                   10

<210> SEQ ID NO 88
<211> LENGTH: 11
<212> TYPE: PRT
<213> ORGANISM: Homo Sapiens

<400> SEQUENCE: 88

Val Asn Glu Pro Ser Ile Leu Glu Met Ser Arg
1               5                   10

<210> SEQ ID NO 89
<211> LENGTH: 9
<212> TYPE: PRT
```

```
<213> ORGANISM: Homo Sapiens

<400> SEQUENCE: 89

Ser Glu Thr Ala Glu Glu Leu Lys Lys
1               5

<210> SEQ ID NO 90
<211> LENGTH: 8
<212> TYPE: PRT
<213> ORGANISM: Homo Sapiens

<400> SEQUENCE: 90

Asn Glu Ala Asp Glu Leu Arg Lys
1               5

<210> SEQ ID NO 91
<211> LENGTH: 8
<212> TYPE: PRT
<213> ORGANISM: Homo Sapiens

<400> SEQUENCE: 91

Met Glu Gly Ala Ala Leu Leu Arg
1               5

<210> SEQ ID NO 92
<211> LENGTH: 8
<212> TYPE: PRT
<213> ORGANISM: Homo Sapiens

<400> SEQUENCE: 92

Ala Leu Ala Asp Gly Val Gln Lys
1               5

<210> SEQ ID NO 93
<211> LENGTH: 20
<212> TYPE: PRT
<213> ORGANISM: Homo Sapiens

<400> SEQUENCE: 93

Asp Asp Pro Asp Ala Pro Leu Gln Pro Val Thr Pro Leu Gln Leu Phe
1               5                   10                  15

Glu Gly Arg Arg
            20

<210> SEQ ID NO 94
<211> LENGTH: 19
<212> TYPE: PRT
<213> ORGANISM: Homo Sapiens

<400> SEQUENCE: 94

Ala Leu Glu Ile Leu Gln Glu Asp Leu Ile Asp Glu Asp Ile
1               5                   10                  15

Pro Val Arg

<210> SEQ ID NO 95
<211> LENGTH: 20
<212> TYPE: PRT
<213> ORGANISM: Homo Sapiens

<400> SEQUENCE: 95

Ala Ala Cys Ala Gln Leu Asn Asp Phe Leu Gln Glu Tyr Gly Thr Gln
1               5                   10                  15

Gly Cys Gln Val
            20
```

<210> SEQ ID NO 96
<211> LENGTH: 18
<212> TYPE: PRT
<213> ORGANISM: Homo Sapiens

<400> SEQUENCE: 96

Ala Ala Phe Arg Leu Phe Glu Thr Lys Ile Thr Gln Val Leu His Phe
1               5                   10                  15

Thr Lys

<210> SEQ ID NO 97
<211> LENGTH: 19
<212> TYPE: PRT
<213> ORGANISM: Homo Sapiens

<400> SEQUENCE: 97

Met Arg Pro Ser Thr Asp Thr Ile Thr Val Met Val Glu Asn Ser His
1               5                   10                  15

Gly Leu Arg

<210> SEQ ID NO 98
<211> LENGTH: 19
<212> TYPE: PRT
<213> ORGANISM: Homo Sapiens

<400> SEQUENCE: 98

Gly Leu Glu Ser Gln Thr Lys Leu Val Asn Gly Gln Ser His Ile Ser
1               5                   10                  15

Leu Ser Lys

<210> SEQ ID NO 99
<211> LENGTH: 18
<212> TYPE: PRT
<213> ORGANISM: Homo Sapiens

<400> SEQUENCE: 99

Ala Val Gly Ser Gly Ala Thr Phe Ser His Tyr Tyr Tyr Met Ile Leu
1               5                   10                  15

Ser Arg

<210> SEQ ID NO 100
<211> LENGTH: 20
<212> TYPE: PRT
<213> ORGANISM: Homo Sapiens

<400> SEQUENCE: 100

Val Asp Val Gln Ala Gly Ala Cys Glu Gly Lys Leu Glu Leu Ser Val
1               5                   10                  15

Asp Gly Ala Lys
            20

<210> SEQ ID NO 101
<211> LENGTH: 17
<212> TYPE: PRT
<213> ORGANISM: Homo Sapiens

<400> SEQUENCE: 101

Gly His Leu Phe Leu Gln Thr Asp Gln Pro Ile Tyr Asn Pro Gly Gln
1               5                   10                  15

Arg

```
<210> SEQ ID NO 102
<211> LENGTH: 19
<212> TYPE: PRT
<213> ORGANISM: Homo Sapiens

<400> SEQUENCE: 102

Ser Arg Leu Leu Ala Thr Leu Cys Ser Ala Glu Val Cys Gln Cys Ala
1               5                   10                  15

Glu Gly Lys

<210> SEQ ID NO 103
<211> LENGTH: 17
<212> TYPE: PRT
<213> ORGANISM: Homo Sapiens

<400> SEQUENCE: 103

Gly Leu Glu Glu Glu Leu Gln Phe Ser Leu Gly Ser Lys Ile Asn Val
1               5                   10                  15

Lys

<210> SEQ ID NO 104
<211> LENGTH: 16
<212> TYPE: PRT
<213> ORGANISM: Homo Sapiens

<400> SEQUENCE: 104

Glu Pro Phe Leu Ser Cys Cys Gln Phe Ala Glu Ser Leu Arg Lys Lys
1               5                   10                  15

<210> SEQ ID NO 105
<211> LENGTH: 18
<212> TYPE: PRT
<213> ORGANISM: Homo Sapiens

<400> SEQUENCE: 105

Gly Cys Gly Glu Gln Thr Met Ile Tyr Leu Ala Pro Thr Leu Ala Ala
1               5                   10                  15

Ser Arg

<210> SEQ ID NO 106
<211> LENGTH: 16
<212> TYPE: PRT
<213> ORGANISM: Homo Sapiens

<400> SEQUENCE: 106

Ala Ile Asn Glu Lys Leu Gly Gln Tyr Ala Ser Pro Thr Ala Lys Arg
1               5                   10                  15

<210> SEQ ID NO 107
<211> LENGTH: 15
<212> TYPE: PRT
<213> ORGANISM: Homo Sapiens

<400> SEQUENCE: 107

Thr Thr Asn Ile Gln Gly Ile Asn Leu Leu Phe Ser Ser Arg Arg
1               5                   10                  15

<210> SEQ ID NO 108
<211> LENGTH: 15
<212> TYPE: PRT
<213> ORGANISM: Homo Sapiens

<400> SEQUENCE: 108
```

```
His Leu Val Pro Gly Ala Pro Phe Leu Leu Gln Ala Leu Val Arg
1               5                   10                  15
```

<210> SEQ ID NO 109
<211> LENGTH: 13
<212> TYPE: PRT
<213> ORGANISM: Homo Sapiens

<400> SEQUENCE: 109

```
Glu Glu Leu Val Tyr Glu Leu Asn Pro Leu Asp His Arg
1               5                   10
```

<210> SEQ ID NO 110
<211> LENGTH: 14
<212> TYPE: PRT
<213> ORGANISM: Homo Sapiens

<400> SEQUENCE: 110

```
Asn Thr Thr Cys Gln Asp Leu Gln Ile Glu Val Thr Val Lys
1               5                   10
```

<210> SEQ ID NO 111
<211> LENGTH: 14
<212> TYPE: PRT
<213> ORGANISM: Homo Sapiens

<400> SEQUENCE: 111

```
Gly Pro Glu Val Gln Leu Val Ala His Ser Pro Trp Leu Lys
1               5                   10
```

<210> SEQ ID NO 112
<211> LENGTH: 13
<212> TYPE: PRT
<213> ORGANISM: Homo Sapiens

<400> SEQUENCE: 112

```
Cys Cys Gln Asp Gly Val Thr Arg Leu Pro Met Met Arg
1               5                   10
```

<210> SEQ ID NO 113
<211> LENGTH: 13
<212> TYPE: PRT
<213> ORGANISM: Homo Sapiens

<400> SEQUENCE: 113

```
Ala Glu Met Ala Asp Gln Ala Ala Ala Trp Leu Thr Arg
1               5                   10
```

<210> SEQ ID NO 114
<211> LENGTH: 20
<212> TYPE: PRT
<213> ORGANISM: Homo Sapiens

<400> SEQUENCE: 114

```
Val Thr Ile Ala Gln Gly Gly Val Leu Pro Asn Ile Gln Ala Val Leu
1               5                   10                  15

Leu Pro Lys Lys
            20
```

<210> SEQ ID NO 115
<211> LENGTH: 11
<212> TYPE: PRT
<213> ORGANISM: Homo Sapiens

<400> SEQUENCE: 115

Asn Asp Glu Glu Leu Asn Lys Leu Leu Gly Lys
1               5                   10

<210> SEQ ID NO 116
<211> LENGTH: 9
<212> TYPE: PRT
<213> ORGANISM: Homo Sapiens

<400> SEQUENCE: 116

Ala Gly Leu Gln Phe Pro Val Gly Arg
1               5

<210> SEQ ID NO 117
<211> LENGTH: 7
<212> TYPE: PRT
<213> ORGANISM: Homo Sapiens

<400> SEQUENCE: 117

Val His Arg Leu Leu Arg Lys
1               5

<210> SEQ ID NO 118
<211> LENGTH: 21
<212> TYPE: PRT
<213> ORGANISM: Homo Sapiens

<400> SEQUENCE: 118

Ser Thr Ala Ala Met Ser Thr Tyr Thr Gly Ile Phe Thr Asp Gln Val
1               5                   10                  15

Leu Ser Val Leu Lys
                20

<210> SEQ ID NO 119
<211> LENGTH: 11
<212> TYPE: PRT
<213> ORGANISM: Homo Sapiens

<400> SEQUENCE: 119

Thr Tyr Leu Pro Ala Val Asp Glu Lys Leu Arg
1               5                   10

<210> SEQ ID NO 120
<211> LENGTH: 11
<212> TYPE: PRT
<213> ORGANISM: Homo Sapiens

<400> SEQUENCE: 120

Glu Ser Leu Ser Ser Tyr Trp Glu Ser Ala Lys
1               5                   10

<210> SEQ ID NO 121
<211> LENGTH: 9
<212> TYPE: PRT
<213> ORGANISM: Homo Sapiens

<400> SEQUENCE: 121

Thr Ala Ala Gln Asn Leu Tyr Glu Lys
1               5

<210> SEQ ID NO 122
<211> LENGTH: 13
<212> TYPE: PRT
<213> ORGANISM: Homo Sapiens

<400> SEQUENCE: 122

Trp Ile Tyr His Leu Thr Glu Gly Ser Thr Asp Leu Arg
1               5                   10

<210> SEQ ID NO 123
<211> LENGTH: 10
<212> TYPE: PRT
<213> ORGANISM: Homo Sapiens

<400> SEQUENCE: 123

Asn Gln Glu Ala Cys Glu Leu Ser Asn Asn
1               5                   10

<210> SEQ ID NO 124
<211> LENGTH: 9
<212> TYPE: PRT
<213> ORGANISM: Homo Sapiens

<400> SEQUENCE: 124

Ser Leu Thr Ser Cys Leu Asp Ser Lys
1               5

<210> SEQ ID NO 125
<211> LENGTH: 8
<212> TYPE: PRT
<213> ORGANISM: Homo Sapiens

<400> SEQUENCE: 125

Thr Glu Gly Arg Pro Asp Met Lys
1               5

<210> SEQ ID NO 126
<211> LENGTH: 8
<212> TYPE: PRT
<213> ORGANISM: Homo Sapiens

<400> SEQUENCE: 126

Asp Gly Leu Cys Val Pro Arg Lys
1               5

<210> SEQ ID NO 127
<211> LENGTH: 20
<212> TYPE: PRT
<213> ORGANISM: Homo Sapiens

<400> SEQUENCE: 127

Gly Asp Val Phe Thr Met Pro Glu Asp Glu Tyr Thr Val Tyr Asp Asp
1               5                   10                  15

Gly Glu Glu Lys
            20

<210> SEQ ID NO 128
<211> LENGTH: 18
<212> TYPE: PRT
<213> ORGANISM: Homo Sapiens

<400> SEQUENCE: 128

Gly Ser Gln Tyr Trp Arg Phe Glu Asp Gly Val Leu Asp Pro Asp Tyr
1               5                   10                  15

Pro Arg

<210> SEQ ID NO 129
<211> LENGTH: 14
<212> TYPE: PRT
<213> ORGANISM: Homo Sapiens

```
<400> SEQUENCE: 129

Asp Ser Trp Glu Asp Ile Phe Glu Leu Leu Phe Trp Gly Arg
1               5                   10

<210> SEQ ID NO 130
<211> LENGTH: 15
<212> TYPE: PRT
<213> ORGANISM: Homo Sapiens

<400> SEQUENCE: 130

Ser Ile Ala Gln Tyr Trp Leu Gly Cys Pro Ala Pro Gly His Leu
1               5                   10                  15

<210> SEQ ID NO 131
<211> LENGTH: 11
<212> TYPE: PRT
<213> ORGANISM: Homo Sapiens

<400> SEQUENCE: 131

Ala Val Arg Pro Gly Tyr Pro Lys Leu Ile Arg
1               5                   10

<210> SEQ ID NO 132
<211> LENGTH: 10
<212> TYPE: PRT
<213> ORGANISM: Homo Sapiens

<400> SEQUENCE: 132

Gly Gln Tyr Cys Tyr Glu Leu Asp Glu Lys
1               5                   10

<210> SEQ ID NO 133
<211> LENGTH: 10
<212> TYPE: PRT
<213> ORGANISM: Homo Sapiens

<400> SEQUENCE: 133

Val Asp Thr Val Asp Pro Pro Tyr Pro Arg
1               5                   10

<210> SEQ ID NO 134
<211> LENGTH: 10
<212> TYPE: PRT
<213> ORGANISM: Homo Sapiens

<400> SEQUENCE: 134

Cys Thr Glu Gly Phe Asn Val Asp Lys Lys
1               5                   10

<210> SEQ ID NO 135
<211> LENGTH: 9
<212> TYPE: PRT
<213> ORGANISM: Homo Sapiens

<400> SEQUENCE: 135

Asn Gln Asn Ser Arg Arg Pro Ser Arg
1               5

<210> SEQ ID NO 136
<211> LENGTH: 8
<212> TYPE: PRT
<213> ORGANISM: Homo Sapiens

<400> SEQUENCE: 136

Asn Gly Ser Leu Phe Ala Phe Arg
```

<210> SEQ ID NO 137
<211> LENGTH: 19
<212> TYPE: PRT
<213> ORGANISM: Homo Sapiens

<400> SEQUENCE: 137

Glu Ile Leu Ser Val Asp Cys Ser Thr Asn Asn Pro Ser Gln Ala Lys
1               5                   10                  15

Leu Arg Arg

<210> SEQ ID NO 138
<211> LENGTH: 16
<212> TYPE: PRT
<213> ORGANISM: Homo Sapiens

<400> SEQUENCE: 138

Ala Ser Ser Ile Ile Asp Glu Leu Phe Gln Asp Arg Phe Phe Thr Arg
1               5                   10                  15

<210> SEQ ID NO 139
<211> LENGTH: 15
<212> TYPE: PRT
<213> ORGANISM: Homo Sapiens

<400> SEQUENCE: 139

Gln Gln Thr His Met Leu Asp Val Met Gln Asp His Phe Ser Arg
1               5                   10                  15

<210> SEQ ID NO 140
<211> LENGTH: 15
<212> TYPE: PRT
<213> ORGANISM: Homo Sapiens

<400> SEQUENCE: 140

Glu Leu Asp Glu Ser Leu Gln Val Ala Glu Arg Leu Thr Arg Lys
1               5                   10                  15

<210> SEQ ID NO 141
<211> LENGTH: 13
<212> TYPE: PRT
<213> ORGANISM: Homo Sapiens

<400> SEQUENCE: 141

Thr Leu Leu Ser Asn Leu Glu Glu Ala Lys Lys Lys Lys
1               5                   10

<210> SEQ ID NO 142
<211> LENGTH: 11
<212> TYPE: PRT
<213> ORGANISM: Homo Sapiens

<400> SEQUENCE: 142

Asn Pro Lys Phe Met Glu Thr Val Ala Glu Lys
1               5                   10

<210> SEQ ID NO 143
<211> LENGTH: 9
<212> TYPE: PRT
<213> ORGANISM: Homo Sapiens

<400> SEQUENCE: 143

Gln Thr Cys Met Lys Phe Tyr Ala Arg
1               5

<210> SEQ ID NO 144
<211> LENGTH: 10
<212> TYPE: PRT
<213> ORGANISM: Homo Sapiens

<400> SEQUENCE: 144

Glu Ile Gln Asn Ala Val Asn Gly Val Lys
1               5                   10

<210> SEQ ID NO 145
<211> LENGTH: 8
<212> TYPE: PRT
<213> ORGANISM: Homo Sapiens

<400> SEQUENCE: 145

Ala Leu Gln Glu Tyr Arg Lys Lys
1               5

<210> SEQ ID NO 146
<211> LENGTH: 8
<212> TYPE: PRT
<213> ORGANISM: Homo Sapiens

<400> SEQUENCE: 146

Glu Asp Ala Leu Asn Glu Thr Arg
1               5

<210> SEQ ID NO 147
<211> LENGTH: 8
<212> TYPE: PRT
<213> ORGANISM: Homo Sapiens

<400> SEQUENCE: 147

His Asn Ser Thr Gly Cys Leu Arg
1               5

<210> SEQ ID NO 148
<211> LENGTH: 20
<212> TYPE: PRT
<213> ORGANISM: Homo Sapiens

<400> SEQUENCE: 148

Val Gly Tyr Val Ser Gly Trp Gly Gln Ser Asp Asn Phe Lys Leu Thr
1               5                   10                  15

Asp His Leu Lys
            20

<210> SEQ ID NO 149
<211> LENGTH: 20
<212> TYPE: PRT
<213> ORGANISM: Homo Sapiens

<400> SEQUENCE: 149

Ser Pro Val Gly Val Gln Pro Ile Leu Asn Glu His Thr Phe Cys Val
1               5                   10                  15

Gly Met Ser Lys
            20

<210> SEQ ID NO 150
<211> LENGTH: 18
<212> TYPE: PRT
<213> ORGANISM: Homo Sapiens

<400> SEQUENCE: 150

```
Val Val Leu His Pro Asn Tyr His Gln Val Asp Ile Gly Leu Ile Lys
1               5                   10                  15

Leu Lys

<210> SEQ ID NO 151
<211> LENGTH: 17
<212> TYPE: PRT
<213> ORGANISM: Homo Sapiens

<400> SEQUENCE: 151

Asn Pro Ala Asn Pro Val Gln Arg Ile Leu Gly Gly His Leu Asp Ala
1               5                   10                  15

Lys

<210> SEQ ID NO 152
<211> LENGTH: 17
<212> TYPE: PRT
<213> ORGANISM: Homo Sapiens

<400> SEQUENCE: 152

Ala Val Gly Asp Lys Leu Pro Glu Cys Glu Ala Val Cys Gly Lys Pro
1               5                   10                  15

Lys

<210> SEQ ID NO 153
<211> LENGTH: 15
<212> TYPE: PRT
<213> ORGANISM: Homo Sapiens

<400> SEQUENCE: 153

Met Ser Asp Leu Gly Ala Val Ile Ser Leu Leu Leu Trp Gly Arg
1               5                   10                  15

<210> SEQ ID NO 154
<211> LENGTH: 13
<212> TYPE: PRT
<213> ORGANISM: Homo Sapiens

<400> SEQUENCE: 154

Asn Leu Phe Leu Asn His Ser Glu Asn Ala Thr Ala Lys
1               5                   10

<210> SEQ ID NO 155
<211> LENGTH: 13
<212> TYPE: PRT
<213> ORGANISM: Homo Sapiens

<400> SEQUENCE: 155

Thr Glu Gly Asp Gly Val Tyr Thr Leu Asn Asp Lys Lys
1               5                   10

<210> SEQ ID NO 156
<211> LENGTH: 13
<212> TYPE: PRT
<213> ORGANISM: Homo Sapiens

<400> SEQUENCE: 156

Asp Ile Ala Pro Thr Leu Thr Leu Tyr Val Gly Lys Lys
1               5                   10

<210> SEQ ID NO 157
<211> LENGTH: 12
<212> TYPE: PRT
```

<213> ORGANISM: Homo Sapiens

<400> SEQUENCE: 157

Ser Cys Ala Val Ala Glu Tyr Gly Val Tyr Val Lys
1               5                   10

<210> SEQ ID NO 158
<211> LENGTH: 10
<212> TYPE: PRT
<213> ORGANISM: Homo Sapiens

<400> SEQUENCE: 158

Val Thr Ser Ile Gln Asp Trp Val Gln Lys
1               5                   10

<210> SEQ ID NO 159
<211> LENGTH: 9
<212> TYPE: PRT
<213> ORGANISM: Homo Sapiens

<400> SEQUENCE: 159

Val Met Pro Ile Cys Leu Pro Ser Lys
1               5

<210> SEQ ID NO 160
<211> LENGTH: 267
<212> TYPE: PRT
<213> ORGANISM: Homo Sapiens

<400> SEQUENCE: 160

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
                20                  25                  30

Asp Arg Val Lys Asp Leu Ala Thr Val Tyr Val Asp Val Leu Lys Asp
            35                  40                  45

Ser Gly Arg Asp Tyr Val Ser Gln Phe Glu Gly Ser Ala Leu Gly Lys
        50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
                100                 105                 110

Asp Leu Glu Glu Val Lys Ala Lys Val Gln Pro Tyr Leu Asp Asp Phe
            115                 120                 125

Gln Lys Lys Trp Gln Glu Glu Met Glu Leu Tyr Arg Gln Lys Val Glu
        130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
                180                 185                 190

Glu Leu Arg Gln Arg Leu Ala Ala Arg Leu Glu Ala Leu Lys Glu Asn
            195                 200                 205

Gly Gly Ala Arg Leu Ala Glu Tyr His Ala Lys Ala Thr Glu His Leu
        210                 215                 220

Ser Thr Leu Ser Glu Lys Ala Lys Pro Ala Leu Glu Asp Leu Arg Gln

```
                225                 230                 235                 240
Gly Leu Leu Pro Val Leu Glu Ser Phe Lys Val Ser Phe Leu Ser Ala
                    245                 250                 255
Leu Glu Glu Tyr Thr Lys Lys Leu Asn Thr Gln
            260                 265
```

<210> SEQ ID NO 161
<211> LENGTH: 13
<212> TYPE: PRT
<213> ORGANISM: Homo Sapiens

<400> SEQUENCE: 161

```
Asp Tyr Val Ser Gln Phe Glu Gly Ser Ala Leu Gly Lys
1               5                   10
```

<210> SEQ ID NO 162
<211> LENGTH: 18
<212> TYPE: PRT
<213> ORGANISM: Homo Sapiens

<400> SEQUENCE: 162

```
Gln Lys Leu His Glu Leu Gln Glu Lys Leu Ser Pro Leu Gly Glu Glu
1               5                   10                  15

Met Arg
```

<210> SEQ ID NO 163
<211> LENGTH: 17
<212> TYPE: PRT
<213> ORGANISM: Homo Sapiens

<400> SEQUENCE: 163

```
Val Ser Phe Leu Ser Ala Leu Glu Glu Tyr Thr Lys Lys Leu Asn Thr
1               5                   10                  15

Gln
```

<210> SEQ ID NO 164
<211> LENGTH: 15
<212> TYPE: PRT
<213> ORGANISM: Homo Sapiens

<400> SEQUENCE: 164

```
His Phe Trp Gln Gln Asp Glu Pro Pro Gln Ser Pro Trp Asp Arg
1               5                   10                  15
```

<210> SEQ ID NO 165
<211> LENGTH: 16
<212> TYPE: PRT
<213> ORGANISM: Homo Sapiens

<400> SEQUENCE: 165

```
Glu Gln Leu Gly Pro Val Thr Gln Glu Phe Trp Asp Asn Leu Glu Lys
1               5                   10                  15
```

<210> SEQ ID NO 166
<211> LENGTH: 17
<212> TYPE: PRT
<213> ORGANISM: Homo Sapiens

<400> SEQUENCE: 166

```
Ala Ala Val Leu Thr Leu Ala Val Leu Phe Leu Thr Gly Ser Gln Ala
1               5                   10                  15

Arg
```

```
<210> SEQ ID NO 167
<211> LENGTH: 13
<212> TYPE: PRT
<213> ORGANISM: Homo Sapiens

<400> SEQUENCE: 167

Glu Asn Gly Gly Ala Arg Leu Ala Glu Tyr His Ala Lys
1               5                   10

<210> SEQ ID NO 168
<211> LENGTH: 11
<212> TYPE: PRT
<213> ORGANISM: Homo Sapiens

<400> SEQUENCE: 168

Val Gln Pro Tyr Leu Asp Asp Phe Gln Lys Lys
1               5                   10

<210> SEQ ID NO 169
<211> LENGTH: 11
<212> TYPE: PRT
<213> ORGANISM: Homo Sapiens

<400> SEQUENCE: 169

Thr His Leu Ala Pro Tyr Ser Asp Glu Leu Arg
1               5                   10

<210> SEQ ID NO 170
<211> LENGTH: 9
<212> TYPE: PRT
<213> ORGANISM: Homo Sapiens

<400> SEQUENCE: 170

Trp Gln Glu Glu Met Glu Leu Tyr Arg
1               5

<210> SEQ ID NO 171
<211> LENGTH: 100
<212> TYPE: PRT
<213> ORGANISM: Homo Sapiens

<400> SEQUENCE: 171

Met Lys Leu Leu Ala Ala Thr Val Leu Leu Thr Ile Cys Ser Leu
1               5                   10                  15

Glu Gly Ala Leu Val Arg Arg Gln Ala Lys Glu Pro Cys Val Glu Ser
                20                  25                  30

Leu Val Ser Gln Tyr Phe Gln Thr Val Thr Asp Tyr Gly Lys Asp Leu
        35                  40                  45

Met Glu Lys Val Lys Ser Pro Glu Leu Gln Ala Glu Ala Lys Ser Tyr
    50                  55                  60

Phe Glu Lys Ser Lys Glu Gln Leu Thr Pro Leu Ile Lys Lys Ala Gly
65                  70                  75                  80

Thr Glu Leu Val Asn Phe Leu Ser Tyr Phe Val Glu Leu Gly Thr Gln
                85                  90                  95

Pro Ala Thr Gln
            100

<210> SEQ ID NO 172
<211> LENGTH: 22
<212> TYPE: PRT
<213> ORGANISM: Homo Sapiens

<400> SEQUENCE: 172
```

-continued

```
Ala Gly Thr Glu Leu Val Asn Phe Leu Ser Tyr Phe Val Glu Leu Gly
1               5                   10                  15

Thr Gln Pro Ala Thr Gln
            20

<210> SEQ ID NO 173
<211> LENGTH: 20
<212> TYPE: PRT
<213> ORGANISM: Homo Sapiens

<400> SEQUENCE: 173

Glu Pro Cys Val Glu Ser Leu Val Ser Gln Tyr Phe Gln Thr Val Thr
1               5                   10                  15

Asp Tyr Gly Lys
            20

<210> SEQ ID NO 174
<211> LENGTH: 9
<212> TYPE: PRT
<213> ORGANISM: Homo Sapiens

<400> SEQUENCE: 174

Glu Gln Leu Thr Pro Leu Ile Lys Lys
1               5

<210> SEQ ID NO 175
<211> LENGTH: 9
<212> TYPE: PRT
<213> ORGANISM: Homo Sapiens

<400> SEQUENCE: 175

Ser Pro Glu Leu Gln Ala Glu Ala Lys
1               5
```

LIPOPROTEIN-ASSOCIATED MARKERS FOR CARDIOVASCULAR DISEASE

CROSS REFERENCE TO RELATED APPLICATION

This application is a division of application Ser. No. 11/263,553, filed Oct. 31, 2005, the disclosure of which is incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is 37078SeqFinal.txt. The text file is 108 KB; was created on May 9, 2011; and is being submitted via EFS-Web with the filing of the specification.

FIELD OF THE INVENTION

The present invention generally relates to methods, reagents and kits for diagnosing cardiovascular disease in a subject, and particularly relates to the use of lipoprotein-associated markers to diagnose cardiovascular disease in a subject.

BACKGROUND OF THE INVENTION

Cardiovascular disease is a leading cause of morbidity and mortality, particularly in developed areas such as the United States and Western European countries. The incidence of mortality from cardiovascular disease has significantly decreased in the United States over the past 30 years (see Braunwald, E., *N. Engl. J. Med.* 337:1360-1369, 1997; Hoyert, D. L., et al., "Deaths: Preliminary Data for 2003" in *National Vital Statistics Reports*. Hyattsville: National Center for Health Statistics, 2005). Many factors have contributed to this improvement in patient outcome, including the identification of cardiovascular risk factors, the application of medical technologies to treat acute coronary syndrome, and the development of interventions that reduce cardiovascular risk factors. Despite these advances, however, cardiovascular disease remains a leading cause of morbidity and mortality in developed countries (see Hoyert D. L., et al., *National Vital Statistics Reports*, 2005).

Thus, there is a pressing need to identify markers that may be used for the rapid, accurate and non-invasive diagnosis and/or assessment of the risk of cardiovascular disease, and also to assess the efficacy of interventions designed to slow the initiation and progress of this disorder.

SUMMARY OF THE INVENTION

In accordance with the foregoing, in one aspect, the present invention provides methods of screening a mammalian subject to determine if the subject is at risk for developing, or is suffering from, cardiovascular disease ("CVD"). The method of this aspect of the invention comprises detecting an amount of at least one biomarker in a biological sample, or high density lipoprotein subfraction thereof, of the subject, wherein the biomarker is selected from the group consisting of Apolipoprotein C-IV ("ApoC-IV"), Paraoxonase 1 ("PON-1"), Complement Factor 3 ("C3"), Apolipoprotein A-IV ("ApoA-IV"), Apolipoprotein E ("ApoE"), Apolipoprotein L1 ("ApoL1"), Complement Factor C4 ("C4"), Complement Factor C4B1 ("C4B1"), Histone H2A, Apolipoprotein C-II ("ApoC-II"), Apolipoprotein M ("ApoM"), Vitronectin, Haptoglobin-related Protein and Clusterin. The detected amount of the biomarker is then compared to a predetermined value that is derived from measurements of the one or more biomarkers in comparable biological samples taken from the general population or a select population of mammalian subjects. A difference in the amount of the biomarker between the subject's sample and the predetermined value is indicative of the presence and/or risk of developing cardiovascular disease in the subject. In one embodiment of this aspect of the invention, an increased amount of a biomarker selected from the group consisting of ApoC-IV, PON-1, C3, C4, ApoA-IV, ApoE, ApoL1, C4B1, Histone H2A, ApoC-II, or ApoM in the subject's sample in comparison to a predetermined value, is indicative of the presence and/or risk of developing cardiovascular disease. In another embodiment of this aspect of the invention, a reduced amount of Vitronectin, Haptoglobin-related Protein or Clusterin in the subject's sample in comparison to a predetermined value is indicative of the presence or risk of developing cardiovascular disease.

In another aspect, the present invention provides methods of screening a mammalian subject to determine if the subject has one or more atherosclerotic lesions. The method of this aspect of the invention comprises detecting an amount of at least one biomarker protein in a biological sample, or HDL subfraction thereof (including a lipoprotein complex with a density from about 1.06 to about 1.21 g/mL, or from about 1.06 to 1.10 g/mL, or from about 1.10 to about 1.21 g/mL, or a complex containing ApoA-I or ApoA-II), isolated from the subject, wherein the biomarker is selected from the group consisting of PON-1, C3, C4, ApoE, ApoM and C4B1. The detected amount of the biomarker is then compared to a predetermined value that is derived from measurements of the one or more biomarkers in comparable biological samples taken from the general population or a select population of mammalian subjects. An increase in the amount of the biomarker in the HDL, $HDL_2$, $HDL_3$ and/or ApoA-I or ApoA-II fraction of the biological sample in comparison to the predetermined value is indicative of the presence of one or more atherosclerotic lesions in the subject.

In another aspect, the present invention provides an assay for determining the risk and/or presence of cardiovascular disease in a mammalian subject based on the detection of an amount of at least one protein marker in a blood sample, or HDL subfraction thereof (including a lipoprotein complex with a density from about 1.06 to about 1.21 g/mL, or from about 1.06 to 1.10 g/mL, or from about 1.10 to about 1.21 g/mL, or a complex containing ApoA-I or ApoA-II). The assay may be packaged into a kit that comprises (i) one or more detection reagents for detecting at least one marker protein selected from the group consisting of ApoC-IV, Paraoxonase 1, C3, ApoA-IV, ApoE, ApoL1, C4, C4B1, Histone H2A, ApoC-II, and ApoM, and (ii) written indicia indicating a positive correlation between the presence of the detected amount of the marker protein and risk of developing cardiovascular disease.

In another aspect, the present invention provides an assay for identifying the presence of one or more atherosclerotic lesions in a mammalian subject, based on the detection of an amount of at least one protein marker in a blood sample, or HDL subfraction thereof (including a lipoprotein complex with a density from about 1.06 to about 1.21 g/mL, or from about 1.06 to 1.10 g/mL, or from about 1.10 to about 1.21 g/mL, or a complex containing ApoA-I or ApoA-II). The assay may be packaged into a kit comprising (i) one or more detection reagents for detecting at least one marker protein selected from the group consisting of Paraoxonase 1, C3, C4, ApoE, ApoM and C4B1, and (ii) written indicia indicating a positive correlation between the presence of the detected amount of the marker protein and the presence of one or more atherosclerotic lesions in the subject.

The invention thus provides methods, reagents, and kits for identifying protein markers that are indicative of the risk and/or presence of cardiovascular disease in a mammalian subject.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
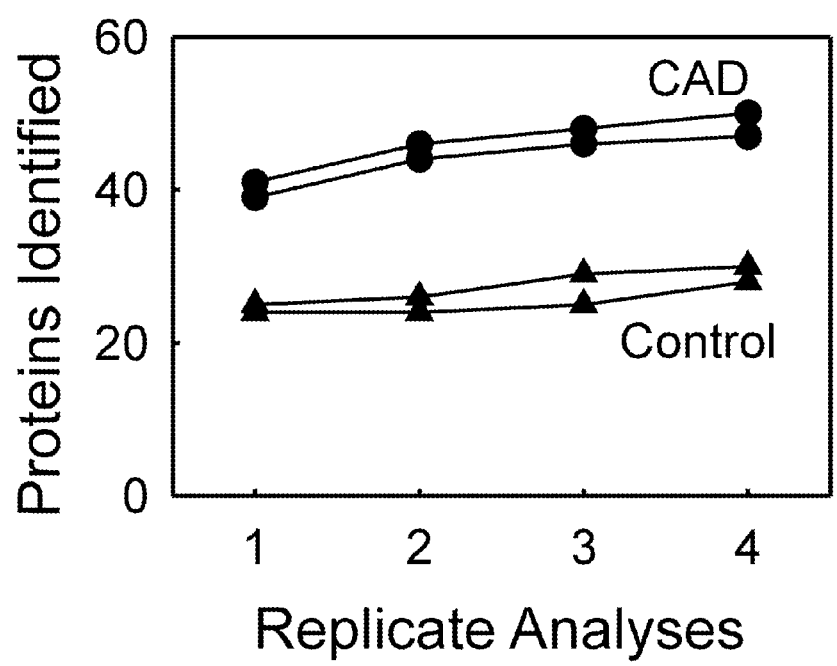
FIG. 1 presents graphical results demonstrating the reproducible identification of HDL-associated proteins using tandem mass spectroscopy. Total HDL was isolated from two normal control subjects and from two subjects with established cardiovascular disease ("CVD") using methods in accordance with an embodiment of the invention, as described in EXAMPLE 3.

Unless specifically defined herein, all terms used herein have the same meaning as they would to one skilled in the art of the present invention. The following definitions are provided in order to provide clarity with respect to the terms as they are used in the specification and claims to describe various embodiments of the present invention.

As used herein, the term "cardiovascular disease" or "CVD," generally refers to heart and blood vessel diseases, including atherosclerosis, coronary heart disease, cerebrovascular disease, and peripheral vascular disease. Cardiovascular disorders are acute manifestations of CVD and include myocardial infarction, stroke, angina pectoris, transient ischemic attacks, and congestive heart failure. Cardiovascular disease, including atherosclerosis, usually results from the build up of fatty material, inflammatory cells, extracellular matrix and plaque. Clinical symptoms and signs indicating the presence of CVD include one or more of the following: chest pain and other forms of angina, shortness of breath, sweatiness, Q waves or inverted T waves on an EKG, a high calcium score by CT scan, at least one stenotic lesion on coronary angiography, or heart attack.

As used herein, the term "biomarker" is a biological compound such as a protein or a fragment thereof, including a polypeptide or peptide that may be isolated from, or measured in the biological sample which is differentially present in a sample taken from a subject having established or potentially clinically significant CVD as compared to a comparable sample taken from an apparently normal subject that does not have CVD. A biomarker can be an intact molecule, or it can be a portion thereof that may be partially functional or recognized, for example, by a specific binding protein or other detection method. A biomarker is considered to be informative for CVD if a measurable aspect of the biomarker is associated with the presence of CVD in a subject in comparison to a predetermined value or a reference profile from a control population. Such a measurable aspect may include, for example, the presence, absence, or concentration of the biomarker, or a portion thereof, in the biological sample, and/or its presence as a part of a profile of more than one biomarker. A measurable aspect of a biomarker is also referred to as a feature. A feature may be a ratio of two or more measurable aspects of biomarkers. A biomarker profile comprises at least one measurable feature, and may comprise two, three, four, five, 10, 20, 30 or more features. The biomarker profile may also comprise at least one measurable aspect of at least one feature relative to at least one internal standard.

As used herein, the term "predetermined value" refers to the amount of one or more biomarkers in biological samples obtained from the general population or from a select population of subjects. For example, the select population may be comprised of apparently healthy subjects, such as individuals who have not previously had any sign or symptoms indicating the presence of CVD. In another example, the predetermined value may be comprised of subjects having established CVD. The predetermined value can be a cut-off value, or a range. The predetermined value can be established based upon comparative measurements between apparently healthy subjects and subjects with established CVD, as described herein.

As used herein, the term "high density lipoprotein" or "HDL, or a subfraction thereof" includes protein or lipoprotein complexes with a density from about 1.06 to about 1.21 g/mL, or from about 1.06 to 1.10 g/mL, or from about 1.10 to about 1.21 g/mL, or a complex containing ApoA-I or ApoA-II. HDL may be prepared by density ultracentrifugation, as described in Mendez, A. J., et al., *J. Biol. Chem.* 266:10104-10111, 1991, from plasma, serum, bodily fluids, or tissue. The $HDL_3$ subfraction in the density range of about 1.110 to about 1.210 g/mL, and the $HDL_2$ subfraction in the density range of about 1.06 to about 1.110g/mL may be isolated from plasma, serum, bodily fluids, tissue or total HDL by sequential density ultracentrifugation, as described in Mendez, supra. HDL is known to contain two major proteins, Apolipoprotein A-I (ApoA-I) and Apolipoprotein A-II (ApoA-II); therefore, in some embodiments, the term "HDL, or a subfraction thereof" also includes an ApoA-I and/or an ApoA-II containing protein or lipoprotein complex.

As used herein, the term "HDL-associated" refers to any biological compounds that float in the density range of HDL (d=about 1.06 to about 1.21 g/mL), and/or molecules present in a complex containing ApoA-I and/or ApoA-II, including full-length proteins, and fragments thereof, including peptides, or lipid-protein complexes such as microparticles, in HDL isolated from any sample, including lesions, blood, urine, or tissue samples.

As used herein, the term "mass spectrometer" refers to a device able to volatilize/ionize analytes to form gas-phase ions and determine their absolute or relative molecular masses. Suitable forms of volatilization/ionization are electrospray, laser/light, thermal, electrical, atomized/sprayed and the like, or combinations thereof. Suitable forms of mass spectrometry include, but are not limited to, ion trap instruments, quadrupole instruments, electrostatic and magnetic sector instruments, time of flight instruments, Fourier-transform mass spectrometers, and hybrid instruments composed of various combinations of these types of mass analyzers. These instruments may, in turn, be interfaced with a variety of sources that fractionate the samples (for example, liquid chromatography or solid-phase adsorption techniques based on chemical, or biological properties) and that ionize the samples for introduction into the mass spectrometer, including Matrix Assisted Laser Desorption (MALDI), electrospray, or nanospray ionization (ESI) or combinations thereof.

As used herein, the term "affinity detection" or "affinity purified" refers to any method that selectively detects and/or enriches the protein or analyte of interest. This includes methods based on physical properties like charge, amino acid sequence, and hydrophobicity, and can involve many different compounds that have an affinity for the analyte of interest, including but not limited to antibodies, resins, RNA, DNA, proteins, hydrophobic materials, charged materials, and dyes.

As used herein, the term "antibody" encompasses antibodies and antibody fragments thereof derived from any antibody-producing mammal (e.g., mouse, rat, rabbit, and primate including human) that specifically bind to the biomarkers or portions thereof. Exemplary antibodies include polyclonal, monoclonal, and recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof.

As used herein, the term "antibody fragment" refers to a portion derived from or related to a full length anti-biomarker antibody, generally including the antigen binding or variable region thereof. Illustrative examples of antibody fragments include Fab, Fab', F(ab)$_2$, F(ab')$_2$ and Fv fragments, scFv fragments, diabodies, linear antibodies, single-chain antibody molecules and multispecific antibodies formed from antibody fragments. Antibody and antibody fragments as used here may be incorporated into other proteins that can be produced by a variety of systems, including, but not limited to, bacteria, viruses, yeast and mammalian cells.

As used herein, "a subject" includes all mammals, including without limitation humans, non-human primates, dogs, cats, horses, sheep, goats, cows, rabbits, pigs and rodents.

As used herein, the term "percent identity" or "percent identical," when used in connection with a biomarker used in the practice of the present invention, is defined as the percentage of amino acid residues in a biomarker sequence that are identical with the amino acid sequence of a specified biomarker (such as the amino acid sequence of SEQ ID NO:1), after aligning the sequences to achieve the maximum percent identity. When making the comparison, no gaps are introduced into the biomarker sequences in order to achieve the best alignment.

Amino acid sequence identity can be determined, for example, in the following manner. The amino acid sequence of a biomarker (e.g., the amino acid sequence set forth in SEQ ID NO:1) is used to search a protein sequence database, such as the GenBank database using the BLASTP program. The program is used in the ungapped mode. Default filtering is used to remove sequence homologies due to regions of low complexity. The default parameters of BLASTP are utilized.

As used herein, the term "derivatives" of a biomarker, including proteins and peptide fragments thereof include an insertion, deletion, or substitution mutant. Preferably, any substitution mutation is conservative in that it minimally disrupts the biochemical properties of the biomarker. Thus, where mutations are introduced to substitute amino acid residues, positively-charged residues (H, K and R) preferably are substituted with positively-charged residues; negatively-charged residues (D and E) are preferably substituted with negatively-charged residues; neutral polar residues (C, G, N, Q, S, T, and Y) are preferably substituted with neutral polar residues; and neutral non-polar residues (A, F, I, L, M, P, V, and W) are preferably substituted with neutral non-polar residues.

As used herein, the amino acid residues are abbreviated as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His; H), isoleucine (Ile;I), leucine (Leu;L), lysine (Lys;K), methionine (Met;M), phenylalanine (Phe;F), proline (Pro;P), serine (Ser;S), threonine (Thr;T), tryptophan (Trp;W), tyrosine (Tyr;Y), and valine (Val;V).

In the broadest sense, the naturally occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys or Pro. By "hydrophilic" amino acid is meant either Gly, Asn, Gln, Ser, Thr, Asp, Glu, Lys, Arg or His. This grouping of amino acids can be further subclassed as follows. By "uncharged hydrophilic" amino acid is meant either Ser, Thr, Asn or Gln. By "acidic" amino acid is meant either Glu or Asp. By "basic" amino acid is meant either Lys, Arg or His.

In the past, studies have been done to identify proteins in the blood of a subject that could be used as markers for cardiovascular disease (see, e.g., Stanley et al., *Dis. Markers* 20:167-178, 2004). However, this approach has been hampered by the vast number of candidate proteins in blood plasma, in concentrations that vary over six orders of magnitude, which complicate the discovery and validation processes (Qian, W. J., et al., *Proteomics* 5:572-584, 2005). Cholesterol is present in the blood as free and esterified cholesterol within lipoprotein particles, commonly known as chylomicrons, very low density lipoproteins (VLDLs) low density lipoproteins (LDLs) and high density lipoproteins (HDLs). HDL particles vary in size and density due to the differences in the number of apolipoproteins on the surface of the particles and the amount of cholesterol esters in the core of HDL (see Asztaloe et al., *Am. J. Cardiol.*, 91:12 E-17E, 2003). HDL is composed of two principal subfractions based on density: $HDL_2$ and the denser $HDL_3$.

Elevated LDL cholesterol and total cholesterol are directly related to an increased risk of cardiovascular disease. See Anderson, Castelli, and Levy, "Cholesterol and Mortality: 30 years of Follow Up from the Framingham Study," *JAMA* 257:2176-90, 1987. In contrast, it has been established that the risk of cardiovascular disease is inversely proportional to plasma levels of HDL and the major HDL apolipoprotein, ApoA-I (Gordon, D. J., et al., *N. Engl. J. Med.* 321:1311-1316, 1989). Studies have shown that high HDL levels are associated with longevity (Barzilai, N., et al., *JAMA* 290: 2030-2040, 2003). Consistent with these findings, an abnormally low HDL level is a well-accepted risk factor for the development of clinically significant atherosclerosis (particularly common in men with premature atherosclerosis (Gordon, D. J., et al., *N. Engl. J. Med.* 321:1311-1316, 1989; Wilson, P. W., et al., *Arteriosclerosis* 8:737-741, 1988)). The mechanism by which HDL renders its protective effect against atherosclerosis is the subject of continued debate. Some studies have implicated that HDL may directly protect against atherosclerosis by removing cholesterol from artery wall macrophages (see Tall, A. R., et al., *J. Clin. Invest.* 110:899-904, 2002; Oram, J. F., et al., *Arterioscler. Thromb. Vasc. Biol.* 23:720-727, 2003). Other studies have reported that HDL protects against LDL oxidative modification, which is believed to be central to the initiation and progression of atherosclerosis (see, e.g., Parthasarathy, S., et al., *Biochim. Biophys. Acta,* 1044:275-283, 1990; Barter, P. J., et al., *Circ Res* 95: 764-772, 2004). However, while HDL/LDL ratios have been correlated with risk for cardiovascular disease on an overall population, HDL and/or LDL measurements have not been reliable indicators of risk at an individual level.

The present inventor has reduced the complexity of a whole serum analysis by identifying novel biomarkers associated with a subset of proteins associated with high density lipoprotein ("HDL") that are correlated with the presence and/or risk of cardiovascular disease ("CVD"). HDL-associated proteins include proteins in protein complexes that have the same density as HDL, and protein complexes including ApoA-I and/or ApoA-II, the major protein components of HDL. The novel biomarkers associated with CVD were identified through the use of proteomic pattern analysis of HDL or ApoA-I or ApoA-II containing complexes by mass spectrometry (MS). Using the MS-based approach, the mass spectra generated from a set of HDL samples obtained from test populations were analyzed to identify diagnostic patterns comprising a subset of key mass-to-charge (m/z) species and their relative intensities, as further described in EXAMPLES 1-8 and shown in FIGS. 1-5C. The identification of HDL-associated proteins that are present in subjects suffering from cardiovascular disease in amounts that differ from normal subjects provide new biomarkers which are useful in assays that are prognostic and/or diagnostic for the presence of cardiovascular disease and related disorders. The biomarkers may also be used in various assays to assess the effects of exogenous compounds for the treatment of cardiovascular disease.

In one aspect, the present invention provides a diagnostic test for characterizing a subject's risk of developing or currently suffering from CVD. The diagnostic test measures the level of HDL-associated proteins in a biological sample, or HDL subfraction thereof, or ApoA-I or ApoA-II containing complexes. The level of HDL-associated protein or proteins from the subject is then compared to a predetermined value that is derived from measurements of the HDL-associated protein(s) or ApoA-I or ApoA-II containing complexes in comparable biological samples from a control population, such as a population of apparently healthy subjects. The results of the comparison characterizes the test subject's risk of developing CVD. A difference in the amount of the biomarker between the subject's sample and the predetermined value, such as an average value measured from the control population, is indicative of the presence or risk of developing cardiovascular disease in the subject. In some embodiments, the method further comprises determining whether the mammalian subject is exhibiting symptoms related to CVD, as further described in EXAMPLE 4.

In one embodiment, the present invention provides an method of determining a mammalian test subject's risk of developing and or suffering from CVD. For example, the method includes the step of measuring the amount of ApoC-IV in a biological sample isolated from the subject and comparing the amount of ApoC-IV detected in the subject to a predetermined value to determine if the subject is at greater risk of developing or suffering from CVD than subjects with an amount of ApoC-IV that is at, or lower than the predetermined value. Moreover, the extent of the difference between the test subject's ApoC-IV level in the biological sample and the predetermined value is also useful for characterizing the extent of the risk, and thereby determining which subjects would most greatly benefit from certain therapies.

In another aspect, the present invention includes the step of determining the level of at least one or more biomarkers selected from the group consisting of ApoC-IV, PON-1, C3, C4, ApoA-IV, ApoE, ApoL-1, C4B1, Histone H2A, ApoC-II or ApoM, Vitronectin, Haptoglobin-related Protein and Clusterin, or portions or derivatives thereof. The detected amount of the biomarker is then compared to one or more predetermined values of the biomarker(s) measured in a control population of apparently healthy subjects.

The methods of this aspect of the invention are useful to screen any mammalian subject, including humans, non-human primates, canines, felines, murines, bovines, equines, and porcines. A human subject may be apparently healthy, or may be diagnosed as having a low HDL:LDL ratio and/or as being at risk for CVD based on certain known risk factors such as high blood pressure, high cholesterol, obesity, or genetic predisposition for CVD. The methods described herein are especially useful to identify subjects that are at high risk of developing CVD in order to determine what type of therapy is most suitable and to avoid potential side effects due to the use of medications in low risk subjects. For example, prophylactic therapy is useful for subjects at some risk for CVD, including a low fat diet and exercise. For those at higher risk, a number of drugs may be prescribed by physicians, such as lipid-lowering medications as well as medications to lower blood pressure in hypertensive patients. For subjects at high risk, more aggressive therapy may be indicated, such as administration of multiple medications.

In order to conduct sample analysis, a biological sample containing HDL-associated proteins or a complex containing ApoA-I or ApoA-II is provided to be screened. Any HDL-associated protein-containing sample or containing ApoA-I or ApoA-II complexes can be utilized with the methods described herein, including, but not limited to, whole blood or blood fractions (e.g., serum), bodily fluid, urine, cultured cells, tissue biopsies, or other tissue preparations. In some embodiments of the method of the invention, the biological samples include total HDL (density=about 1.06 to about 1.21 g/mL), or protein complexes that are isolated in this density range. In other embodiments of the method of the invention, an $HDL_2$ or $HDL_3$ subfraction (density=about 1.06 to about 1.11 g/mL, and about 1.11 to about 1.21 g/mL, respectively)

is isolated from the biological sample prior to analysis. The HDL$_3$ fraction may be isolated using any suitable method, such as, for example, through the use of ultracentrifugation, as described in EXAMPLE 1. In some embodiments of the method of this aspect of the invention, the HDL-associated proteins ApoA-I and/or ApoA-II are isolated from the biological sample using liquid chromatography, affinity chromatography, or antibody-based methods. In some embodiments, one or more of the biomarkers ApoC-IV, PON-1, C3, C4, ApoA-IV, ApoE, ApoL-1, C4B1, Histone H2A, ApoC-II, or ApoM are isolated by liquid chromatography, affinity chromatography or antibody-based methods from biological samples such as, but not limited to, blood, plasma, serum, urine, tissue, or atherosclerotic lesions.

The present inventor has identified a set of HDL-associated proteins and/or ApoA-1-associated and/or ApoA-II-associated proteins that are present in an amount that differs in subjects with CVD in comparison to control subjects, and, therefore, serve as biomarkers that are indicative of the presence and/or risk of developing cardiovascular disease in a subject. A single biomarker or combination of biomarkers (biomarker profile) may be used in accordance with the method of the invention. The biomarkers useful in the method of the invention, listed below in TABLE 1, were identified by comparing mass spectra of HDL-associated proteins derived from CVD subjects with HDL-associated proteins derived from normal subjects, as described in EXAMPLES 4-8. The CVD subjects used to identify the biomarkers shown in TABLE 1 were diagnosed according to standard clinical criteria as described in EXAMPLE 4 and TABLE 2.

TABLE 1

BIOMARKERS USEFUL AS PROGNOSTIC AND/OR DIAGNOSTIC INDICATORS OF CARDIOVASCULAR DISEASE

| Protein | SEQ ID NO: |
|---|---|
| ApoC-IV | SEQ ID NO: 1 |
| Paraoxonase 1 (PON-1) | SEQ ID NO: 2 |
| Complement C3 | SEQ ID NO: 3 |
| ApoA-IV | SEQ ID NO: 4 |
| ApoE | SEQ ID NO: 5 |
| ApoL-I | SEQ ID NO: 6 |
| C4B1 (a haplotype of C4) | SEQ ID NO: 7 |
| Histone H2A | SEQ ID NO: 8 |
| ApoC-II | SEQ ID NO: 9 |
| ApoM | SEQ ID NO: 10 |
| C3dg (aa 954-1303 of C3) | SEQ ID NO: 11 |
| Vitronectin | SEQ ID NO: 12 |
| Haptoglobin-related Protein | SEQ ID NO: 13 |
| Clusterin | SEQ ID NO: 14 |
| Complement C4 | SEQ ID NO: 15 |

The HDL-associated biomarkers shown above in TABLE 1 were identified using various methods, including mass spectrometry and antibody detection methods, as described in EXAMPLES 1-9 and as shown in FIGS. 2A-5C. A total of 35 HDL-associated proteins were identified in samples obtained from control subjects and subjects with CVD, as described in EXAMPLE 5 and shown in TABLE 3. In order to empirically assess the relative abundance of the HDL-associated proteins in subjects with CVD and control subjects, a peptide index ("PI") was used as follows. For each protein identified by mass spectrometry, the following parameters were determined: (1) the number of peptides corresponding to the protein that were identified in normal subjects, (2) the number of peptides corresponding to the protein that were identified in CVD subjects, (3) the total number of peptides that were identified, (4) the percent of normal subjects in which at least one peptide was identified, and (5) the percent of CVD subjects in which at least one peptide was identified.

Using these parameters, the peptide index ("PI") is calculated as follows:

PI=[(peptides in CVD subjects/total peptides)×(% of CVD subjects with 1 or more peptides)]−[(peptides in control subjects/total peptides)×(% of control subjects with 1 or more peptides)].

Using this calculation, a value of "0" indicates that the numbers of peptides and subjects with detectable peptides are about equal in CVD subjects and healthy controls. A positive peptide index value correlates with enrichment of peptides derived from the protein of interest in CVD patients; whereas, a negative peptide index value correlates with enrichment in healthy control subjects. The parameters used to calculate the peptide index for each HDL-associated protein are provided below in TABLE 3. The peptide index calculated for each HDL-associated protein is shown in TABLE 5. In one embodiment, the biomarkers associated with an increased risk of developing or suffering from CVD are present at an increased amount in subjects with CVD in comparison to normal controls having a peptide index of equal to or greater than 0.30, more preferably greater than 0.35, more preferably greater than 0.40, more preferably greater than 0.50, more preferably greater than 0.60, such as greater than 0.70, such as greater than 0.80. In another embodiment, biomarkers associated with CVD are found to be absent, or at a reduced abundance in subjects with CVD in comparison to normal controls and have a peptide index of equal to or less than −0.30. The HDL-associated proteins that are equally abundant in CVD and normal subjects, such as ApoA-I and ApoA-II, have a peptide index value ranging from about 0.20 to about −0.20 and may be used as controls in the various embodiments of the methods of the invention.

In accordance with one embodiment of this aspect of the invention, HDL-associated biomarkers comprising ApoC-IV, PON-1, C3, C4, ApoA-IV, ApoE, ApoL1, C4B1, histone H2A, ApoC-II, ApoM, and derivatives and/or peptides thereof, are present at an increased amount in subjects with CVD as compared to control subjects. Apolipoprotein C-IV, PON-1, C3, C4, ApoA-IV, ApoE, ApoL1, C4B1 C4B1, Histone H2A, ApoC-II, and ApoM, were found as HDL-associated proteins enriched in the HDL$_3$ fraction of biological samples from CVD as compared to the HDL$_3$ fraction from biological samples taken from control subjects, as shown in TABLE 3, TABLE 5, and FIG. 3.

In accordance with this aspect of the invention, proteins having at least 70% homology (such as at least 80% identical, or such as at least 90% identical, or such as at least 95% identical) with ApoC-IV (SEQ ID NO:1), PON-1 (SEQ ID NO:2), C3 (SEQ ID NO:3), ApoA-IV (SEQ ID NO: 4), ApoE (SEQ ID NO: 5), ApoL-1 (SEQ ID NO:6), C4B1 (SEQ ID NO:7), Histone H2A (SEQ ID NO:8), ApoC-II (SEQ ID NO:9), and ApoM (SEQ ID NO:10) may be used as biomarkers for CVD which are present at increased concentration in CVD subjects as compared to normal controls. Peptide fragments derived from SEQ ID NOS:1, 2, 3, 4, 5, 6, 7, 8, 9, and 10 may also be used as biomarkers, such as peptides from about 4 amino acids to at least about 50 amino acids, such as peptides from about 6 amino acids to at least about 20 amino acids or more. Representative examples of peptide fragments that may be used as biomarkers in which an increased amount of the biomarker in HDL$_3$ is indicative of the presence or risk of CVD include SEQ ID NO:16-SEQ ID NO:126, shown below in TABLE 5.

In accordance with another embodiment of this aspect of the invention, HDL-associated proteins comprising Vitronectin, Haptoglobin-related protein and Clusterin, and derivatives and/or peptides thereof are present at a reduced amount in subjects with CVD as compared to control subjects. Vitronectin, Clusterin and Haptoglobin-related protein were found as HDL-associated proteins in the $HDL_3$ fraction of samples from normal subjects, but were not detected, or were found to be present at lower levels, in $HDL_3$ derived from the patients with CVD, as shown in TABLE 3, TABLE 5 and FIG. 3. In accordance with this aspect of the invention, proteins having at least 70% homology (such as at least 80% identical, or such as at least 90% identical, or such as at least 95% identical) with Vitronectin (SEQ ID NO:12), Haptoglobin-related protein (SEQ ID NO:13) or Clusterin (SEQ ID NO:14) may be used as biomarkers for CVD which are present at reduced concentration in CVD subjects as compared to normal controls. Peptide fragments derived from SEQ ID NOS:12, 13 or 14 may also be used as biomarkers, such as peptides at least about 4 amino acids to at least about 20 amino acids, such as peptides from about 6 amino acids to about 20 amino acids or more. Representative examples of peptide fragments that may be used as biomarkers in which a reduced amount of the biomarker in $HDL_3$ is indicative of the presence or risk of CVD include SEQ ID NOS:127-159 as shown below in TABLE 5.

The presence and/or amount of the one or more HDL-associated biomarkers in a biological sample comprising total HDL, or a subfraction thereof, and/or an ApoA-I and/or an ApoA-II containing complex may be determined using any suitable assay capable of detecting the amount of the one or more biomarker(s). Such assay methods include, but are not limited to, mass spectrometry, liquid chromatography, thin layer chromatography, fluorometry, radioisotope detection, affinity detection, and antibody detection. Other detection paradigms may optionally be used, such as optical methods, electrochemical methods, atomic force microscopy, and radio frequency methods (e.g., multipolar resonance spectroscopy). Optical methods include, for example, microscopy, detection of fluorescence, luminescence, chemiluminescence, absorbance, reflectance, and transmittance.

In one embodiment, the presence and amount of one or more HDL-associated biomarkers is determined by mass spectrometry. In accordance with this embodiment, biological samples may be obtained and used directly, or may be separated into total HDL, or an $HDL_3$ subfraction. The HDL-associated proteins are digested into peptides with any suitable enzyme such as trypsin, which cleaves adjacent to lysine (K) or arginine (R) residues in proteins. The peptides are then analyzed by a mass spectrometry method such as MALDI-TOF-MS or M/MS (solid phase), liquid chromatography (LC)-MS or MS/MS, μLC-ESI-MS/MS, and iTRAQ™, ICAT, or other forms of isotope tagging. Any suitable method may be used for differential isotope labeling of proteins and/or peptide, such as the use of a compound or isotope-labeled compound that reacts with an amino acid functional group. Label-specific fragment ions allow one to quantify the differences in relative abundance between samples. For example, one useful approach to achieve quantitative results, is the use of MALDI TOF/TOF or QTOF mass spectrometers and iTRAQ™, a commercially available stable isotope labeling system (Applied Biosystems, Foster City, Calif.). The iTRAQ™ labeling system allows selective labeling of up to four different samples which are distinguished from one another in the mixture by MS/MS analysis.

By way of representative example, the method of μLC-ESI-MS/MS involves the following steps. The peptide mixtures are resolved by microscale liquid chromatography, and peptides are ionized by electrospray. Mass spectra are taken every few seconds, followed by isolation of the most intense peptide ions, or the peptide ions of interest (e.g., one derived from specific peptides), fragmentation by collisions with an inert gas, and recording of a mass spectrum of the fragments. This fragment mass spectrum, known as MS/MS spectrum, tandem mass spectrum, or $MS^2$ spectrum, consists mainly of N- and C-terminal fragments of the peptide ions at the amide bonds, called b ions and y ions, respectively. The spectra are then matched to sequence databases, as further described in EXAMPLE 4.

In a typical application of MS analysis, proteins in a biological sample are reduced, alkylated, digested into peptides with trypsin, and analyzed using multidimensional liquid chromatography and tandem mass spectrometry (MS/MS). Tryptic peptides are then subjected to multidimensional chromatography in concert with MS/MS analysis. In multidimensional chromatography, the first chromatographic dimension typically involves separation of digested peptides on a strong cation exchange column. The peptides are then typically separated through a reverse-phase column with increasing concentrations of acetonitrile and then introduced into the source of the mass spectrometer or fractionated directly onto a MALDI sample plate. Tandem mass spectra may be acquired in the data-dependent mode on an ion-trap, QTOF or MALDI-TOF/TOF instrument. The most abundant peaks from a survey scan are submitted to tandem MS analysis. In other applications, peaks that differ in intensity between samples of interest (e.g., a control population of apparently healthy subjects and subjects with established CVD) are selected from the MS or MS/MS spectra by a suitable method such as pattern recognition (ref)., cluster analysis, or relative abundance (see Rocke D. M, *Semin Cell Dev Biol*, 15: 703-13, 2004; Ghazalpour A., et al., *Lipid Res* 45: 1793-805, 2004). The collection of tandem mass spectra may be submitted for a database search against a database (e.g., the Human International Protein Index (IPI) database, using the SEQUEST search engine (see Kersey, P. J., et al., "The International Protein Index: an integrated database for proteomics experiments," *Proteomics* 4:1985-1988, 2004)), using software programs such as PeptideProphet, (Nesvizhskii, A. I., et al., *Anal. Chem.* 75:4646-4658, 2003) and ProteinProphet (Yan, W., et al., *Mol. Cell. Proteomics* 3:1039-1041, 2004) in order to refine peptide and protein identification.

To achieve semiquantitative results, protein abundance is estimated by the number of MS/MS spectra, the number of peptides detected, or by the percent of the protein sequence covered in the analysis. Quantitative results can be obtained with ICAT isotope tagging, iTRAQ™ isotope labeling, or other modifications or peptides involving stable isotopes. Label-specific ions or fragment ions allow quantification of differences between samples based on their relative abundance.

Mass spectrometry detection methods may include the use of isotope-labeled peptides or proteins. In accordance with one example of this detection method, as described by Zou, H., et al., *Cell* 107:715-726, 2001, a tryptic peptide is chosen from a protein of interest, for example, a tryptic peptide comprising a portion of SEQ ID NOS:1-15, such as SEQ ID NOS:16-175. The tryptic peptide is then synthesized to incorporate one or more stable isotope-labeled amino acids. The native peptide and the synthetic-labeled peptide share physical properties including size, charge, hydrophobicity, ionic character, and amenability to ionization. When mixed, they elute together chromatographically, migrate together electrophoretically, and ionize with the same intensity. However, they differ in molecular weight from as little as 1 to over 10 Daltons, depending on which stable isotope amino acid is chosen for incorporation. The native peptide and the synthetic peptide are easily distinguishable by mass spectrometry. The synthetic peptide is used in an assay by adding a known amount of the synthetic peptide to a biological sample. In another example of this detection method, an isotope-labeled protein is prepared by a suitable method, such as by using a bacterial expression system and growing the bacteria on medium enriched with 15N-Nitrate or other isotope-labeled nutrients. The isotope-labeled peptide or protein is added to the sample containing native proteins and the mixture is then digested and analyzed by mass spectrometry as described herein. Extracted ion chromatograms or selected ion chromatograms or peak ratios in a full scan mass spectrum are then generated for the native peptide and the synthetic peptide. The quantity of the native peptide is then calculated using ratios of ion current or peak ratios.

Another detection method that utilizes labeled peptide fragments is isotope-coded affinity tagging (ICAT). This technique, as described in Gygi, S. P., et al., *Nature Biotech.* 17:994-999, 1999, involves the use of isotope tags that covalently bind to specific amino acids (cysteines) within a protein of interest. For example, the tag may contain three functional elements including a biotin tag (used during affinity capture), an isotopically encoded linker chain (such as an ether linkage with either eight hydrogens or eight deuteriums), and the reactive group, which binds to and modifies the cysteine residues of the protein. The isotope tag is used in an assay by labeling a control sample with the light version of the tag and labeling a test sample with the heavy version of the tag. The two samples are then combined, enzymatically digested, and the labeled cysteinyl residues may be captured using avidin affinity chromatography. The captured peptides are then analyzed by mass spectrometry, which can determine the relative abundance for each peptide-pair.

Figure 4:
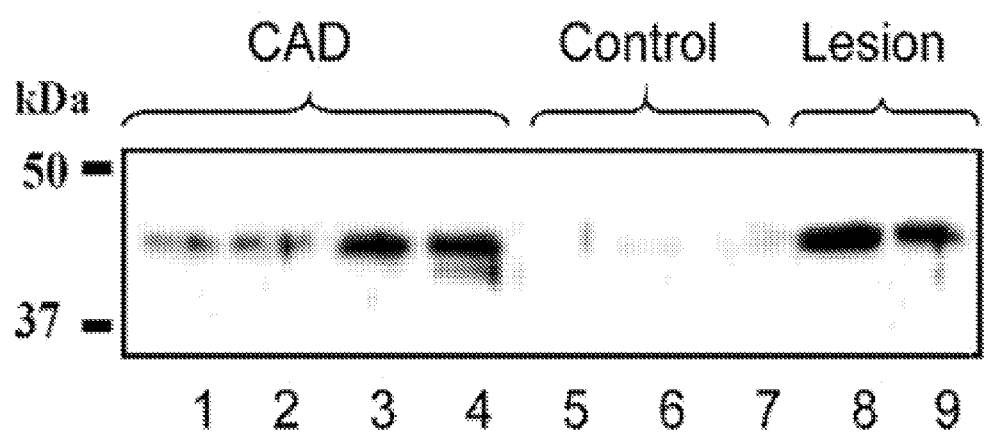
FIG. 4 presents Western blot data demonstrating that Paraoxonase ("PON-1") is present at detectable levels in $HDL_3$ isolated from plasma obtained from four patients with CVD (lanes 1-4) and in $HDL_3$ isolated from atherosclerotic lesions obtained from two subjects with CVD (lanes 8-9), but is not detectable in $HDL_3$ isolated from plasma obtained from three normal control subjects (lanes 5-7), as described in EXAMPLE 6.

In another embodiment, antibodies are used in an immunoassay to detect one or more biomarkers in accordance with the method of this aspect of the invention. Such immunoassays may comprise an antibody to one or more of the biomarkers. The antibody is mixed with a sample suspected of containing the biomarker and monitored for biomarker-antibody binding. For example, the biomarker can be detected in an enzyme-linked immunosorbent assay (ELISA), in which a biomarker antibody is bound to a solid phase, such as a chip, and an enzyme-antibody conjugate is used to detect and/or quantify the biomarker(s) present in a sample. Alternatively, a Western blot assay may be used in which a solubilized and separated biomarker is bound to nitrocellulose filter, as shown in FIG. 4 and described in EXAMPLES 4, 7, and 8.

In one embodiment, the invention provides a method for diagnosing and/or assessing the risk of CVD in a subject, comprising determining changes in a biomarker profile comprising the relative abundance of at least one, two, three, four, five, ten or more HDL-associated and/or ApoA-I or ApoA-II-associated biomarkers in biological samples from a test subject as compared to the predetermined abundance of the at least one, two, three, four, five, ten or more HDL-associated biomarkers and/or ApoA-I or ApoA-II biomarkers from a reference population of apparently healthy subjects. The HDL-associated biomarkers and/or ApoA-I or ApoA-II associated markers are selected from the group consisting of the biomarkers listed in TABLE 1 and TABLE 5. The biomarker profile may optionally include an internal reference standard that is expected to be equally abundant in subjects with CVD and apparently healthy subjects, such as ApoA-I or ApoA-II, and fragments thereof.

In another aspect, the present invention provides a method for screening a mammalian subject for the presence of one or more atherosclerotic lesions in the subject by detecting an amount of at least one biomarker in a blood sample. The invention provides biomarkers that are capable of identifying the presence of one or more atherosclerotic plaques in a subject, including PON-1, C3, C4, ApoE, ApoM and C4B1.

In the arterial disease atherosclerosis, fatty lesions form on the inside of the arterial wall. These lesions promote the loss of arterial flexibility and lead to the formation of blood clots. The lesions may also lead to thrombosis, resulting in most acute coronary syndromes. Thrombosis results from weakening of the fibrous cap, and thrombogenicity of the lipid core. It is well recognized that atherosclerosis is a chronic inflammatory disorder (see Ross, R., *N. Engl. J. Med.* 340:115-126, 1999). Chronic inflammation alters the protein composition of HDL, making it atherogenic (see Barter, P. J., et al., *Circ. Res.* 95:764-772, 2004; Chait, A., et al., *J. Lipid Res.* 46:389-403, 2005; Navab, M., et al., *J. Lipid Res.* 45:993-1007, 2004; and Ansell, B. J., et al., *Circulation* 108:2751-2756, 2003). However, the discovery of markers for cardiovascular disease, including atherosclerosis, has been hampered by the molecular complexity of plasma.

The present inventor has discovered that five of the ten described HDL-associated biomarkers that were found to be enriched in $HDL_3$ from CVD subjects were also found in the HDL isolated from human atherosclerotic lesions, referred to hereafter as "lesion HDL," including PON-1, C3, C4, ApoE, ApoM and C4B1, as shown in FIG. 4 and TABLE 6. While not wishing to be bound by theory, these results suggest that some of the protein cargo of circulating HDL in CVD patients may originate from diseased regions of artery walls. Accordingly, HDL-associated proteins that serve as biomarkers for CVD, and atherosclerotic lesions in particular, may be derived from macrophages, smooth muscle cells, and endothelial cells present in atherosclerotic lesions. In accordance with this aspect of the invention, HDL-associated biomarkers isolated from a blood sample represent a biochemical "biopsy" of the artery wall or endothelium lining the vasculature. It is likely that lesions that are most prone to rupture would increase their output of HDL due to the fact that enhanced proteolytic activity destroys the extracellular matrix and promotes plaque rupture. Indeed, short-term infusion of HDL into humans may promote lesion regression (Nissen, S. E., et al., *JAMA* 290:2292-2300, 2003), suggesting that HDL can remove components of atherosclerotic tissue. Therefore, the proteins included in the protein cargo associated with HDL, enriched in CVD subjects, and also known to be present in lesion HDL from a population of CVD patients, serve as biomarkers that may be used to detect the risk and/or presence of atherosclerotic plaques in an individual subject.

In accordance with this aspect of the invention, proteins having at least 70% homology (such as at least 80% identical, or such as at least 90% identical, or such as at least 95% identical) with PON-1 (SEQ ID NO:2), C3 (SEQ ID NO:3), C4 (SEQ ID NO: 15), ApoE (SEQ ID NO:5), ApoM (SEQ ID NO:10), or C4B1 (SEQ ID NO:7) may be used as biomarkers for the presence of one or more atherosclerotic lesions when present at increased amounts in $HDL_3$ in a biological sample isolated from a subject in comparison to the amount detected in a control population. Peptide fragments derived from SEQ ID NOS:2, 3, 5, 7, 10, or 15 may also be used as biomarkers, such as peptides having at least about 4 amino acids to at least about 20 amino acids, such as peptides from about 6 amino acids to about 20 amino acids or more. Representative examples of peptide fragments that may be used as biomarkers in which an increased amount of the biomarker in $HDL_3$ is indicative of the presence of one or more atherosclerotic lesions includes SEQ ID NOS:23-49, SEQ ID NOS:68-82, SEQ ID NOS:93-113, and SEQ ID NOS:122-126, as shown below in TABLE 5.

In another aspect, the present invention provides assays comprising one or more detection reagents capable of detecting at least one biomarker that is indicative of the presence or risk of CVD in a subject. The biomarker is detected by mixing a detection reagent that detects at least one biomarker associated with CVD with a sample containing HDL-associated proteins and monitoring the mixture for detection of the biomarker with a suitable detection method such as spectrometry, immunoassay, or other method. In one embodiment, the assays are provided as a kit. In some embodiments, the kit comprises detection reagents for detecting at least two, three, four, five, ten or more HDL-associated biomarkers in biological samples from a test subject.

The kit also includes written indicia, such as instructions or other printed material for characterizing the risk of CVD based upon the outcome of the assay. The written indicia may include reference information, or a link to information regarding the predetermined abundance of the at least one, two, three, four, five, ten or more HDL-associated biomarkers from a reference population of apparently healthy subjects and an indication of a correlation between the abundance of one or more HDL-associated biomarkers and the risk level and/or diagnosis of CVD.

The detection reagents may be any reagent for use in an assay or analytical method, such as mass spectrometry, capable of detecting at least one biomarker selected from the group consisting of ApoC-IV, PON-1, C3, C4, ApoA-IV, ApoE, ApoL-1, C4B1, Histone H2A, ApoC-II, ApoM, C3dg, C4, Vitronectin, Haptoglobin-related protein, and Clusterin. In another embodiment, the detection reagents include proteins with peptides identical to those of ApoC-IV, PON-1, C3, C4, ApoA-IV, ApoE, ApoL-1, C4B1, Histone H2A, ApoC-II, ApoM, C3dg, C4, Vitronectin, Haptoglobin-related protein, and Clusterin, such as peptides provided in TABLE 5. In one embodiment, the detection reagents comprise one or more reagents capable of detecting a biomarker associated with the presence of one or more atherosclerotic lesions, such as PON-1, C3, C4, ApoE, ApoM, and C4B1. A variety of protocols for measuring the relative abundance of the biomarkers may be used, including mass spectrometry, ELISAs, RIAs, and FACs, which are well known in the art.

In one embodiment, the detection reagent comprises one or more antibodies which specifically bind one or more of the biomarkers provided in TABLE 4, TABLE 5 or TABLE 6 that may be used for the diagnosis and/or prognosis of CVD characterized by the relative abundance of the biomarker in the serum, or an HDL subfraction thereof. Standard values for protein levels of the biomarkers are established by combining biological samples taken from healthy subjects, for example, by using criteria described in EXAMPLE 4, with antibodies to proteins determined to have a PI value of between 0.20 and −0.20, such as ApoA-I (PI=0.08) and ApoA-II (PI=0.06). Deviation in the amount of the biomarker between control subjects and CVD subjects establishes the parameters for diagnosing and/or assessing risk levels, or monitoring disease progression. The biomarkers and fragments thereof can be used as antigens to generate antibodies specific for the CVD biomarkers for use in immunodiagnostic assays. Purified samples of the biomarkers comprising the amino acid sequences shown in TABLE 4, TABLE 5, and TABLE 6 may be recovered and used to generate antibodies using techniques known to one of skill in the art.

In another embodiment, the detection reagent comprises isotope-labeled peptides, such as one or more of the peptides described in TABLE 4, TABLE 5, and TABLE 6 that correspond to the biomarker to be detected. In accordance with this embodiment, the kit includes an enzyme, such as trypsin, and the amount of the biomarker in the tryptic digest of the sample is then quantified by isotope dilution mass spectrometry. The labeled peptides may be provided in association with a substrate, and the assay may be carried out in a multiplexed format. In one embodiment, a multiplexed format includes isotope-labeled peptides for at least two or more of the HDL-associated biomarkers described herein that are enriched in HDL of subjects with established CVD. The peptides are quantified of all the HDL-associated peptides in a biological sample obtained from a test subject using a technique such as isotope dilution mass spectrometry. The detection and quantification of multiple HDL-associated biomarker proteins may be used to increase the sensitivity and specificity of the assay to provide an accurate risk assessment and/or diagnosis of the presence of CVD in the test subject.

In one embodiment of the kit, the detection reagent is provided in association with, or attached to a substrate. For example, a sample of blood, or HDL subfraction thereof, may be contacted with the substrate, having the detection reagent thereon, under conditions that allow binding between the biomarker and the detection reagent. The biomarker and/or the detection reagent are then detected with a suitable detection method. The substrate may be any suitable rigid or semi-rigid support including membranes, filters, chips, slides, wafers, fibers, magnetic or nonmagnetic beads, gels, tubing, plates, polymers, microparticles, and capillaries. The substrate can have a variety of surface forms, such as wells, trenches, pins, channels, and pores to which the polypeptides are bound. For example, a chip, such as a biochip, may be a solid substrate having a generally planar surface to which a detection reagent is attached. For example, a variety of chips are available for the capture and detection of biomarkers, in accordance with the present invention, from commercial sources such as Ciphergen Biosystems (Fremont, Calif.), Packard BioScience Company (Meriden Conn.), Zyomyx (Hayward, Calif.), and Phylos (Lexington, Mass.). An example of a method for producing such a biochip is described in U.S. Pat. No. 6,225,047. The biomarkers bound to the substrates may be detected in a gas phase ion spectrometer. The detector translates information regarding the detected ions into mass-to-charge ratios. Detection of a biomarker also provides signal intensity, thereby allowing the determination of quantity and mass of the biomarker.

In another aspect, the present invention provides a method for determining the efficacy of a treatment regimen for treating and/or preventing CVD by monitoring the presence of one or more biomarkers in a subject during treatment for CVD. The treatment for CVD varies depending on the symptoms and disease progression. The general treatments include lifestyle changes, medications, and may include surgery. Lifestyle changes include, for example, weight loss, a low saturated fat, low cholesterol diet, reduction of sodium, regular exercise, and a prohibition on smoking. Medications useful to treat CVD include, for example, cholesterol-lowering medications, antiplatelet agents (e.g., aspirin, ticlopidine, clopidogrel), glycoprotein IIb-IIIa inhibitors (such as abciximab, eptifibatide or tirofiban), or antithrombin drugs (blood-thinners such as heparin) to reduce the risk of blood clots. Beta-blockers may be used to decrease the heart rate and lower oxygen use by the heart. Nitrates, such as nitroglycerin are used to dilate the coronary arteries and improve blood supply to the heart. Calcium-channel blockers are used to relax the coronary arteries and systemic arteries, and, thus, reduce the workload for the heart. Medications suitable for reducing blood pressure are also useful to treat CVD, including ACE inhibitors, diuretics and other medications.

The treatment for cardiovascular disease may include surgical interventions such as coronary angioplasty, coronary atherectomy, ablative laser-assisted angioplasty, catheter-based thrombolysis, mechanical thrombectomy, coronary stenting, coronary radiation implant, coronary brachytherapy (delivery of beta or gamma radiation into the coronary arteries), and coronary artery bypass surgery.

The following examples merely illustrate the best mode now contemplated for practicing the invention, but should not be construed to limit the invention.

Example 1

This example demonstrates the validation of a method used to identify HDL-associated protein biomarkers that correlate with cardiovascular disease, in accordance with one embodiment of the present invention.

Rationale: A proteomic approach was used to directly measure the proteins associated with HDL, also referred to as "shotgun proteomics." In order to minimize potential contamination with LDL, the lipoprotein's dense subfraction, $HDL_3$, was isolated and analyzed.

Sample isolation and preparation: All protocols involving human subjects were approved by the Human Studies Committees at the University of Washington and Wake Forest University. Blood samples were collected from healthy adult males and from male patients with CVD after an overnight fast. Blood samples were anticoagulated with EDTA.

HDL isolation: HDL (d=about 1.06 to about 1.21 g/mL) and $HDL_3$ (d=about 1.11 to about 1.21 g/mL) were isolated from the blood samples by sequential density ultracentrifugation, according to the methods described in Mendez, A. J., et al., *J. Biol. Chem.* 266:10104-10111, 1991. Protein concentration was determined using the Lowry assay with albumin as the standard (BioRad, Hercules, Calif.).

Tryptic Digest: HDL-associated protein (20 µg) was precipitated with 10% trichloroacetic acid (v/v), collected by centrifugation, and resolubilized with 100 µL of 6 M urea in 25 mM ammonium bicarbonate. Following reduction with dithiothreitol (10 mM for 1 hour at 37° C.), the proteins were alkylated with iodoacetamide (40 mM) for 1 hour in the dark. The residual alkylating reagent was scavenged with a molar excess of dithiothreitol. Reduced, alkylated proteins were resuspended in 0.6 M urea in 25 mM ammonium bicarbonate, digested overnight at 37° C. with trypsin (1:20, w/w, trypsin/HDL protein), acidified with acetic acid, dried under vacuum, and resuspended in 0.1% formic acid. Tryptic digests were desalted with a C18 zip-tip (Millipore, Billerica, Mass.) prior to MS analysis.

Multidimensional micro-liquid chromatography-electrospray ionization (ESI) tandem mass spectrometric (MS/MS) analysis (µLC-ESI-MS/MS). Peptides from the HDL samples (10 µg protein) were separated using two-dimensional micro-liquid chromatography (µLC) with a strong cation (SCX) exchange column (Hypersil Keystone, Thermo Electron Corporation, Waltham, Mass.) and a reverse-phase capillary HPLC column (180 µm×10 cm; 5 µm particles; Biobasic-18, Thermo Electron Corporation) (Link, A. J. et al., *Nat Biotechnol* 17: 676-682, 1999; Washburn, M. P. et al., *Anal Chem* 75: 5054-5061, 2003). The µLC system was interfaced with a Finnigan LCQ Deca ProteomeX ion trap mass spectrometer (Thermo Electron Corporation) equipped with an orthogonal electrospray interface. A fully automated 10-step chromatography run with a quaternary Surveyor HPLC (Thermo Electron Corporation) was performed on each sample, using buffer A (0.1% v/v formic acid in water), buffer B (100% acetonitrile in 0.1% formic acid), buffer C (5% acetonitrile in 0.1% formic acid), and buffer D (1 M ammonium chloride in buffer C). A survey scan from m/z 300 to m/z 1500 was initially performed, followed by data-dependent MS/MS analysis of the three most abundant ions. Relative collision energy was set to 35% with a 30 msec activation time.

Sequencing and identifying peptides: To identify HDL-associated proteins, MS/MS spectra were searched against the Human International Protein Index (IPI) database, using the SEQUEST search engine (see Kersey, P. J., et al., "The International Protein Index: an integrated database for proteomics experiments," *Proteomics* 4:1985-1988, 2004). The SEQUEST database searches were carried out using 2.5 Da (average) peptide mass tolerance and 1.0 Da (average) fragment ion mass tolerance. One incomplete cleavage site was allowed in peptides. Threshold Xcorr values of 2.56, 3.22, and 3.45 were employed for $MH^{1+}$, $MH^{2+}$, and $MH^{3+}$ ion charge states, respectively.

The SEQUEST results were further processed using PeptideProphet (Nesvizhskii, A. I., et al., *Anal. Chem.* 75:4646-4658, 2003) and ProteinProphet (Yan, W., et al., *Mol. Cell. Proteomics* 3:1039-1041, 2004). Peptide matches were accepted only with an adjusted probability of >0.9; for proteins, the accepted probability was >0.8. All protein identifications required detection of at least 2 unique peptides from each protein from at least 2 individuals. MS/MS spectra from proteins identified with <6 peptides were confirmed by visual inspection.

Example 2

This example demonstrates that shotgun proteomics may be used to reproducibly identify proteins associated with HDL from blood, and that the HDL from healthy subjects and from subjects with established CVD carry different associated protein cargo.

Methods: Using sequential density gradient ultracentrifugation, HDL (d=about 1.060 to about 1.21 g/mL) was isolated from the blood plasma of two apparently healthy men and from two men with established CVD, using the methods described in EXAMPLE 1. HDL proteins in each sample were precipitated with trichloroacetic acid, digested with trypsin and desalted. Each digest was then subjected to four µLC-ESI-MS/MS analyses with an ion trap instrument as described in EXAMPLE 1. Proteins were identified as described in EXAMPLE 1.

Results: FIG. 1 shows the results of the four separate analyses of the two samples taken from control individuals and two samples taken from individuals with CVD. As shown in FIG. 1, the µLC-ESI-MS/MS analysis of the HDL from the two control subjects identified about 24 proteins; whereas, analysis of the HDL from the two subjects with CVD identified about 40 proteins. The variation between the four replicates in each set was approximately 20%.

Conclusions: These observations indicate that the protein composition of HDL differs substantially in subjects with CVD as compared to the protein composition of HDL isolated from control subjects. These results also demonstrate that a single analysis of HDL by µLC-ESI-MS/MS provides a reasonable estimate of the number of proteins present, and that the results obtained using µLC-ESI-MS/MS analysis are reproducible.

Example 3

This example describes the identification of particular HDL-associated proteins present in the $HDL_3$ subfraction isolated from normal control subjects and subjects with CVD.

Rationale: In order to further investigate the protein composition of HDL in control subjects and subjects with CVD, the HDL$_3$ subfraction was isolated to minimize potential contamination with LDL.

Methods:

Subjects Used in the Study:

HDL$_3$ was isolated from the blood samples of 7 men with established CVD and from blood samples obtained from 6 apparently healthy age-matched control subjects mean age±SD, 54±7, and 54±14 years, respectively.

The CVD patients were newly diagnosed, as documented by clinical symptoms consistent with angina and q waves on their EKG, or at least one stenotic lesion [>50%] on coronary angiography. None of the subjects smoked cigarettes, nor did they have liver or renal disease. The subjects did not receive any lipid-lowering medications for at least 8 weeks before blood samples were collected. The healthy controls had no known history of CVD, had no family history of CVD, and were not hyperlipidemic or diabetic. Lipid values in the CVD subjects and healthy control subject are summarized below in TABLE 2.

TABLE 2

CHARACTERISTICS OF CONTROL SUBJECTS AND CVD SUBJECTS.

| Characteristic | Controls | CVD Patients | P Value |
| --- | --- | --- | --- |
| Age - years | 54 ± 14 | 54 ± 7 | 0.97 |
| Cholesterol | 188 ± 39 | 231 ± 31 | 0.05 |
| LDL | 126 ± 30 | 161 ± 19 | 0.03 |
| Triglycerides | 91 ± 13 | 189 ± 101 | 0.04 |
| HDL | 44.8 ± 12 | 39.6 ± 11 | 0.52 |

Values represent mean ± SD.
Lipid values are in mg/dL.

As shown in TABLE 2, the patients with CVD had higher levels of total cholesterol, LDL and triglycerides in their plasma as compared with the healthy control subjects. Importantly, the levels of HDL cholesterol were similar in the CVD patients and the control subjects.

Isolation of HDL:

HDL$_3$ (d=about 1.11 to about 1.21 g/mL) was isolated by sequential density gradient ultracentrifugation using the methods described above in EXAMPLE 1. Preliminary experiments showed that extracting lipids from HDL significantly diminished the complexity of the associated protein mixture, likely because some HDL-associated proteins can dissolve in organic solvents. Therefore, the intact lipoprotein was first precipitated with trichloroacetic acid before digesting it with trypsin, and the desalted proteolytic digest was directly injected onto the strong-cation exchange column of the µLC system. Each sample was independently analyzed.

Identification of HDL-Associated Proteins:

Tryptic digests of HDL$_3$ were subjected to two-dimensional µLC-ESI-MS/MS. MS/MS spectra were searched against the Human International Protein Index (IPI) database, using the SEQUEST search engine. One incomplete cleavage site was allowed in peptides. The SEQUEST results were further processed using PeptideProphet (Nesvizhskii, A. I., et al., supra) and ProteinProphet (Yan, W., et al., *Mol. Cell. Proteomics* 3:1039-1041, 2004). Peptide matches were only accepted with an adjusted probability of >0.9. Protein identification was based on the following criteria: (i) at least 2 peptides unique to the protein of interest had to be detected in at least 2 subjects; and (ii) MS/MS results had to have a high confidence score and be chemically plausible on visual inspection. All protein identifications required detection of at least 2 unique peptides from each protein from at least 2 individuals in order to maintain a high confidence score and markedly decrease the false-positive rate of protein identification, as described in Resing, K. A., et al., *FEBS Lett.* 579: 885-889, 2005.

Results: Using µLC-ESI-MS/MS, a total of 35 proteins were identified in HDL$_3$ isolated from healthy controls and/or CVD subjects as shown below in TABLE 3, TABLE 4, and graphically displayed in FIG. 2A. The proteins shown in FIG. 2A, TABLE 3, and TABLE 4 are listed according to the peptide index (as described in more detail in EXAMPLE 5), and by statistical testing.

Figure 2A:
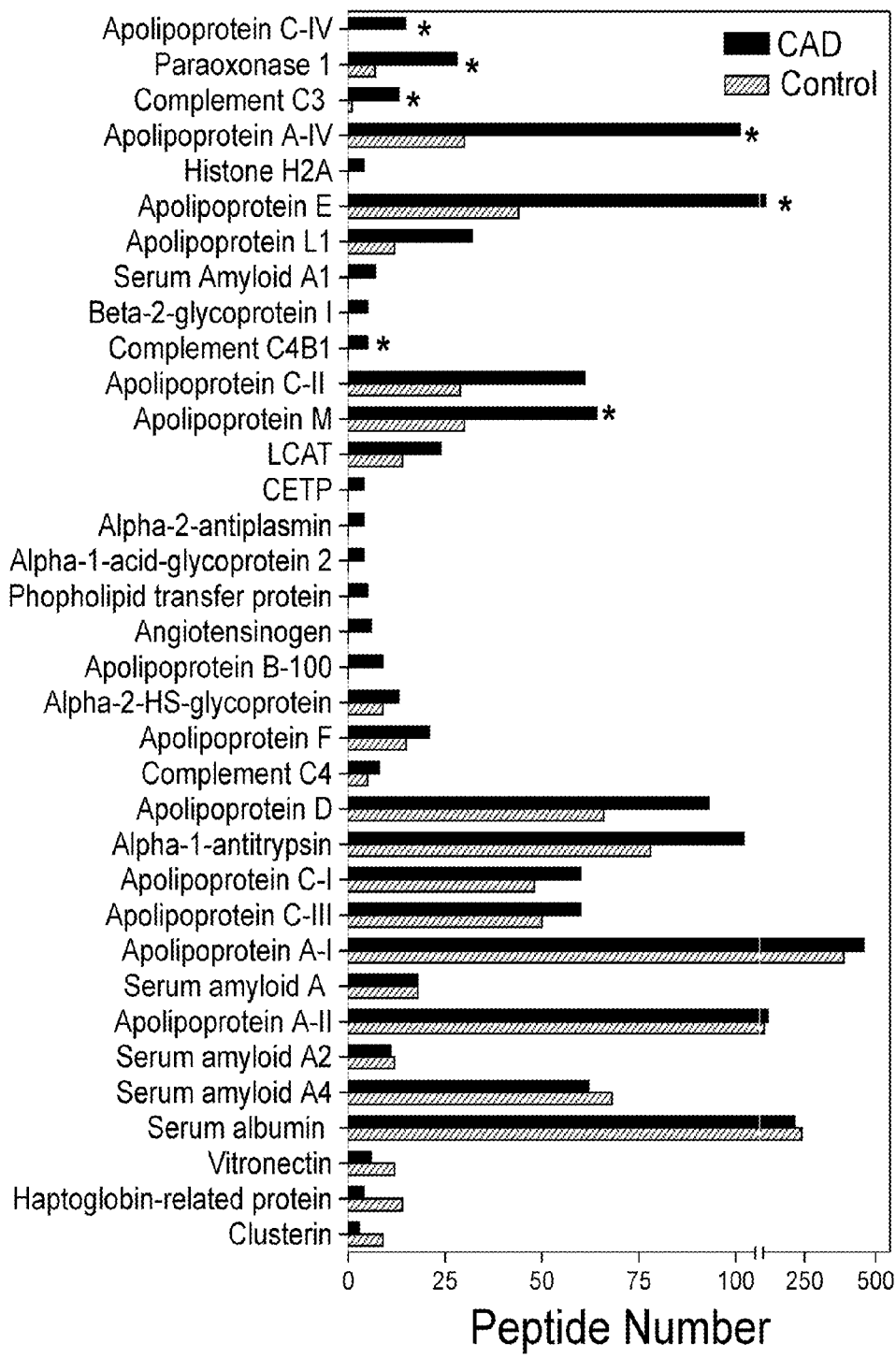
FIG. 2A presents graphical results demonstrating the relative abundance of particular HDL-associated proteins isolated from $HDL_3$ obtained from normal subjects and from subjects with CVD, as described in EXAMPLE 5.
Figure 2B:
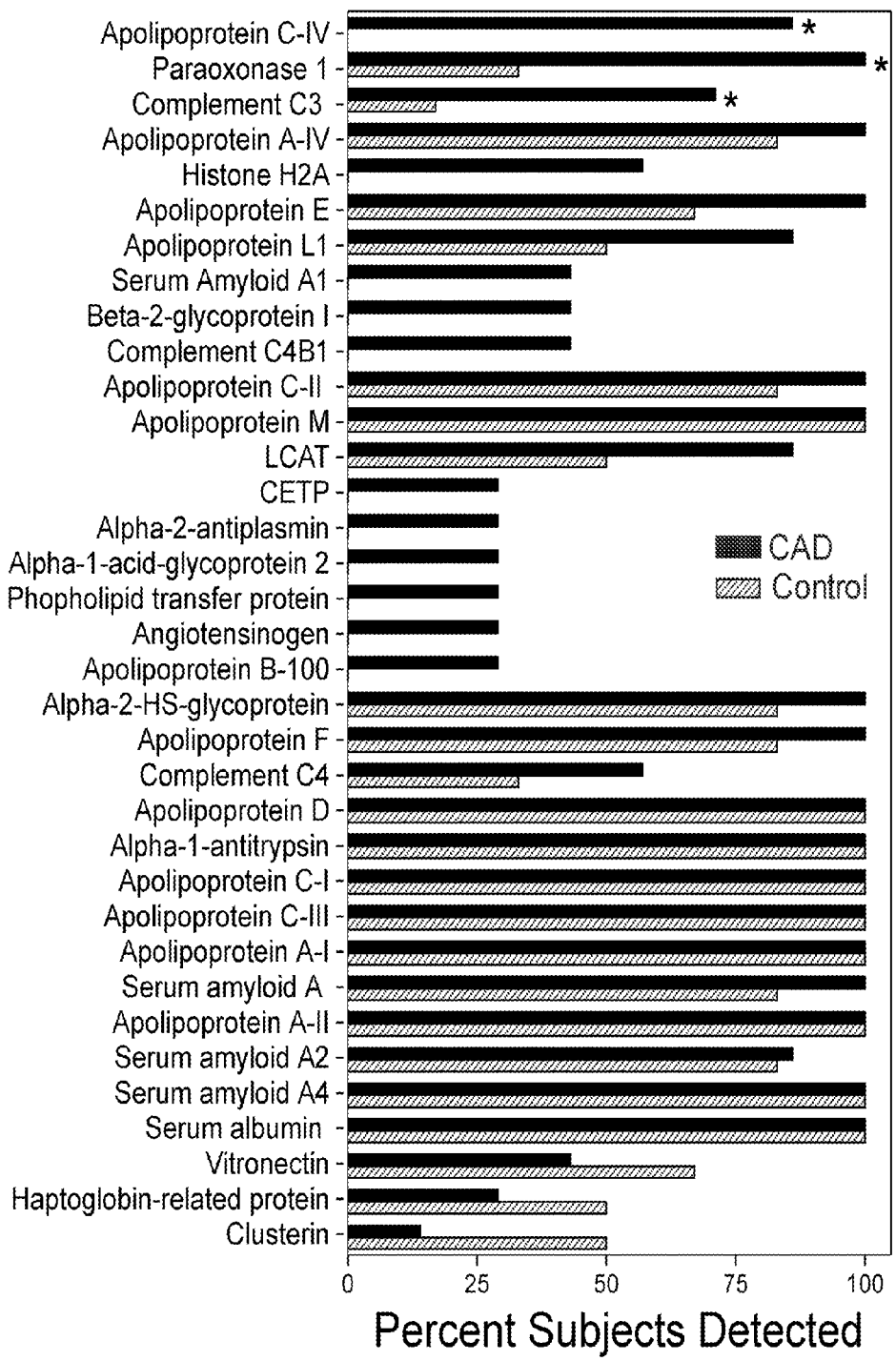
FIG. 2B presents graphical results comparing the percentage of normal subjects and subjects with CVD in which particular HDL-associated proteins were detected using tandem mass spectroscopy, as described in EXAMPLE 5.

TABLE 3 shows the number of peptides detected for each HDL-associated protein (including repeated identifications of the same peptide). The total number of peptides detected for each protein in the 13 independent analysis ranges from 4 (the minimum number required for inclusion in this analysis) to 847 (for ApoA-I). FIG. 2A shows a graphical representation of the number of peptides detected for each protein in normal subjects and CVD subjects. FIG. 2B shows a graphical representation of the number of subjects in each group with detectable peptides for each protein. The columns marked with an asterisk ("*") have a P value <0.05. The P value was assessed by Student's t-test (peptide number) or Fisher's exact test (subject number). The Student's unpaired t-test was used to compare the number of unique peptides identified in CVD patients versus healthy subjects. For proteins in which no peptides were identified in one group, a one-sample t-test was used to compare the number of unique peptides to a theoretical mean of 0. Fisher's exact test was used to compare the number of subjects from which each protein was identified in CVD patients versus healthy subjects. For all statistical analyses, P<0.05 was considered significant.

TABLE 3

PROTEINS DETECTED BY 2-DIMENSIONAL µLC-ESI-MS/MS IN HDL$_3$ ISOLATED FROM PLASMA OF CVD PATIENTS AND/OR CONTROL SUBJECTS (WITH AT LEAST TWO UNIQUE PEPTIDES IDENTIFIED PER PROTEIN)

| Protein ID | Protein Description # | # Peptides in Normal Subjects | # Peptides in CVD subjects | Total # Peptides | Percent of Normal subjects detected | Percent of CVD subjects detected |
| --- | --- | --- | --- | --- | --- | --- |
| IPI00022731 | ApoC-IV | 0 | 15 | 15 | 0 | 85% |
| IPI00218732 | PON-1 | 7 | 28 | 35 | 42% | 100% |
| IPI00164623 | C3 (dg region aa954-1303) | 1 | 13 | 14 | 14.2% | 71.4% |
| IPI00304273 | ApoA-IV | 30 | 101 | 131 | 85.7% | 100% |

TABLE 3-continued

PROTEINS DETECTED BY 2-DIMENSIONAL μLC-ESI-MS/MS IN HDL$_3$ ISOLATED FROM PLASMA OF CVD PATIENTS AND/OR CONTROL SUBJECTS (WITH AT LEAST TWO UNIQUE PEPTIDES IDENTIFIED PER PROTEIN)

| Protein ID | Protein Description # | # Peptides in Normal Subjects | # Peptides in CVD subjects | Total # Peptides | Percent of Normal subjects detected | Percent of CVD subjects detected |
|---|---|---|---|---|---|---|
| IPI00021842 | ApoE | 44 | 114 | 158 | 66.1% | 100% |
| IPI00177869 | ApoL1 | 12 | 32 | 44 | 50.0% | 85.7% |
| IPI00298828 | Beta-2-glycoprotein I | 0 | 5 | 5 | 0 | 42.8% |
| IPI00018524 | Histone H2A | 0 | 4 | 4 | 0 | 57.1% |
| IPI00418163 | Complement C4B1 | 0 | 5 | 5 | 0 | 42.8% |
| IPI00452748 | Serum Amyloid A1 | 0 | 7 | 7 | 0 | 42.8% |
| IPI00021856 | Apo C-II | 29 | 61 | 90 | 85.7% | 100% |
| IPI00030739 | ApoM | 30 | 64 | 94 | 85.7% | 100% |
| IPI00022331 | Lecithin-cholesterol acetyltransferase | 14 | 24 | 38 | 57.1% | 85.7% |
| IPI00006173 | Cholesterol ester transfer protein | 0 | 4 | 4 | 0 | 28.5% |
| IPI00029863 | Alpha-2-antiplasmin | 0 | 4 | 4 | 0 | 28.5% |
| IPI00020091 | alpha-1-acid glycoprotein 2 | 0 | 4 | 4 | 0 | 28.5% |
| IPI00022733 | Phospholipid transfer protein | 0 | 5 | 5 | 0 | 28.5% |
| IPI00032220 | Angiotensinogen | 0 | 6 | 6 | 0 | 28.5% |
| IPI00022229 | Apolipoprotein B-100 | 0 | 9 | 9 | 0 | 28.5% |
| IPI00022431 | Alpha-2-HS-glycoprotein | 9 | 13 | 22 | 85.7% | 100% |
| IPI00299435 | ApoF | 15 | 21 | 36 | 85.7% | 100% |
| IPI00032258 | C4 | 5 | 8 | 13 | 42.8% | 57.1% |
| IPI00006662 | ApoD | 66 | 93 | 159 | 100% | 100% |
| IPI00305457 | Alpha-1-antitrypsin | 78 | 102 | 180 | 100% | 100% |
| IPI00021855 | ApoC-I | 98 | 60 | 108 | 100% | 100% |
| IPI00021857 | ApoC-III | 50 | 60 | 110 | 100% | 100% |
| IPI00021841 | ApoA-I | 388 | 459 | 847 | 100% | 100% |
| IPI00022368 | Serum amyloid A | 18 | 18 | 36 | 85.7% | 100% |
| IPI00021854 | ApoA-II | 108 | 121 | 229 | 100% | 100% |
| IPI00006146 | Serum amyloid A2 | 12 | 11 | 23 | 71.4% | 85.7% |
| IPI00019399 | Serum amyloid A4 | 68 | 62 | 130 | 100% | 100% |
| IPI0002243 | Serum albumin | 241 | 216 | 457 | 100% | 100% |
| IPI00298971 | Vitronectin | 12 | 6 | 18 | 71.4% | 28.5% |
| IPI00296170 | Haptoglobin-related protein | 14 | 4 | 18 | 57.1% | 28.5% |
| IPI00291262 | Clusterin | 9 | 3 | 12 | 57.1% | 14.2% |

Example 4

This example describes the use of a peptide index ("PI") to compare the relative abundance of peptides derived from HDL-associated proteins in normal subjects and in subjects with CVD, in order to determine protein markers that may be used as biomarkers to diagnose and/or assess the risk of CVD in an individual subject.

Rationale: Recent studies strongly support the hypothesis that quantifying the number of peptides, the number of MS/MS spectra, or the percent sequence coverage identified in the LC-MS/MS analysis provides a semiquantitative assessment of relative protein abundance (Washburn, M. P., et al., *Anal. Chem.* 75:5054-5061, 2003). In order to obtain semi-quantitative data, a two-pronged strategy was adopted. First, it was determined whether the number of peptides derived from each protein in healthy controls differed significantly from that found in patients with CVD. Second, an empirical test was developed, referred to as the "peptide index" in order to provide a semiquantitative measure of relative protein abundance in the protein cargo associated with HDL.

Statistical analysis: For each protein identified by MS/MS, the peptide index ("PI") was calculated as:

PI=[(peptides in CVD subjects/total peptides)×(% of CVD subjects with 1 or more peptides)]−[(peptides in control subjects/total peptides)×(% of control subjects with 1 or more peptides)].

The Student's unpaired t-test was used to compare the number of unique peptides identified in CVD patients versus healthy subjects. For proteins in which no peptides were identified in one group, a one-sample t-test was used to compare the number of unique peptides to a theoretical mean of 0. Fisher's exact test was used to compare the number of subjects from which each protein was identified in CVD patients versus healthy subjects. For all statistical analyses, $P<0.05$ was considered significant. In this method, a value of "0" indicates that the numbers of peptides and subjects with detectable peptides are about equal in CVD subjects and healthy controls. A positive peptide index value correlates with enrichment of peptides derived from the protein of interest in HDL$_3$ of CVD patients; whereas, a negative peptide index value correlates with enrichment in HDL$_3$ of healthy control subjects as compared to CVD subjects (e.g., a deficiency of the protein of interest in HDL$_3$ of CVD subjects).

The biomarkers with PI values of greater than 0.30 and −0.30 or less are shown below in TABLE 4.

TABLE 4

HDL-ASSOCIATED PROTEINS ENRICHED IN PATIENTS WITH CVD AS ASSESSED BY THE PEPTIDE INDEX AND P VALUE.

| Protein | Peptide Index | P Value | SEQ ID NO: |
|---|---|---|---|
| ApoC-IV | 0.86 | 0.006 | SEQ ID NO: 1 |
| Paraoxonase 1 (PON-1) | 0.73 | 0.004 | SEQ ID NO: 2 |
| C3 | 0.65 | 0.03 | SEQ ID NO: 3 |
| ApoA-IV | 0.58 | 0.002 | SEQ ID NO: 4 |
| ApoE | 0.54 | 0.0003 | SEQ ID NO: 5 |
| ApoL-I* | 0.49 | 0.09 | SEQ ID NO: 6 |
| C4B1 | 0.43 | 0.01 | SEQ ID NO: 7 |
| Histone H2A* | 0.43 | 0.08 | SEQ ID NO: 8 |
| ApoC-II* | 0.41 | 0.10 | SEQ ID NO: 9 |
| ApoM | 0.36 | 0.04 | SEQ ID NO: 10 |
| C3dg | 0.65 | 0.03 | SEQ ID NO: 11 |
| Vitronectin* | −0.30 | 0.10 | SEQ ID NO: 12 |
| Haptoglobin-related Protein* | −0.33 | 0.08 | SEQ ID NO: 13 |
| Clusterin* | −0.34 | 0.15 | SEQ ID NO: 14 |

The P value was assessed by Student's t-test (peptide number) or Fisher's exact test (subject number).
*P > 0.05.

Table 5 provides a set of representative tryptic peptides for the biomarker proteins ApoC-IV (SEQ ID NOS:16-22), PON-1 (SEQ ID NOS:23-33), C3dg (SEQ ID NOS:34-49), ApoA-IV (SEQ ID NOS:50-67), ApoE (SEQ ID NOS:68-82), ApoL1 (SEQ ID NOS:83-92), C4B1 (SEQ ID NOS:93-113), Histone H2A (SEQ ID NOS:114-117), ApoC-II (SEQ ID NOS:118-121), ApoM (SEQ ID NOS:122-126), Vitronectin (SEQ ID NOS:127-136), Clusterin (SEQ ID NOS:137-147), and Haptoglobin-related protein (SEQ ID NOS:148-159). A set of representative peptides from ApoA-I (SEQ ID NOS:160-170) and from ApoA-II (SEQ ID NO: 171-175) is also included in Table 5, which may be used as a control in a CVD assay in accordance with various embodiments of the present invention.

TABLE 5

REPRESENTATIVE BIOMARKERS FOR CVD

| Protein | Sequence | SEQ ID NO |
|---|---|---|
| ApoC-IV | GFMQTYYDDHLR | 16 |
|  | DGWQWFWSPSTFR | 17 |
|  | THSLCPRLVCGDK | 18 |
|  | ELLETVVNR | 19 |
|  | AWFLESK | 20 |
|  | DLGPLTK | 21 |
|  | DSLLKK | 22 |
| PON-1 | YVYIAELLAHK | 23 |
|  | YVYIAELLAHKIHVYEK | 24 |
|  | VVAEGFDFANGINISPDGK | 25 |
|  | AKLIALTLLGMGLALFR | 26 |
|  | NHQSSYQTRLNALR | 27 |
|  | STVELFKFQEEEK | 28 |
|  | EVQPVELPNCLVK | 29 |
|  | GKLLIGTVFHK | 30 |
|  | HANWTLTPLK | 31 |
|  | ALYCEL | 32 |
|  | SLLHLK | 33 |
| C3dg | ILLQGTPVAQMTEDAVDAER | 34 |
|  | AGDFLEANYMNLQR | 35 |
|  | DFDFVPPVVR | 36 |
|  | QLYNVEATSYALLALLQLK | 37 |
|  | DAPDHQELNLDVSLQLPSR | 38 |
|  | SYTVAIAGYALAQMGRLK | 39 |
|  | DMALTAFVLISLQEAK | 40 |
|  | DICEEQVNSLPGSITK | 41 |
|  | APSTWLTAYVVK | 42 |

TABLE 5-continued

REPRESENTATIVE BIOMARKERS FOR CVD

| Protein | Sequence | SEQ ID NO |
|---|---|---|
|  | QPSSAFAAFVKR | 43 |
|  | GPLLNKFLTTAK | 44 |
|  | GYTQQLAFR | 45 |
|  | QGALELIKK | 46 |
|  | WLNEQR | 47 |
|  | WLILEK | 48 |
|  | WEDPGK | 49 |
| ApoA-IV | SLAELGGHLDQQVEEFRRR | 50 |
|  | ARLLPHANEVSQKIGDNLR | 51 |
|  | QKLGPHAGDVEGHLSFLEK | 52 |
|  | ENADSLQASLRPHADELK | 53 |
|  | ELQQRLEPYADQLR | 54 |
|  | VKTDQTVEELRR | 55 |
|  | TQVNTQAEQLRR | 56 |
|  | AVVLTLALVAVAGAR | 57 |
|  | GRLTPYADEFK | 58 |
|  | AKIDQNVEELK | 59 |
|  | QRLAPLAEDVR | 60 |
|  | ALVQQMEQLR | 61 |
|  | ARISASAEELR | 62 |
|  | VEPYGENFNK | 63 |
|  | VNSFFSTFK | 64 |
|  | QLTPYAQR | 65 |
|  | EAVEHLQK | 66 |
|  | GNTEGLQK | 67 |
| ApoE | VRLASHLRKLRKRLLR | 68 |
|  | DADDLQKRLAVYQAGAR | 69 |
|  | VLWAALLVTFLAGCQAK | 70 |
|  | SELEEQLTPVAEETR | 71 |
|  | WELALGRFWDYLR | 72 |
|  | GEVQAMLGQSTEELR | 73 |
|  | VEQAVETEPEPELR | 74 |
|  | VQAAVGTSAAPVPSDNH | 75 |
|  | SWFEPLVEDMQR | 76 |
|  | AATVGSLAGQPLQER | 77 |
|  | ERLGPLVEQGR | 78 |
|  | QQTEWQSGQR | 79 |
|  | AQAWGERLR | 80 |
|  | ALMDETMK | 81 |
|  | QWAGLVEK | 82 |
| ApoL1 | VSVLCIWMSALFLGVGVR | 83 |
|  | VTEPISAESGEQVER | 84 |
|  | WWTQAQAHDLVIK | 85 |
|  | ANLQSVPHASASRPR | 86 |
|  | SKLEDNIRRLR | 87 |
|  | VNEPSILEMSR | 88 |
|  | SETAEELKK | 89 |
|  | NEADELRK | 90 |
|  | MEGAALLR | 91 |
|  | ALADGVQK | 92 |
| C4B1 | DDPDAPLQPVTPLQLFEGRR | 93 |
|  | ALEILQEEDLIDEDDIPVR | 94 |
|  | AACAQLNDFLQEYGTQGCQV | 95 |
|  | AAFRLFETKITQVLHFTK | 96 |
|  | MRPSTDTITVMVENSHGLR | 97 |
|  | GLESQTKLVNGQSHISLSK | 98 |
|  | AVGSGATFSHYYYMILSR | 99 |
|  | VDVQAGACEGKLELSVDGAK | 100 |
|  | GHLFLQTDQPIYNPGQR | 101 |
|  | SRLLATLCSAEVCQCAEGK | 102 |
|  | GLEEELQFSLGSKINVK | 103 |
|  | EPPLSCCQFAESLRKK | 104 |
|  | GCGEQTMIYLAPTLAASR | 105 |
|  | AINEKLGQYASPTAKR | 106 |
|  | TTNIQGINLLFSSRR | 107 |
|  | HLVPGAPFLLQALVR | 108 |
|  | EELVYELNPLDHR | 109 |
|  | NTTCQDLQIEVTVK | 110 |
|  | GPEVQLVAHSPWLK | 111 |
|  | CCQDGVTRLPMMR | 112 |
|  | AEMADQAAAWLTR | 113 |

TABLE 5-continued

REPRESENTATIVE BIOMARKERS FOR CVD

| Protein | Sequence | SEQ ID NO |
|---|---|---|
| Histone H2A | VTIAQGGVLPNIQAVLLPKK | 114 |
| | NDEELNKLLGK | 115 |
| | AGLQFPVGR | 116 |
| | VHRLLRK | 117 |
| ApoC-II | STAAMSTYTGIFTDQVLSVLK | 118 |
| | TYLPAVDEKLR | 119 |
| | ESLSSYWESAK | 120 |
| | TAAQNLYEK | 121 |
| ApoM | WIYHLTEGSTDLR | 122 |
| | NQEACELSNN | 123 |
| | SLTSCLDSK | 124 |
| | TEGRPDMK | 125 |
| | DGLCVPRK | 126 |
| Vitronectin | GDVFTMPEDEYTVYDDGEEK | 127 |
| | GSQYWRFEDGVLDPDYPR | 128 |
| | DSWEDIFELLFWGR | 129 |
| | SIAQYWLGCPAPGHL | 130 |
| | AVRPGYPKLIR | 131 |
| | GQYCYELDEK | 132 |
| | VDTVDPPYPR | 133 |
| | CTEGFNVDKK | 134 |
| | NQNSRRPSR | 135 |
| | NGSLFAFR | 136 |
| Clusterin | EILSVDCSTNNPSQAKLRR | 137 |
| | ASSIIDELFQDRFFTR | 138 |
| | QQTHMLDVMQDHFSR | 139 |
| | ELDESLQVAERLTRK | 140 |
| | TLLSNLEEAKKKK | 141 |
| | NPKFMETVAEK | 142 |
| | QTCMKFYAR | 143 |
| | EIQNAVNGVK | 144 |
| | ALQEYRKK | 145 |
| | EDALNETR | 146 |
| | HNSTGCLR | 147 |
| Haptoglobin-related protein | VGYVSGWGQSDNFKLTDHLK | 148 |
| | SPVGVQPILNEHTFCVGMSK | 149 |
| | VVLHPNYHQVDIGLIKLK | 150 |
| | NPANPVQRILGGHLDAK | 151 |
| | AVGDKLPECEAVCGKPK | 152 |
| | MSDLGAVISLLLWGR | 153 |
| | NLFLNHSENATAK | 154 |
| | TEGDGVYTLNDKK | 155 |
| | DIAPTLTLYVGKK | 156 |
| | SCAVAEYGVYVK | 157 |
| | VTSIQDWVQK | 158 |
| | VMPICLPSK | 159 |
| ApoA-I (control protein) | Full length protein: | 160 |
| | DYVSQFEGSALGK | 161 |
| | QKLHELQEKLSPLGEEMR | 162 |
| | VSFLSALEEYTKKLNTQ | 163 |
| | HFWQQDEPPQSPWDR | 164 |
| | EQLGPVTQEFWDNLEK | 165 |
| | AAVLTLAVLFLTGS QAR | 166 |
| | ENGGARLAEYHAK | 167 |
| | VQPYLDDFQKK | 168 |
| | THLAPYSDELR | 169 |
| | WQEEMELYR | 170 |
| ApoA-II (control protein) | full length protein | 171 |
| | AGTELVNFLSYFVELGTQPATQ | 172 |
| | EPCVESLVSQYFQTVTDYGK | 173 |
| | EQLTPLIKK | 174 |
| | SPELQAEAK | 175 |

The peptides shown in Table 5 are representative peptides ranging in size from about 20 amino acids to about 6 amino acids, resulting from a digest of each biomarker protein with trypsin, which cleaves adjacent to lysine (K) or arginine (R) residues in proteins. The peptides shown in Table 5 may be used to positively identify the presence of one or more CVD biomarkers in an assay, such as a mass spectrometry assay. The protein abundance may be determined in comparison to a control peptide that is expected to be present in equal amounts in serum or an HDL subfraction thereof, in control subjects and CVD patients, such as proteins with a PI index from about 0.20 to about −0.20, including ApoA-I and ApoA-II. A representative set of peptides for ApoA-I (SEQ ID NO: 160-170) and peptides for ApoA-II (SEQ ID NO: 171-175) is provided above in Table 5.

The peptides shown above in Table 5 may be used as antigens to raise antibodies specific for each biomarker using methods well known to one of skill in the art. The biomarker-specific antibodies may be used in the methods, assays, and kits described herein.

Results: The statistical analysis of peptide abundance, as described above, identified ten proteins that are significantly enriched in the CVD patient population in comparison to normal subjects, and are useful as CVD biomarkers as shown above in TABLE 4, TABLE 5, and FIG. 3. The CVD biomarkers include ApoC-IV, PON-1, C3, C4, ApoA-IV, ApoE, ApoL1, C4B1, histone H2A, ApoC-II, and ApoM. These ten biomarkers have a peptide index of equal to or above 0.30, which is one useful criteria by which to classify biomarkers enriched in CVD subjects in comparison to control subjects. The HDL-associated CVD biomarkers with corresponding peptide index and P values are shown above in TABLE 4. Each of the ten biomarkers is described in more detail below.

Figure 3:
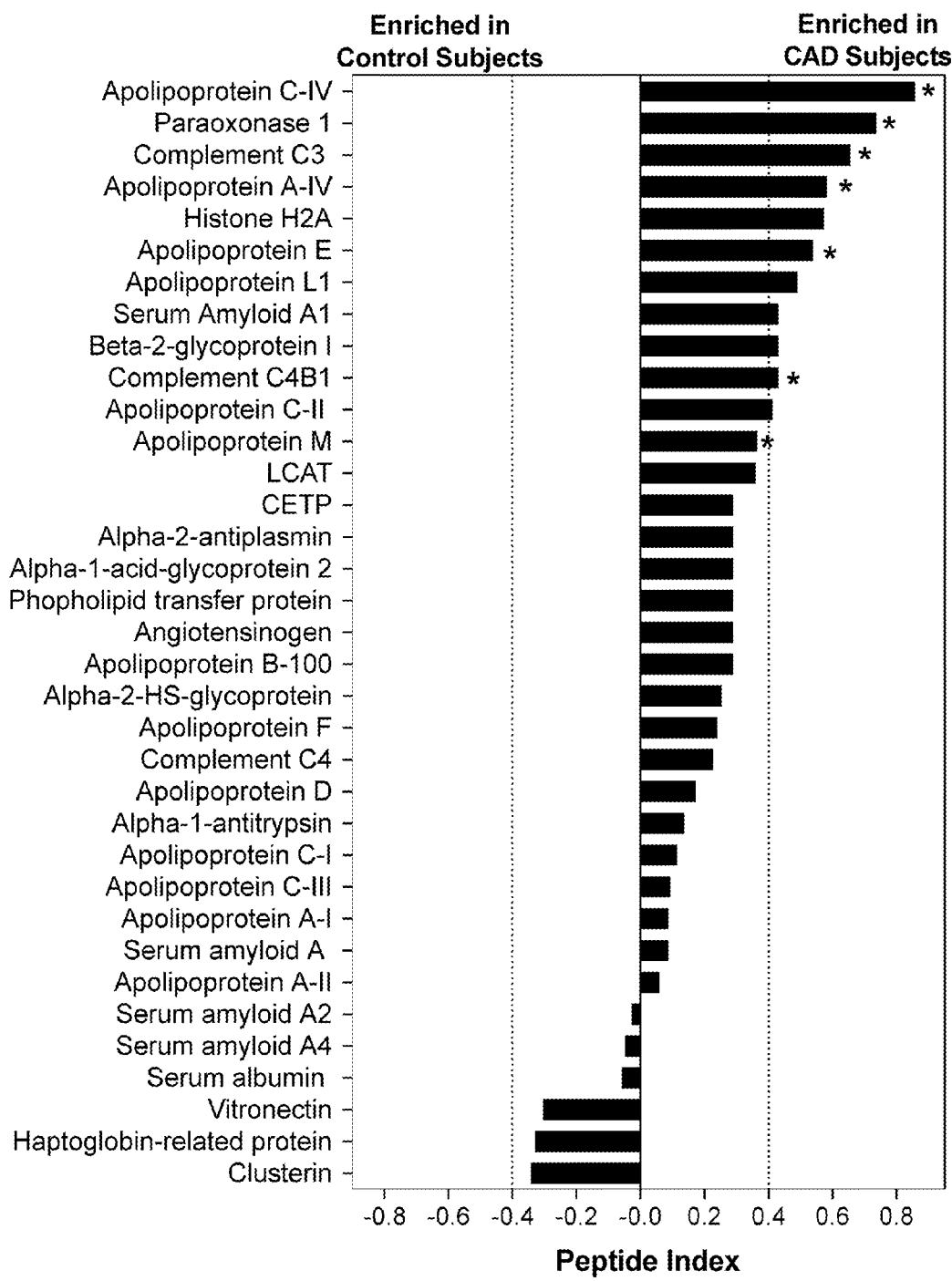
FIG. 3 presents graphical results demonstrating the relative abundance, as assessed by a peptide index, of particular HDL-associated proteins isolated from $HDL_3$ obtained from normal subjects and from subjects with CVD, as described in EXAMPLE 5.

ApoC-IV was unexpectedly found to be highly enriched in the $HDL_3$ of CVD subjects as compared to normal subjects, with a peptide index of 0.86 and a P value of 0.006 as shown in FIG. 3 and TABLE 4. ApoC-IV was recently identified in plasma of normal human subjects at low levels; however, no correlation was previously made with CVD (Kotite et al., *J. Lipid Res.* 44:1387-1394, 2003). ApoC-IV is known to be part of the ApoE/C-I/C-IV/C-II gene cluster. While not wishing to be bound by theory, it has been proposed that activation of the ApoE/C-I/C-IV/C-II gene cluster functions as a mechanism for removing lipids from macrophage foam cells (Mak, P. A. et al., *J. Biol. Chem.* 277:31900-31908, 2002).

ApoE and ApoC-II were also among the enriched proteins found in $HDL_3$ of CVD patients, as shown in TABLE 4 and FIG. 3. It has previously been shown that macrophage-specific expression of ApoE protects hyperlipidemic mice from atherosclerosis, suggesting that ApoE prevents foam cell formation in the artery wall (Linton, M. F., et al., *Science* 267: 1034-1037, 1995). ApoC-II and ApoL1 have previously been identified in HDL of healthy subjects (Karlsson et al., *Proteomics* 5:1431-1445, 2005); however, no correlation has previously been made between enriched levels of ApoC-II or ApoL1 in the HDL of CVD subjects.

With respect to the identification of ApoM as a biomarker for CVD, it has been previously shown that ApoM is needed for the formation of pre-β HDL in mice, and that atherosclerosis is exacerbated in animals deficient in the protein (Wolfrum, C., et al., *Nat. Med.* 11:418-422, 2005). However, enriched levels of ApoM in HDL has not been previously correlated with CVD.

Biomarkers associated with inflammation were found to be enriched in CVD subjects, including C3, C3dg, C4B1 and PON-1, as shown in FIGS. 3 and 6. C3 is known to be a key effector of the complement pathway, and may also be secreted by macrophages (Oksjoki, R., et al., *Curr. Opin. Lipidol.* 14:477-482, 2003). C3 activation results in its deposition on activating particles and/or downstream activation of the membrane attack complex. The C3dg proteolytic fragment of C3 contains a reactive thioester bond that can cross-link to host or microbial proteins and target them for elimination by phagocytes (Frank, M. M., *Nat. Med.* 7:1285-1286, 2001). Therefore, it is noteworthy that all the peptides identified by MS in $HDL_3$ of CVD subjects were located in the C3dg region (SEQ ID NO: 11) of the C3 protein (SEQ ID NO: 3), as shown in TABLE 3 (e.g., SEQ ID NOS:34-49 shown in TABLE 5). For example, three representative peptides unique to C3dg ("ILLQGTPVAQMTEDAVDAER" SEQ ID NO: 34), ("AGDFLEANYMNLQR" SEQ ID NO: 35), and ("DFDFVPPVVR" SEQ ID NO:36), were identified by MS/MS spectrometry in $HDL_3$ isolated from the plasma of CVD subjects (see EXAMPLE 7). Moreover, both a polyclonal anti-C3 antibody and a monoclonal antibody specific for C3dg reacted with proteins that were carried in $HDL_3$, demonstrating that C3dg is present in a complex with $HDL_3$ proteins as further described in EXAMPLE 7.

An elevated level of PON-1 was unexpectedly found in the $HDL_3$ of CVD patients, as shown by mass spectroscopy (see FIGS. 2A-2B and FIG. 3), and Western blotting (see FIG. 4). The role of PON-1 in pathogenesis of human atherosclerotic events is currently unclear (see Chait, A., et al., *J. Lipid Res.* 46:389-403, 2005). PON-1 is synthesized primarily in the liver and transported by HDL in plasma. In humans, it is known that the highest level of PON activity is found in the $HDL_3$ fraction (Bergmeier, C., *Clin. Chem.* 50:2309-2315, 2004). It has been proposed that PON-1 acts as an antioxidant and might protect against atherosclerosis (Machness, M., et al., *Curr. Opin. Lipidol.* 15:399-404, 2004; Shih, D. M., et al., *Nature* 394:284-287, 1998; Shih, D. M., et al., *J. Biol. Chem.* 275:17527-17535, 2000). However, the ability of PON-1 to degrade oxidized lipids and act as an antioxidant has recently been questioned (Marathe, G. K., et al., *J. Biol. Chem.* 278: 3937-3947, 2003). PON-1 activity decreases during the acute-phase response in humans and animals, and human PON-1 gene polymorphisms have been associated with cardiovascular disease (Heinecke, J. W., et al., *Am. J. Hum. Genet.* 62:20-24, 1998). However, it has been accepted in the art that enzyme activity rather than genotype or protein level correlates best with the risk of atherosclerotic events (Jarvik, G. P., et al., *Arterioscler. Thromb. Vasc. Biol.* 23:1465-1471, 2003). Importantly, previous studies in mouse models of hyperlipidemia have correlated decreased activity of PON-1 with susceptibility to atherosclerosis (Bergmeier, C., et al., supra). Therefore, the accepted view of decreased activity and/or protein level of PON-1 correlation with CVD contrasts with the results provided in the present invention which demonstrate increased PON-1 protein in the $HDL_3$ of CVD patients (PI=0.73, P=0.004), as shown in TABLE 4.

The $HDL_3$ derived from CVD subjects was unexpectedly found to be enriched in C4B1, a haplotype of C4 that has been implicated in the pathogenesis of autoimmune disease (Yu, C. Y., et al., *Trends Immunol.* 25:694-699, 2004). While not wishing to be bound by theory, it is possible that the C4B1 is derived from macrophages, because it is known that C4 is synthesized in macrophages derived from mice and human monocytes. See Sackstein, R., et al., *J. Immunol.* 133:1618-1626, 1984; McPhaden, A. R., et al., *Immunol. Res.* 12:213-232, 1993.

Histone H2A was found to be present at enriched levels in CVD patients (PI=0.43, P=0.08), see TABLE 4. It was surprising to find histone H2A associated with HDL, because it is a component of the nucleosome, and as such is an intracellular protein. Prior studies have located histones on the surfaces of various cells, including activated neutrophils, monocytes and lymphocytes (Brinkmann, V., et al., *Science* 303:1532-1535, 2004; Emlen, W., et al., *J. Immunol.* 148: 3042-3048, 1992). It is noteworthy that histone H2A incorporated into extracellular "nets" produced by activated neutrophils has been shown to have antimicrobial properties (Brinkmann, V., et al., *Science* 303:1532-1535, 2004).

ApoA-IV was also identified as a biomarker for CVD, with a PI=0.58, P=0.002. It is known that ApoA-IV protein becomes more abundant in HDL during acute inflammation (Chait, A., et al., *J. Lipid Res.* 46:389-403, 2005; Khovidhunkit, W., et al., *Atherosclerosis* 176:37-44, 2004). One study has reported increased plasma levels of ApoA-IV in NIDDM patients with macrovascular disease (Verges et al., *Diabetes* 46:125-132, 1997).

As shown in FIG. 3, seven proteins were identified that tended to be more abundant in $HDL_3$ of CVD patients than in $HDL_3$ of normal control subjects, with peptide indices ranging from 0.20 to 0.40, including LCAT, CETP, alpha-2-antiplasmin, alpha-1-acid-glycoprotein 2, phospholipid transfer protein, angiotensinogen, and apolipoprotein B-100, all with P values greater than 0.05. Several of these proteins, including phospholipid transfer protein and cholesterol ester transfer protein (CETP) are known to associate with HDL and/or play a role in HDL metabolism. Apolipoprotein B-100 is a major component of LDL, and is known to be present in humans with clinically significant atherosclerosis. Angiotensin has not been previously detected in circulating HDL, but increased levels of this protein have been found in hypercholesterolemic mice (Daugherty, A., et al., *Circulation* 110: 3849-3857, 2004).

With continued reference to FIG. 3, thirteen proteins were found to be equally abundant in $HDL_3$ derived from CVD patients and normal control subjects, with peptide indices ranging from −0.20 to 0.20. This group includes six apolipoproteins. As expected, ApoA-I (PI=0.08) and ApoA-II (PI=0.06) were found to be present at similar levels in CVD and control subjects, with peptide indexes close to 0. Also included in this group are ApoF, ApoD, ApoC-I, and ApoC-III. This group also includes inflammatory proteins SAA2, SAA4, and complement C4. Of these, only C4 was not previously known to be associated with HDL. In addition, three plasma proteins were identified (albumin, alpha-2-HS-glycoprotein, and alpha-1-antitrypsin) that may also be associated with HDL, possibly due to hydrophobic interactions (see Hamilton, J. A., *Prog. Lipid Res.* 43:177-199, 2004).

Three proteins were identified that tended to be more enriched in $HDL_3$ of apparently healthy controls as compared to CVD subjects, with peptide indexes equal to or below −0.30, including vitronectin (PI=−0.40, P=0.10), haptoglobin-related protein (PI=−0.33; P=0.08), and clusterin (PI=−0.34; P=0.15). Both vitronectin and clusterin have been proposed to regulate complement activity (Oksjoki, R., et al., *Curr. Opin. Lipidol.* 14:477-482, 2003). Vitronectin and clusterin, as well as other proteins that regulate C3b, have been shown to be expressed in human atherosclerotic lesions (Seifert, P. S., et al., *Arteriosclerosis* 9:802-811, 1989; Yasojima, K., et al., *Arterioscler. Thromb. Vasc. Biol.* 21:1214-1219, 2001). It is known that both classic and alternative complement cascades are activated in human atherosclerotic lesions (Oksjoki, R., et al., *Curr. Opin. Lipidol.* 14:477-482, 2003; Yasojima, K., et al., *Am. J. Pathol.* 158:1039-1051, 2001). Complement C3b, but not C5b-9, is deposited in vulnerable and ruptured plaques, suggesting that complement might be involved in the acute coronary syndrome (Laine, P., et al., *Am. J. Cardiol.* 90:404-408, 2002). Proteins implicated in atherogenesis, including immunoglobulins, C-reactive protein, and unesterified cholesterol can activate the complement cascade, leading to the production of C3b (Yla-Herttuala, S., et al.,

*Arterioscler. Thromb.* 14:32-40, 1994). Both vitronectin and clusterin have been proposed to regulate complement activity (Oksjoki, R., et al., 2003, supra). Therefore, the presence of increased amounts of vitronectin and clusterin in normal subjects suggests that inhibition of the complement pathway may be atheroprotective. While not wishing to be bound by theory, these results suggest that the presence of these proteins in blood may be protective and beneficial to prevent CVD, and/or a deficiency in these proteins may be a risk factor or indicate a predisposition to CVD.

Conclusion: The present study identified a total of 35 HDL-associated proteins in $HDL_3$ samples obtained from normal and/or CVD subjects. The majority of the identified proteins were known to reside in HDL, which validates the method used to identify and quantitate HDL-associated proteins. Using the validated method, the results presented above demonstrate that 10 proteins are selectively enriched in $HDL_3$ from CVD subjects, as shown in TABLE 4. The peptide index is a useful measure of the relative abundance of HDL-associated proteins present in normal subjects and CVD subjects. As shown in FIG. 3 and TABLE 4, using the peptide index, ten proteins were identified that are highly enriched in CVD subjects (PI greater than or equal to 0.30); seven proteins were identified that are somewhat more abundant in the CVD subjects than normal controls (PI greater than 0.02); thirteen proteins were found to be equally abundant in the two populations (PI between 0.20 and –0.20); and three proteins were found to be enriched in $HDL_3$ of normal controls as compared to CVD subjects (PI equal to or below –0.30). These results demonstrate that the $HDL_3$ subfraction carries several previously unsuspected HDL-associated proteins that are enriched in CVD patients and serve as novel biomarkers for the presence and/or risk of CVD. Therefore, the identification of elevated levels of the biomarkers shown in TABLE 4, including ApoC-IV, PON-1, C3, C4, C3dg, ApoA-IV, ApoE, ApoL1, C4B1, histone H2A, ApoC-II, and ApoM in HDL, either individually, or in combination, may be used for the diagnosis and/or risk assessment of CVD in a subject.

Example 5

This example uses Western blotting techniques to quantify the relative levels of PON-1 in $HDL_3$ isolated from CVD patients and healthy control subjects.

Methods: $HDL_3$ was isolated from the blood plasma of four subjects with established CVD and healthy control subjects as described above in EXAMPLE 1. The $HDL_3$ proteins were separated by SDS-PAGE, transferred to a nitrocellulose membrane, and probed with a polyclonal antibody to PON-1 (provided by C. Furlong, University of Washington).

HDL was also isolated from human atherosclerotic tissue that was obtained at surgery from CVD subjects undergoing carotid endarterectomy, as described below in EXAMPLE 8.

Results: FIG. 4 shows the results of a Western blot probed with the PON-1 antibody. Lanes 1-4 contain $HDL_3$ samples obtained from the CVD subjects, lanes 5-7 contain $HDL_3$ samples obtained from the healthy control subjects, and lanes 8-9 contain HDL derived from atherosclerotic lesions (each lane of lesion HDL represents material isolated from two different lesions). As shown in FIG. 4, PON-1 protein is clearly associated with HDL and is present in $HDL_3$ of CVD patients. For example, a representative peptide unique to PON-1 ("YVYIAELLAHK" SEQ ID NO:23) was identified by MS/MS spectrometry in $HDL_3$ isolated from the plasma of CVD subjects. In contrast, PON-1 protein is not detectable in the $HDL_3$ of control subjects (see FIG. 4, lanes 5-7). These results are consistent with the µLC-ESI-MS/MS analysis described in EXAMPLES 3-4, where PON-1 was calculated to have a peptide index of 0.73 (P value 0.004), as shown in FIG. 3 and TABLE 4.

Example 6

This example describes the use of reconstructed ion chromatograms to quantify the relative abundance of peptides unique to biomarkers that were identified as being enriched in $HDL_3$ samples isolated from CVD patients as compared to healthy control subjects.

Methods: The ion current and the charge state were extracted from a full scan mass spectrum for a given peptide, and this information was used to construct a chromatogram. The relative abundance of a given peptide was compared in tryptic digests of $HDL_3$ isolated from CVD subjects and control subjects that were subjected to µLC-ESI-MS/MS analysis as described in EXAMPLE 1.

Figure 5A:
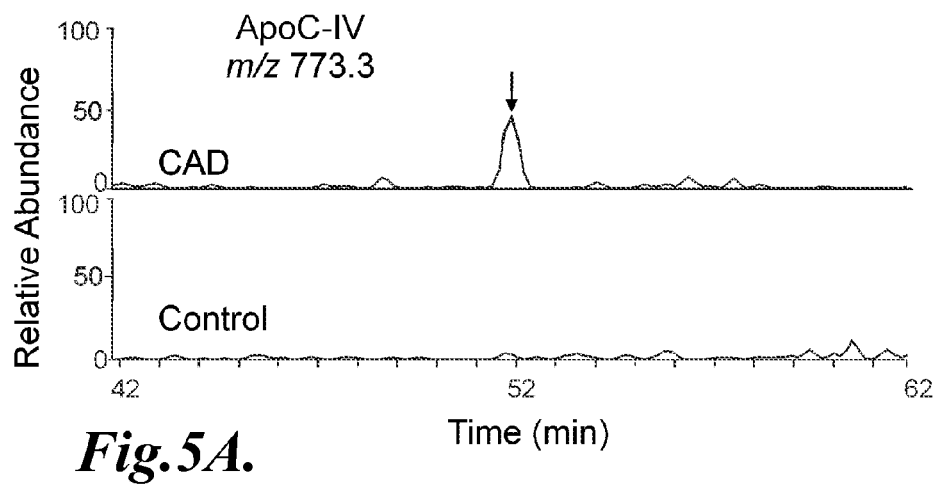
FIG. 5A presents graphical results obtained from tandem mass spectrometry, demonstrating that ApoC-IV is present at a high concentration in $HDL_3$ isolated from subjects with CVD, but is not detected in $HDL_3$ isolated from control subjects, as described in EXAMPLE 7.

Results: FIG. 5A is a reconstructed chromatogram extracted from a full scan mass spectrum that graphically illustrates that the peptide GFMQTYYDDHLR (SEQ ID NO:16) with a charge state of 2+ and an ion current of 773.3 m/z was derived from a tryptic digest of ApoC-IV associated with $HDL_3$ isolated from a CVD subject, using tandem mass spectroscope methods, in agreement with the results shown in FIG. 3.

Figure 5B:
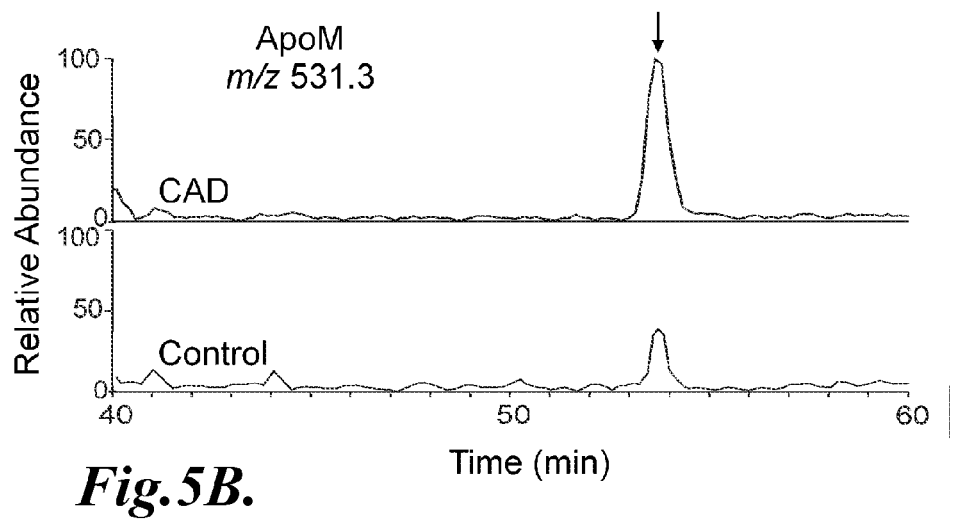
FIG. 5B presents graphical results obtained from tandem mass spectrometry, demonstrating that ApoM is present at a higher concentration in $HDL_3$ isolated from subjects with CVD as compared to the level observed in $HDL_3$ isolated from control subjects, as described in EXAMPLE 7.

FIG. 5B is a reconstructed chromatogram extracted from a full scan mass spectrum that graphically illustrates that the peptide WIYHLTEGSTDLR (SEQ ID NO:122) derived from a tryptic digest of ApoM with a charge state of 3+ and an ion current of 531.1 m/z is present in increased concentration in $HDL_3$ isolated from CVD subjects as compared to $HDL_3$ isolated from healthy control subjects, in agreement with the results shown in FIG. 3.

Figure 5C:
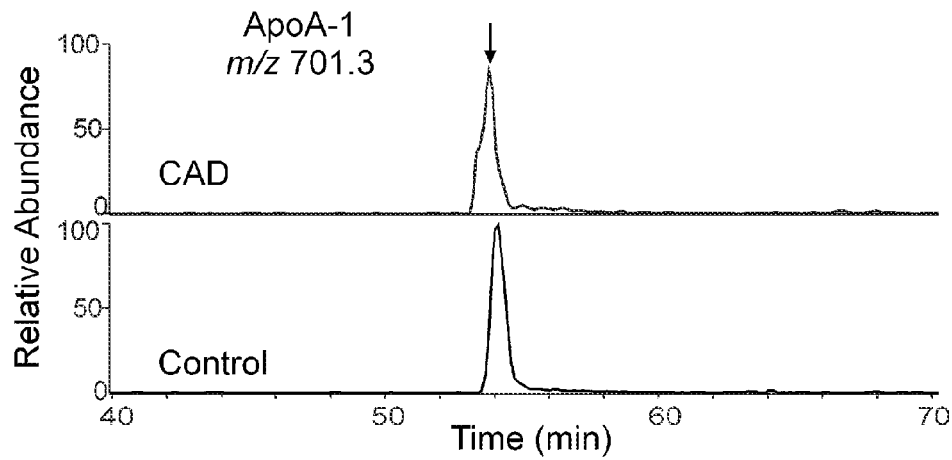
FIG. 5C presents graphical results obtained from mass spectrometry, demonstrating that Apolipoprotein A-I ("ApoA-I") is present at approximately equal concentrations in $HDL_3$ isolated from subjects with CVD and in $HDL_3$ isolated from control subjects, as described in EXAMPLE 7.

FIG. 5C is a reconstructed chromatogram extracted from a full scan mass spectrum that graphically illustrates that the peptide DYVSQFEGSALGK (SEQ ID NO:160) derived from a tryptic digest of ApoA-I with a charge state of 2+ and an ion current of 701.3 m/z is present in approximately equal abundance in $HDL_3$ isolated from CVD subjects as compared to $HDL_3$ isolated from healthy control subjects, in agreement with the results shown in FIG. 3.

Example 7

This example describes the unexpected identification of peptides derived from complement factors C3 and C4B1 in the $HDL_3$ of CVD patients.

Rationale: In view of the unexpected detection of peptides derived from C3 and C4B1 in the $HDL_3$ of CVD patients as described in EXAMPLE 4, the association between C3 and $HDL_3$ was further investigated to determine if C3 forms a complex with HDL. C3 is a major effector of the complement system, and has been implicated in atherogenesis (Oksjoki, R., et al., *Curr. Opin. Lipidol.* 14:477-482, 2003). Activation of C3 leads to the generation of nascent C3b, which may bind covalently to proteins or carbohydrates through its internal thioester bond. In blood, C3b is proteolytically cleaved by factor I and co-factor H to generate iC3b, which, in turn, is further cleaved into C3dg (see Frank, M. M., *Nat. Med.* 7:1285-1286, 2001).

Methods: $HDL_3$ was isolated from CVD patients or healthy controls as described above in EXAMPLE 1. The protein components of the isolated $HDL_3$ were run on SDS-PAGE under reducing and denaturing conditions. The separated proteins were then probed with a polyclonal antibody to human C3 (Quidel), or a monoclonal antibody to C3dg (Lachmann, P., *J. Immunology* 41:503-515, 1980).

Results: The results of the Western blot analysis probed with polyclonal C3 antibody showed that C3 was present at detectable levels in HDL isolated from subjects with CVD as compared to HDL isolated from control subjects (data not shown). These observations suggest that C3, and/or C3 modified by proteolysis could serve as a biomarker for CVD, and, further, that C3 may originate, in part, from atherosclerotic tissue.

Significantly, all three unique peptides identified by MS/MS in $HDL_3$ from CVD patients were derived from within the C3dg region (SEQ ID NO:11), which includes aa 954-1303 of C3 (SEQ ID NO:3).

The three unique C3dg peptides identified were:

| | |
|---|---|
| ILLQGTPVAQMTEDAVDAER | (SEQ ID NO: 34) |
| AGDFLEANYMNLQR | (SEQ ID NO: 35) |
| DFDFVPPVVR | (SEQ ID NO: 36) |

The above-identified peptides all fall within the C3dg region of C3 that contains the thioester bond that reacts with target molecules. Therefore, C3-derived peptides, and more particularly, C3dg-derived peptides, are present in the $HDL_3$ of CVD patients and are useful as biomarkers for CVD.

Example 8

This example describes the identification of HDL-associated proteins in lesions isolated from atherosclerotic plaques in CVD subjects.

Rationale: Lesion HDL was isolated from CVD subjects and analyzed to determine whether proteins found uniquely associated with and/or enriched in the HDL of CVD patients in comparison to control subjects were also present in the lesion HDL, indicating that they were derived from the artery wall.

Methods: Lesion HDL was isolated from atherosclerotic tissue that was harvested from 6 patients during carotid endarterectomy surgery, snap-frozen, and stored at −80° C. until analysis. Lesions from a single subject (~0.5 g wet weight) were mixed with dry ice and pulverized with a pestle in a stainless steel mortar. HDL was extracted from tissue powder as described in Bergt, C., et al., *PNAS* 101:13032-13037, 2004. Briefly, the powdered tissue was re-suspended at 4° C. in 2 ml of antioxidant buffer (138 mM NaCl, 2.7 mM KCl, 10 mM sodium phosphate (pH 7.4)), a protease inhibitor cocktail (Roche Diagnostics, Mannheim, Germany), 100 μm diethylenetriaminepentaacetic acid (DTPA), and 100 μm butylated hydroxyl toluene (PHT) and rocked gently overnight. Tissue was removed by centrifugation, the supernatant was collected, and the pellet was extracted a second time with anti-oxidant buffer for 1 hour. The pooled supernatants were centrifuged at 100,000×g for 30 minutes, and the pellet and uppermost lipemic layer were discarded.

Because arterial tissue contains relatively low levels of ApoA-I, total HDL was isolated and analyzed as "lesion HDL." The lesion HDL was analyzed by immunoblotting with a rabbit polyclonal antibody monospecific for human ApoA-I (Calbiochem) in order to measure the recovery of protein originally present in the lesions. Quantification of ApoA-I by Western blot showed that this procedure recovered ~80% of immunoreactive protein that was originally present in the lesions (data not shown).

HDL proteins isolated from three different pooled preparations of lesion HDL (prepared from two different individual subjects) were combined, digested with trypsin, and subjected to μLC-ESI-MS/MS analysis as described in EXAMPLE 1. Proteins were identified as described in EXAMPLE 3.

Results: Using the peptide search strategy and the two-unique peptide criteria described in EXAMPLE 3, over 100 proteins were identified in the lesion HDL samples from three independent analyses. Importantly, 5 of the 10 proteins that were found to be enriched in the $HDL_3$ samples from CVD patients were also found to be present in lesion HDL samples, as shown below in TABLE 6.

TABLE 6

PROTEINS DETECTED BY 2-DIMENSIONAL μLC-ESI-MS/MS IN HDL ISOLATED FROM HUMAN ATHEROSCLEROTIC TISSUE AND PLASMA OF CVD PATIENTS.

| Protein Description | Total Number of Peptides identified in Lesion HDL | Total Number of Peptides identified in CVD $HDL_3$ | Total Number of Peptides identified in $HDL_3$ from normal controls |
|---|---|---|---|
| Paraoxonase 1 (PON-1) | 26 | 28 | 7 |
| C3 | 45 | 13 | 1 |
| ApoE | 118 | 114 | 37 |
| ApoM | 26 | 64 | 25 |
| C4B1 | 28 | 5 | 0 |

It is noteworthy that three times as many peptides derived from C3 were identified in lesion HDL than in the circulating $HDL_3$ of patients with CVD. The tryptic digest from lesion HDL contained peptides derived from both the α and β chains of C3, consistent with the apparent MW of the bands that reacted with the antibody against C3 in lesion HDL (data not shown).

While the preferred embodiment of the invention has been illustrated and described, it will be appreciated that various changes can be made therein without departing from the scope of the invention.

The embodiments of the invention in which an exclusive property or privilege is claimed are defined as follows:

1. A method of screening a mammalian subject to determine if the subject is at risk to develop, or is suffering from, cardiovascular disease, the method comprising:
   (a) detecting an amount of a biomarker present in a high density lipoprotein (HDL) subfraction, a complex containing Apolipoprotein A-I (ApoA-I), or a complex containing Apolipoprotein A-II (ApoA-II) isolated from a biological sample obtained from the subject, wherein the biomarker is Apolipoprotein C-IV (ApoC-IV) set forth as SEQ ID NO:1 or a portion and/or derivative thereof, wherein the derivative thereof consists of naturally occurring protein having at least 95% homology with SEQ ID NO:1, and wherein the portion thereof comprises a peptide fragment consisting of at least 6 continuous amino acids to 20 continuous amino acids from SEQ ID NO:1, and
   (b) comparing the detected amount of the biomarker in the biological sample to a reference amount of the biomarker determined from a control population of healthy subjects, wherein a difference in the amount of the biomarker between the biological sample and the reference amount is indicative of the presence or risk of cardiovascular disease in the subject.

2. The method of claim 1, wherein the biomarker is present in at least one of a high density lipoprotein subfraction in the density range of about 1.06 to about 1.110 g/mL or a high density lipoprotein subfraction in the density range of about 1.110 to about 1.210 g/mL of the biological sample.

3. The method of claim 1, wherein the biological sample is selected from the group consisting of a blood sample, a serum sample, a plasma sample, a tissue sample, bodily fluid sample and urine sample.

4. The method of claim 1, wherein the biomarker is ApoC-IV set forth as SEQ ID NO:1, a portion and/or a derivative thereof, and wherein an increased amount of the biomarker in the biological sample in comparison to the reference amount is indicative of the presence or risk of cardiovascular disease in the subject.

5. The method of claim 1, wherein the amount of the biomarker in the biological sample is detected using mass spectrometry.

6. The method of claim 1, wherein the amount of the biomarker in the biological sample is detected using at least one antibody specific to the biomarker.

* * * * *